United States Patent
Lavis et al.

(10) Patent No.: US 10,407,399 B2
(45) Date of Patent: Sep. 10, 2019

(54) ION-ACTIVATED PHOTOLABILE COMPOUNDS

(71) Applicant: HOWARD HUGHES MEDICAL INSTITUTE, Chevy Chase, MD (US)

(72) Inventors: Luke D. Lavis, Leesburg, VA (US); Jonathan B. Grimm, Ashburn, VA (US); Laurel M. Heckman, Ashburn, VA (US); Eric R. Schreiter, Leesburg, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 0 days.

(21) Appl. No.: 15/756,788

(22) PCT Filed: Sep. 1, 2016

(86) PCT No.: PCT/US2016/049937
§ 371 (c)(1),
(2) Date: Mar. 1, 2018

(87) PCT Pub. No.: WO2017/040805
PCT Pub. Date: Mar. 9, 2017

(65) Prior Publication Data
US 2018/0251441 A1 Sep. 6, 2018

Related U.S. Application Data

(60) Provisional application No. 62/212,976, filed on Sep. 1, 2015.

(51) Int. Cl.
| | |
|---|---|
| *C07D 311/16* | (2006.01) |
| *C07D 307/94* | (2006.01) |
| *C07D 311/82* | (2006.01) |
| *C07D 405/12* | (2006.01) |
| *A61N 5/06* | (2006.01) |
| *A61K 41/00* | (2006.01) |
| *C09K 11/06* | (2006.01) |
| *G01N 21/64* | (2006.01) |
| *G01N 33/58* | (2006.01) |
| *G01N 33/84* | (2006.01) |

(52) U.S. Cl.
CPC ........ *C07D 311/16* (2013.01); *A61K 41/0057* (2013.01); *A61N 5/06* (2013.01); *A61N 5/062* (2013.01); *C07D 307/94* (2013.01); *C07D 311/82* (2013.01); *C07D 405/12* (2013.01); *C09K 11/06* (2013.01); *G01N 21/6428* (2013.01); *G01N 33/582* (2013.01); *G01N 33/84* (2013.01); *C09K 2211/1022* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 5,453,517 A | 9/1995 | Kuhn et al. | |
| 6,313,349 B1 * | 11/2001 | Sato ...................... | C07C 215/82 564/305 |
| 7,776,533 B2 * | 8/2010 | Agnew .................... | C12Q 1/42 435/6.16 |
| 2005/0042662 A1 | 2/2005 | Li et al. | |
| 2012/0009683 A1 | 1/2012 | Gee et al. | |
| 2014/0341845 A1 | 11/2014 | Bourke, Jr. | |

FOREIGN PATENT DOCUMENTS

WO 2015/097313 A1 7/2015

OTHER PUBLICATIONS

The International Bureau of WIPO, International Preliminary Report on Patentability issued in corresponding Application No. PCT/US2016/049937, dated Mar. 15, 2018.
United States Patent and Trademark Office, International Search Report and Written Opinion issued in corresponding Application No. PCT/US2016/049937, dated Oct. 28, 2016.
Lavis, L.D., et al., Synthesis and utility of fluorogenic acetoxymethyl ethers, Chemical Science, 2(3), pp. 1-21 (pp. 521-530), 2011; abstract; p. 19, Scheme 2.
Lavis, L.D. & Raines, R.T. Bright ideas for chemical biology. ACS Chem. Biol. 3, 142-155 (2008).
Lavis, L.D. & Raines, R.T. Bright building blocks for chemical biology. ACS Chem. Biol. 9, 855-866 (2014).
Minta, A. & Tsien, R.Y. Fluorescent indicators for cytosolic sodium. J. Biol. Chem. 264, 19449-19457 (1989).
Minta, A., Kao, J.P. & Tsien, R.Y. Fluorescent indicators for cytosolic calcium based on rhodamine and fluorescein chromophores. J. Biol. Chem. 264, 8171-8178 (1989).
Martin, V.V., Rothe, A., Diwu, Z. & Gee, K.R. Fluorescent sodium ion indicators based on the 1,7-diaza-15-crown-5 system. Bioorg. Med. Chem. Lett. 14, 5313-5316 (2004).

(Continued)

*Primary Examiner* — Samantha L Shterengarts
(74) *Attorney, Agent, or Firm* — Stite & Harbison, PLLC; Mandy Wilson Decker; Summer E. Young

(57) ABSTRACT

The presently-disclosed subject matter relates to analyte-activated photolabile compounds. The compounds include the formula: wherein Z includes a maskable molecule; L is selected from a bond, C, C(O), O, alkyl, (O)alkyl, and alkoxy; $R^1$ is selected from H, halogen, alkyl, and acyl; each $R^2$ is independently selected from H, alkyl, aryl, and acyl, and is optionally substituted with one or more heteroatoms independently selected from COOH and COO(alkyl); and $R^3$ is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, and $SO_3H$, and is optionally substituted with one or more heteroatoms independently selected from N, O, and S, halogen, OH, O(alkyl), O(aryl), SH, S(alkyl), S(aryl), amine, $NO_2$, CHO, COO, COOH, COO(alkyl), COO(aryl), $C(O)NR_2$, $PO_3H_2$, and/or $SO_3H$. Also provided are methods of detecting calcium and treating a subject with the analyte-activated photolabile compounds.

12 Claims, 23 Drawing Sheets

(56) References Cited

OTHER PUBLICATIONS

Adams, S.R. in Imaging in neuroscience and development: a laboratory manual (eds Rafael Yuste & Arthur Konnerth) Ch. 29, 239-244 (CSHL Press, 2005).
Nolan E.M. & Lippard, S.J. Small-molecule fluorescent sensors for investigating zinc metalloneurochemistry. Acc. Chem. Res. 42, 193-203 (2008).
Kamiya, M. & Johnsson, K. Localizable and highly sensitive calcium indicator based on a BODIPY fluorophore. Anal. Chem. 82, 6472-6479 (2010).
Fujii, T et al. Design and Synthesis of a FlAsH-Type $Mg^{2+}$ Fluorescent Probe for Specific Protein Labeling. J. Am. Chem. Soc. 136, 2374-2381 (2014).
Puliti, D., Warther, D., Orange, C., Specht, A. & Goeldner, M. Small photoactivatable molecules for controlled fluorescence activation in living cells. Bioorg. Med. Chem. 19, 1023-1029 (2011).
Kantevari, S., Matsuzaki, M., Kanemoto, Y., Kasai, H. & Ellis-Davies, G.C. Two-color, two-photon uncaging of glutamate and GABA. Nat. Methods 7, 123-125 (2010).
Fournier, L et al. A blue-absorbing photolabile protecting group for in vivo chromatically orthogonal photoactivation. ACS Chem. Biol. 8, 1528-1536 (2013).
Fosque, B.F. et al. Labeling of active neural circuits in vivo with designed calcium integrators. Science 347, 755-760 (2015).
Venkatachalam, V. et al. Flash memory: Photochemical imprinting of neuronal action potentials onto a microbial rhodopsin. J. Am. Chem. Soc. 136, 2529-2537 (2014).
Tsien, R.Y. New calcium indicators and buffers with high selectivity against magnesium and protons: Design, synthesis, and properties of prototype structures. Biochemistry 19, 2396-2404 (1980).
Pethig, R. et al. On the dissociation constants of BAPTA-type calcium buffers. Cell calcium 10, 491-498 (1989).
Schuddeboom, W., Warman, J.M., Biemans, H. & Meijer, E. Dipolar triplet states of p-nitroaniline and N-alkyl derivatives with one-, two-, and three-fold symmetry. J. Phys. Chem. 100, 12369-12373 (1996).
Papageorgiou, G. & Corrie, J.E. Effects of aromatic substituents on the photocleavage of 1-acyl-7-nitroindolines. Tetrahedron 56, 8197-8205 (2000).
Riguet, E. & Bochet, C.G. New safety-catch photolabile protecting group. Org. Lett. 9, 5453-5456 (2007).
Guo, Y.M. et al. Imaging dynamic cell-cell junctional coupling in vivo using Trojan-LAMP. Nat. Methods 5, 835-841 (2008).
Zhao, Y.R. et al. New caged coumarin fluorophores with extraordinary uncaging cross sections suitable for biological imaging applications. J. Am. Chem. Soc. 126, 4653-4663 (2004).
Sabatini, B.L., Oertner, T.G. & Svoboda, K. The life cycle of Ca2+ ions in dendritic spines. Neuron 33, 439-452 (2002).
Wang, S.S.-H., Denk, W. & Häusser, M. Coincidence detection in single dendritic spines mediated by calcium release. Nat. Neurosci. 3, 1266-1273 (2000).
Maravall, M., Mainen, Z., Sabatini, B. & Svoboda, K. Estimating intracellular calcium concentrations and buffering without wavelength ratioing. Biophys. J. 78, 2655-2667 (2000).
Grimm, J.B., Gruber, T.D., Ortiz, G., Brown, T.A. & Lavis, L.D. Virginia Orange: A versatile, red-shifted fluorescein scaffold for single-and dual-input fluorogenic probes. Bioconjugate Chem. 27, 474-480 (2016).
Chan, J., Dodani, S.C. & Chang, C.J. Reaction-based small-molecule fluorescent probes for chemoselective bioimaging. Nature Chem. 4, 973-984 (2012).
Matsuzaki, M. et al. Dendritic spine geometry is critical for AMPA receptor expression in hippocampal CA1 pyramidal neurons. Nat. Neurosci. 4, 1086-1092 (2001).
Diwu, Z. et al. Fluorescent molecular probes. I. The synthesis and biological properties of an ELF b-glucuronidase substrate that yields fluorescent precipitates at the enzymic activity sites. Tetrahedron 53, 7159-7164 (1997).
Kwan, D.H. et al. Self-immobilizing fluorogenic imaging agents of enzyme activity. Angew. Chem. Int. Ed. 123, 314-317 (2011).
Urano, Y. et al. Evolution of fluorescein as a platform for finely tunable fluorescence probes. J. Am. Chem. Soc. 127, 1888-4894 (2005).
Hatchard, C. & Parker, C. A new sensitive chemical actinometer. II. Potassium ferrioxalate as a standard chemical actinometer. Proc. R. Soc. A 235, 518-536 (1956).
Akerboom, J. et al. Optimization of a GCaMP calcium indicator for neural activity imaging. J. Neurosci. 32, 13819-13840 (2012).
Heckman, L.M., et al. Design and Synthesis of a Calcium-Sensitive Photocage. Angew. Chem. Int. Ed 8363-8366 (2016).
Grimm, J. B.; Heckman, L M.; Lavis, L. D. Prog. Mol. Biol. Transl. Sci. 2013, 113, 1-34.
Tsien, R. Y. Ann. Rev. Neurosci. 1989, 12, 227-253.
Sullivan, E; Tucker, E. M.; Dale, I. L. Methods Mol. Biol. 1999, 114, 125-133.
Sawinski, J.; Wallace, D. J.; Greenberg, D. S.; Grossmann, S.; Denk, W.; Kerr, J. N. Proc. Natl. Acad. Sci. U.S.A. 2009, 106, 19557-19562.
Yang, Y.; Zhao, Q.; Feng, W.; Li, F. Chem. Rev. 2012, 113, 192-270.
Clapham, D. E. Cell 2007, 131, 1047-1058.
Kobayashi, T.; Urano, Y.; Kamiya, M.; Ueno, T.; Kojima, H.; Nagano, T. J. Am. Chem. Soc. 2007, 129, 3696-6697.
Kwan, D. H.; Chen, H. M.; Ratananikom, K.; Hancock, S. M.; Watanabe, Y.; Kongsaeree, P. T.; Samuels, A. L; Withers, S. G. Angew. Chem., Int. Ed. 2011, 50, 300-303.

* cited by examiner

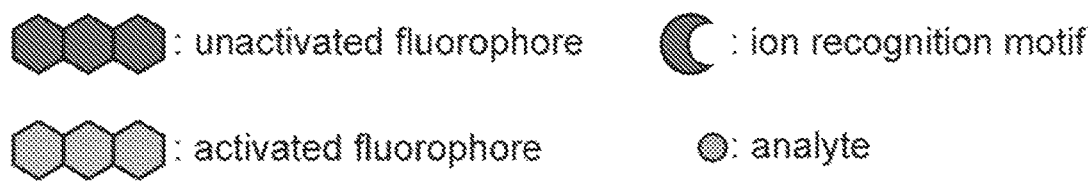
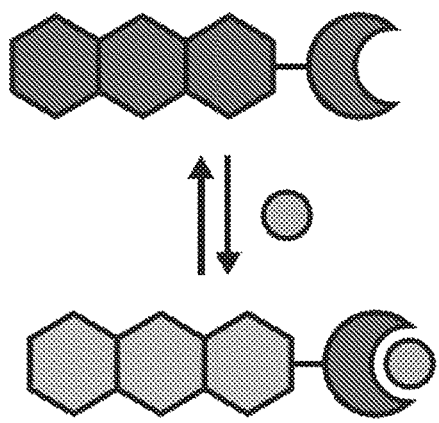
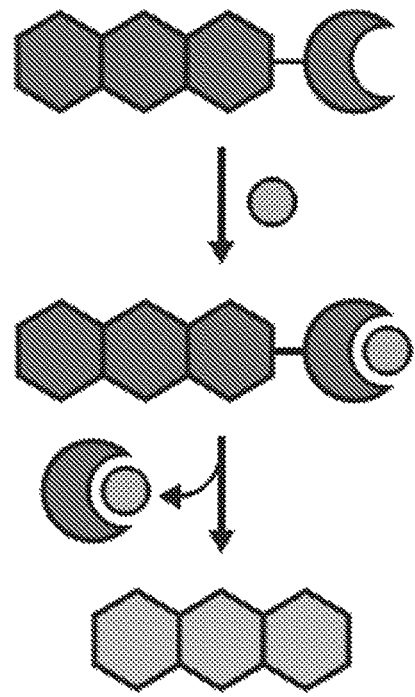
Figure 1A
Figure 1B

ION-ACTIVATED PHOTOLABILE COMPOUNDS

RELATED APPLICATIONS

This application claims priority from U.S. Provisional Application Ser. No. 62/212,976, filed Sep. 1, 2015, the entire disclosure of which is incorporated herein by this reference.

TECHNICAL FIELD

The presently-disclosed subject matter relates to caged compounds. In particular, the presently-disclosed subject matter relates to ion-activated photolabile compounds as well as method for making and using the same.

BACKGROUND

Fluorogenic molecules facilitate advanced biochemical and biological experiments. In particular, the ability to modify dyes using chemistry allows the construction of numerous probes for specific applications. For example, changing the chemical structure of fluorophores can allow fine-tuning of spectral properties. These fluorophores form a class of synthetic ion indicators that respond to changes in ion concentration, also known as chemosensors (FIG. 1A). The design and synthesis of such "smart" probes involves incorporation of ion recognition motifs into fluorophores. After incorporation, reversible binding of these ion recognition motifs to a specific ion alters the fluorescence output of the molecule through transient changes in absorption or fluorescence quantum yield.

This strategy has produced probes for many biologically relevant ions, including $Na^+$, $K^+$, $Mg^{2+}$, $Ca^{2+}$, and $Zn^{2+}$, allowing non-invasive monitoring of ion concentration inside living cells. By allowing passive measurement of environmental changes in disparate contexts, including inside living cells, such probes have revolutionized biological research, facilitating a variety of key technologies including functional imaging of cellular activity in culture and in vivo. While this mode of sensing yields temporal information, it requires constant monitoring and complex setups to read out changes in ion concentration.

Another class of indicators includes chemodosimeters (i.e., reaction-based probes; FIG. 1B). In contrast to the transient change in fluorescence provided by chemosensor, the binding of an analyte to a chemodosimeters elicits an irreversible chemical reaction that alters fluorescence. This mode of sensing allows a simple endpoint measurement of fluorescence change, however, it also lacks the temporal granularity of reversible chemosensors.

Accordingly, there remains a need for compounds that have the temporal specificity of reversible chemosensors as well as the endpoint measurement capabilities of chemodosimeter systems.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes ion-activated photolabile compounds. In some embodiments, the compounds include the formula:

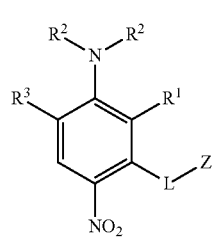

Wherein Z includes a maskable molecule; L is selected from a bond, C, C(O), O, alkyl, (O)alkyl, and alkoxy; $R^1$ is selected from H, halogen, alkyl, and acyl; each $R^2$ is independently selected from H, alkyl, aryl, and acyl, and is optionally substituted with one or more heteroatoms independently selected from COOH and COO(alkyl) or the $R^2$ groups, taken together with the carbon atom to which they are bound, form a 4-10 membered ring; and $R^3$ is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, and $SO_3H$, and is optionally substituted with one or more heteroatoms independently selected from N, O, and S, halogen, OH, O(alkyl), O(aryl), SH, S(alkyl), S(aryl), amine, $NO_2$, CHO, COO, COOH, COO(alkyl), COO(aryl), $C(O)NR_2$, $PO_3H_2$, and/or $SO_3H$. In some embodiments, Z is selected from the group consisting of a fluorophore and an active agent. In some embodiments, the active agent includes an enzyme, catalyst, ribozyme, organometallic, protein, glycoprotein, peptide, polyamino acid, antibody, nucleic acid, steroidal molecule, antibiotic, antiviral, antimycotic, anticancer agent, analgesic agent, antirejection agent, immunosuppressant, cytokine, carbohydrate, oleophobic, lipid, pharmaceutical, chemotherapeutic, or combinations thereof. In some embodiments, $R^2$ is selected from $CH_2COOH$ and $CH_2COO(alkyl)$.

In some embodiments, the compound of the presently-disclosed subject matter includes the formula:

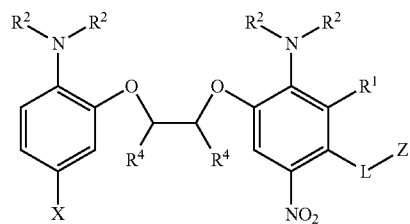

Wherein each $R^4$ is independently selected from H, alkyl, and alkenyl; and X is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, and $SO_3H$, $R^3$ being optionally substituted with one or more heteroatoms independently selected from N, O, and S, halogen, OH, O(alkyl), O(aryl), SH, S(alkyl), S(aryl), amine, $NO_2$, CHO, COO, COOH, COO(alkyl), COO(aryl), $C(O)NR_2$, $PO_3H_2$, and/or $SO_3H$. In some embodiments, X is selected from methoxy and pyrrolidine. More specifically, in one embodiment, the compound includes the formula:

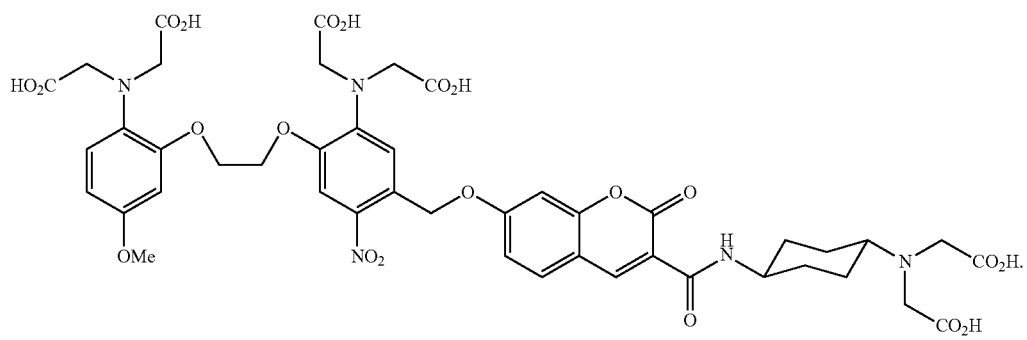 [SMILES: COc1ccc(N(CC(=O)O)CC(=O)O)c(OCCOc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]
In another embodiment, the compound includes the formula:
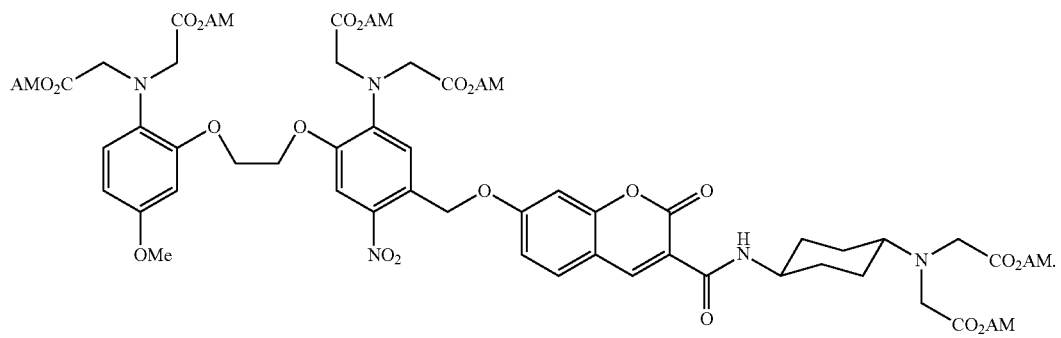
In one embodiment, the compound includes the formula:
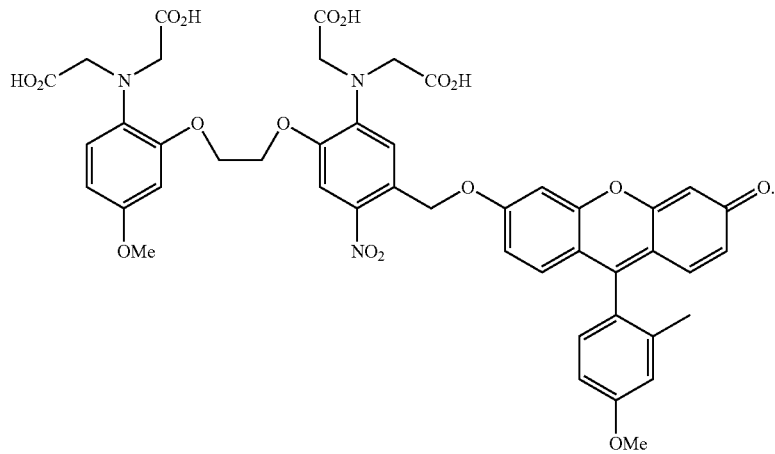 [SMILES: COc1ccc(-c2c3ccc(=O)cc-3oc3cc(OCc4cc(N(CC(=O)O)CC(=O)O)c(OCCOc5cc(OC)ccc5N(CC(=O)O)CC(=O)O)cc4[N+](=O)[O-])ccc23)c(C)c1]
In one embodiment, the compound includes the formula:
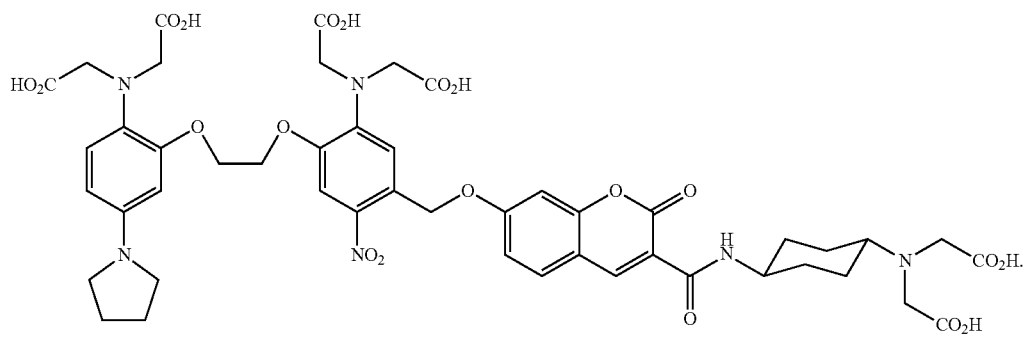 [SMILES: O=C(O)CN(CC(=O)O)c1ccc(N2CCCC2)cc1OCCOc1cc([N+](=O)[O-])c(COc2ccc3cc(C(=O)NC4CCC(N(CC(=O)O)CC(=O)O)CC4)c(=O)oc3c2)cc1N(CC(=O)O)CC(=O)O]

In some embodiments, the $R^4$ groups, taken together with the carbon atoms to which they are bound, form a 5-6 membered ring. For example, in one embodiment, the compound includes the formula:

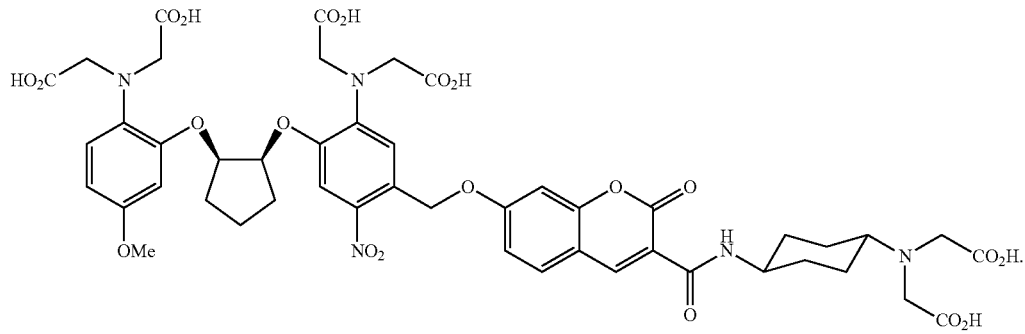 [SMILES: COc1ccc(N(CC(=O)O)CC(=O)O)c(O[C@@H]2CCC[C@@H]2Oc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]

In some embodiments, the compound includes a two-cage system having two analyte-activated photolabile compounds attached to a maskable molecule. For example, in one embodiment, the two-cage system includes the formula:

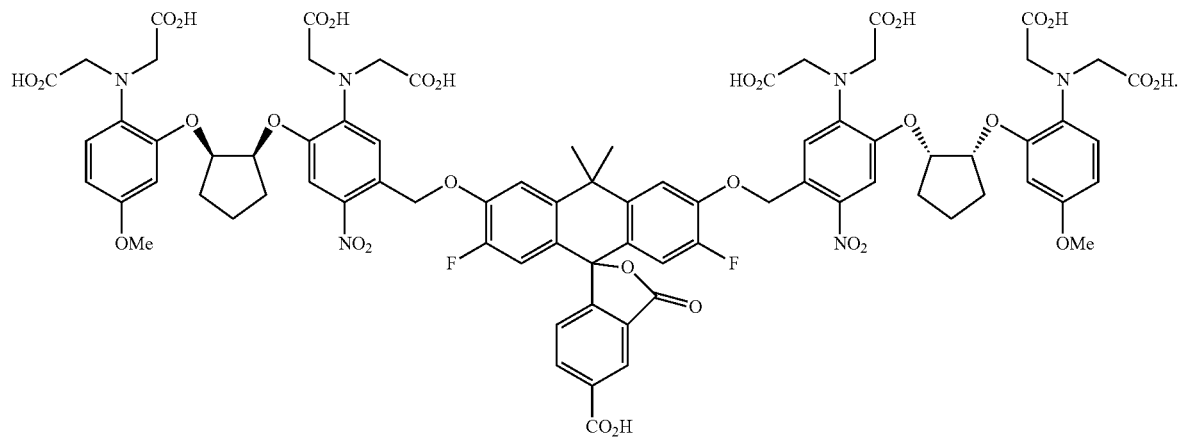 [SMILES: COc1ccc(N(CC(=O)O)CC(=O)O)c(O[C@@H]2CCC[C@@H]2Oc2cc([N+](=O)[O-])c(COc3cc4c(cc3F)C3(OC(=O)c5cc(C(=O)O)ccc53)c3cc(F)c(OCc5cc(N(CC(=O)O)CC(=O)O)c(O[C@H]6CCC[C@H]6Oc6cc(OC)ccc6N(CC(=O)O)CC(=O)O)cc5[N+](=O)[O-])cc3C4(C)C)cc2N(CC(=O)O)CC(=O)O)c1]

In some embodiments, the presently-disclosed subject matter includes a method for detecting calcium in a sample. For example, in one embodiment, the method includes contacting the sample with a compound of the formula:

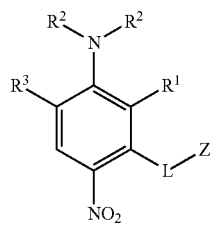

exposing the sample to an activation light and an excitation light; and detecting an emission light from the fluorophore, the emission light indicating the presence of calcium. Wherein Z includes a fluorophore; L is selected from a bond, C, C(O), O, alkyl, (O)alkyl, and alkoxy; $R^1$ is selected from H, halogen, alkyl, and acyl; each $R^2$ is independently selected from H, alkyl, aryl, and acyl, and is optionally substituted with one or more heteroatoms independently selected from COOH and COO(alkyl), or the $R^2$ groups, taken together with the carbon atom to which they are bound, form a 4-10 membered ring; $R^3$ is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, and $SO_3H$, $R^3$ being optionally substituted with one or more heteroatoms independently selected from N, O, and S, halogen, OH, O(alkyl), O(aryl), SH, S(alkyl), S(aryl), amine, $NO_2$, CHO, COO, COOH, COO(alkyl), COO(aryl), $C(O)NR_2$, $PO_3H_2$, and/or $SO_3H$. In another embodiment, the activation light is the same as the excitation light. In a further embodiment, the activation light and/or the excitation light includes a wavelength of about 300 nm to about 1000 nm.

In some embodiments, the presently-disclosed subject matter includes a method for treating a subject. For example, in one embodiment, the method includes administering to the subject a compound of the formula:

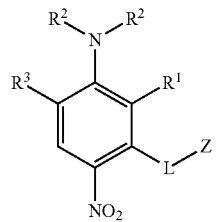

and exposing the subject to an activation light. Wherein Z includes an active agent; L is selected from a bond, C, C(O), O, alkyl, (O)alkyl, and alkoxy; $R^1$ is selected from H, halogen, alkyl, and acyl; each $R^2$ is independently selected from H, alkyl, aryl, and acyl, and is optionally substituted with one or more heteroatoms independently selected from COOH and COO(alkyl) or the $R^2$ groups, taken together with the carbon atom to which they are bound, form a 4-10 membered ring; and $R^3$ is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, and $SO_3H$, $R^3$ being optionally substituted with one or more heteroatoms independently selected from N, O, and S, halogen, OH, O(alkyl), O(aryl), SH, S(alkyl), S(aryl), amine, $NO_2$, CHO, COO, COOH, COO(alkyl), COO(aryl), $C(O)NR_2$, $PO_3H_2$, and/or $SO_3H$. In another embodiment, the active agent includes an enzyme, catalyst, ribozyme, organometallic, protein, glycoprotein, peptide, polyamino acid, antibody, nucleic acid, steroidal molecule, antibiotic, antiviral, antimycotic, anticancer agent, analgesic agent, antirejection agent, immunosuppressant, cytokine, carbohydrate, oleophobic, lipid, pharmaceutical, chemotherapeutic, or combinations thereof. In a further embodiment, the activation light includes a wavelength of about 300 nm to about 1000 nm.

BRIEF DESCRIPTION OF THE DRAWINGS

The novel features of the subject matter of the present disclosure are set forth with particularity in the appended claims. A better understanding of the features and advantages of the presently disclosed subject matter will be obtained by reference to the following detailed description that sets forth illustrative embodiments, in which the principles of the present disclosure are used, and the accompanying drawings of which:

FIG. 1A includes a schematic representation of reversible chemosensors.

FIG. 1B includes a schematic representation of irreversible chemodosimeters.

DETAILED DESCRIPTION OF EXEMPLARY EMBODIMENTS

Figure 2:
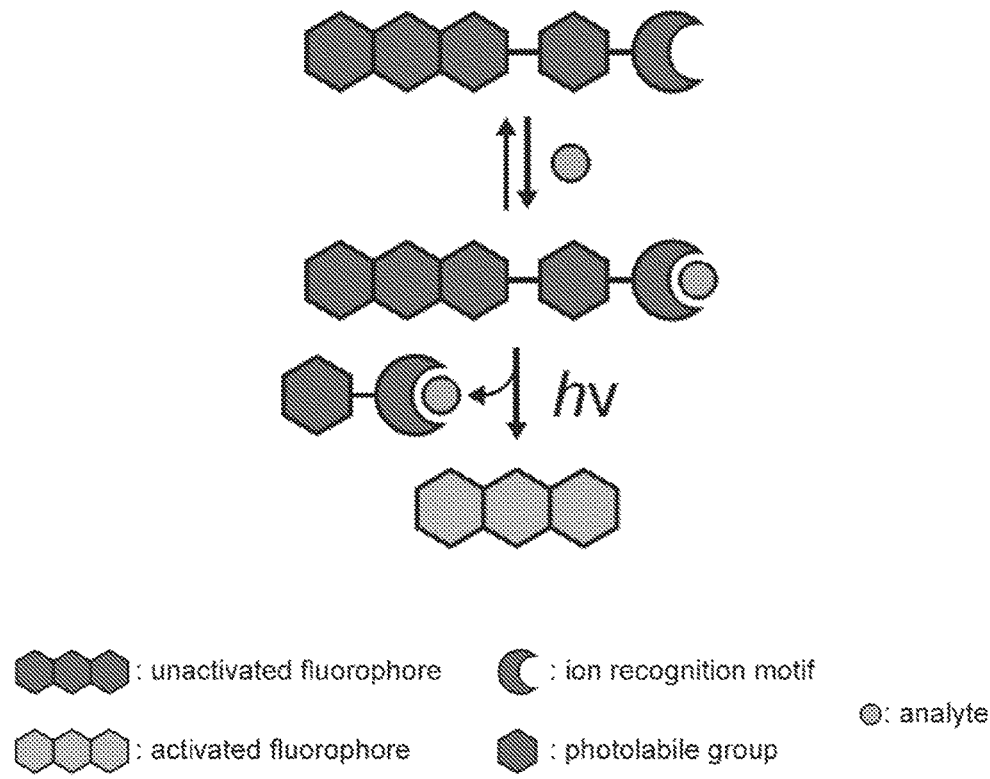
FIG. 2 includes a schematic representation of an embodiment of the presently-disclosed ion-activated photolabile compounds.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "maskable molecule" is used herein to refer to any molecule that can be incorporated into the present compounds and remains in an inactive state until the compound is activated by combined exposure to a particular activating analyte and activation light. In other words, the maskable molecule can remain inactive, or masked, until environmental conditions combined with a light input cause a release of the maskable molecule in an active state. Exemplary maskable molecules include, but are not limited to, fluorophores, such as precipitating dyes and reactive dyes, active agents, including those described herein, and the like. Those of ordinary skill in the art upon reviewing this paper will appreciate other maskable molecules that may be incorporated and for which it would be desirable to have an activation that is dependent both on environmental factors (e.g., analyte concentration) and external stimuli (e.g., exposure to activation light).

In this respect, the term "active agent" is used herein to refer to substances that can alter, inhibit, active, catalyze, or otherwise affect a biological or chemical event in a subject. Active agents can be used to treat a certain disease or condition in a subject. Exemplary active agents include, but are not limited to, enzymes, catalysts, ribozymes, organometallics, proteins, glycoproteins, peptides, polyamino acids, antibodies, nucleic acids (e.g., siRNA, miRNA), steroidal molecules, antibiotics, antivirals, antimycotics, anticancer agents, analgesic agents, antirejection agents, immunosuppressants, cytokines, carbohydrates, oleophobics, lipids, pharmaceuticals, chemotherapeutics, and combinations thereof.

The presently-disclosed subject matter includes analyte-activated photolabile compounds. In some embodiments, the compounds of the presently-disclosed subject matter include a photolabile group with an analyte recognition unit. In one embodiment, the photolabile group and the analyte recognition unit function together as an analyte-dependent caged molecule. In another embodiment, the analyte recognition unit includes an ion recognition unit, the photolabile group and the ion recognition unit functioning together as an ion-dependent caged molecule. Embodiments of the present compounds further comprise a maskable molecule that is bound to the photolabile group. Together, the ion-dependent caged molecule and the maskable molecule form an ion-activated photolabile compound that is activated by coincident ion binding and illumination by an activation light (FIG. 2).

In some embodiments, the present compounds yield a permanent fluorescent change that is correlated with cumulative analyte (e.g., ion) concentration during a defined epoch. For example, in one embodiment, activation of the compound through coincident analyte binding and illumination selectively and irreversibly releases a small molecule therefrom. This irreversible release of the small molecule permanently records analyte concentration during a time window defined by the coincident illumination. Embodiment of the present compounds are therefore capable of sensing analytes (e.g., ions) in a system that combines the temporal specificity of reversible chemosensors with the endpoint measurement of chemodosimeters. Accordingly, the presently-disclosed ion-dependent caged molecules can also be referred to as light-gated chemodosimeters herein.

In some embodiments, the presently-disclosed compounds include the formula:

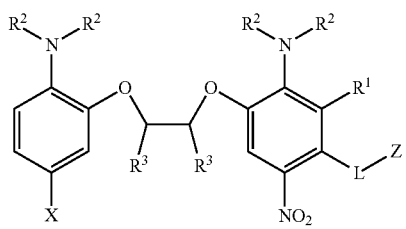

wherein Z includes a maskable molecule; L is selected from a bond, C, C(O), O, alkyl, (O)alkyl; $R^1$ is selected from H, alkyl and acyl; each $R^2$ is independently selected from H, alkyl, aryl, and acyl, and is optionally substituted with $CH_2CO_2H$, or the $R^2$ groups, taken together with the carbon atom to which they are bound, form a 4-10 membered ring; each $R^3$ is independently selected from H, alkyl, and alkenyl; and X is selected from, substituted or unsubstituted, alkyl, aryl, alkoxy, and amino.

Additionally or alternatively, in some embodiments, the presently-disclosed compound includes a two-cage system with the formula:

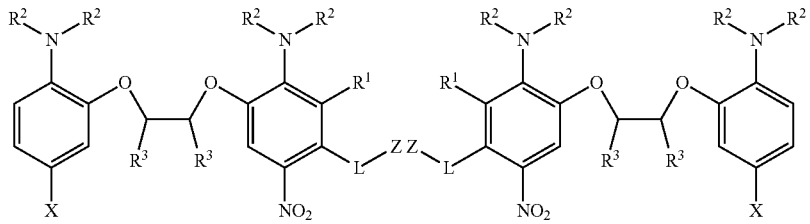

wherein Z includes a maskable molecule; L is selected from a bond, C, C(O), O, alkyl, (O)alkyl; $R^1$ is selected from H, alkyl and acyl; each $R^2$ is independently selected from H, alkyl, aryl, and acyl, and is optionally substituted with $CH_2CO_2H$; each $R^3$ is independently selected from H, alkyl, and alkenyl; and X is selected from, substituted or unsubstituted, alkyl, aryl, alkoxy, and amino.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "A1," "A2," "A3," and "A4" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like. In some instances the term alkyl is used herein interchangeably with the term cycloalkyl.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA1 where A1 is alkyl or cycloalkyl as defined above. "Alkoxy" also includes polymers of alkoxy groups as just described; that is, an alkoxy can be a polyether such as —OA1-OA2 or —OA1-(OA2)a-OA3, where "a" is an integer of from 1 to 200 and A1, A2, and A3 are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as (A1A2)C═C(A3A4) are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, haide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "acyl" as used herein refers to a radical provided by the residue remaining after removal of one or more hydroxyl groups from an organic acid. Examples of acyl include, but are not limited to, lower alkanoyls, such as acetyl, and benzoyl, alkenoyl, aroyl, and the like.

The terms "amine" or "amino" as used herein are represented by a formula NA1A2A3, where A1, A2, and A3 can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of NH2, NH(alkyl), NH(aryl), N(alkyl)2, and N(aryl)2.

The term "ester" as used herein is represented by a formula OC(O)A1 or C(O)OA1, where A1 can be an optionally substituted alkyl, cycloalkyl, alkenyl, cycloalkenyl, alkynyl, cycloalkynyl, aryl, or heteroaryl group as described herein. The term "polyester" is used herein to describe a group that is produced by the reaction between a compound having at least two carboxylic acid groups with a compound having at least two hydroxyl groups. For example, in some embodiments, the term "polyester" as used herein is represented by a formula -(A1O(O)C-A2-C(O)a- or -(A1O(O)C-A2-OC(O))a-, where A1 and A2 can be, independently, an optionally substituted alkyl, cycloalkyl, alkenyl, cycloalkenyl, alkynyl, cycloalkynyl, aryl, or heteroaryl group described herein and "a" is an integer from 1 to 500.

In some embodiments R2 includes, but is not limited to, CH2COOH, CH2COO(alkyl), or a combination thereof. For example, R2 may be selected from

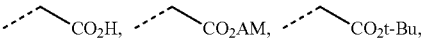

and combinations thereof. In some embodiments X includes OMe.

The presently-disclosed compounds can be modified to incorporate a variety of different maskable molecules as well as different structures. In one embodiment the compound includes the following formula:

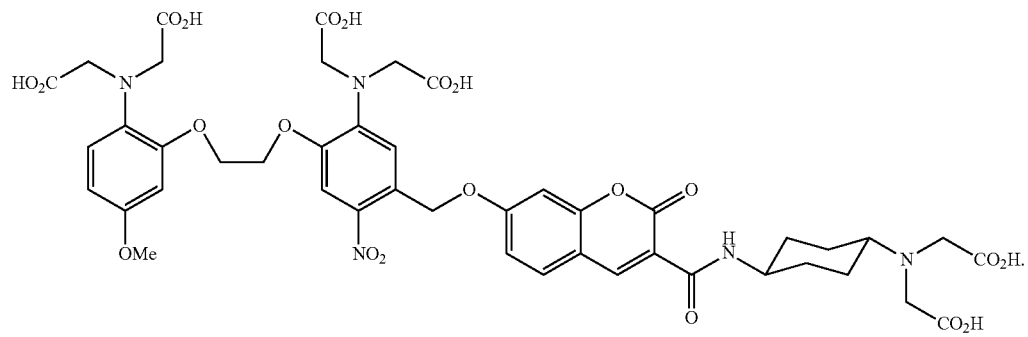 [SMILES: COc1ccc(N(CC(=O)O)CC(=O)O)c(OCCOc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]

In other embodiments the compounds includes the following formula:

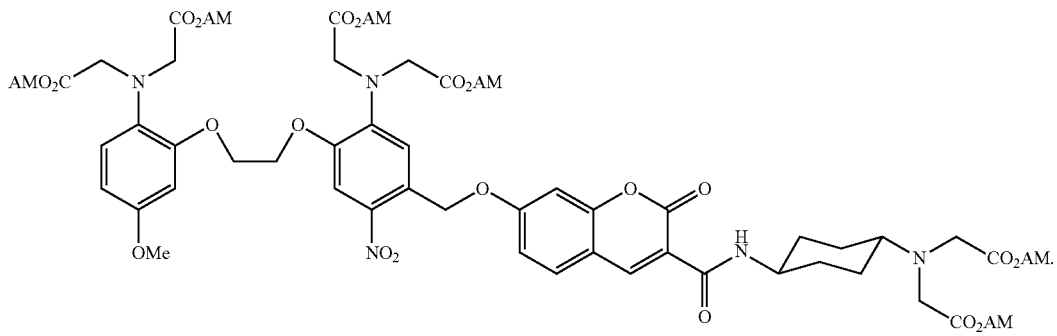

In other embodiments the compounds includes the following formula:

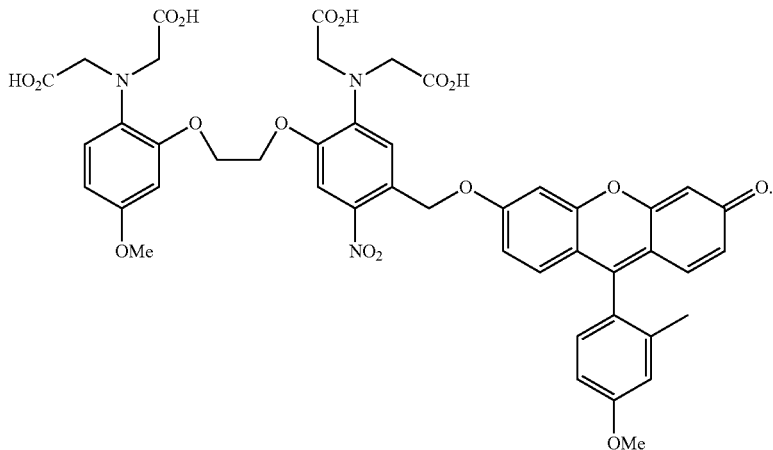 [SMILES: COc1ccc(-c2c3ccc(=O)cc-3oc3cc(OCc4cc(N(CC(=O)O)CC(=O)O)c(OCCOc5cc(OC)ccc5N(CC(=O)O)CC(=O)O)cc4[N+](=O)[O-])ccc23)c(C)c1]

The presently-disclosed compounds also includes derivatives of any of the compounds described herein. As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

The compounds described herein can contain one or more double bonds and, thus, potentially can give rise to cis/trans (E/Z) isomers, as well as other conformational isomers. Unless stated to the contrary, the invention includes all such possible isomers, as well as mixtures of such isomers. Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Figure 3:
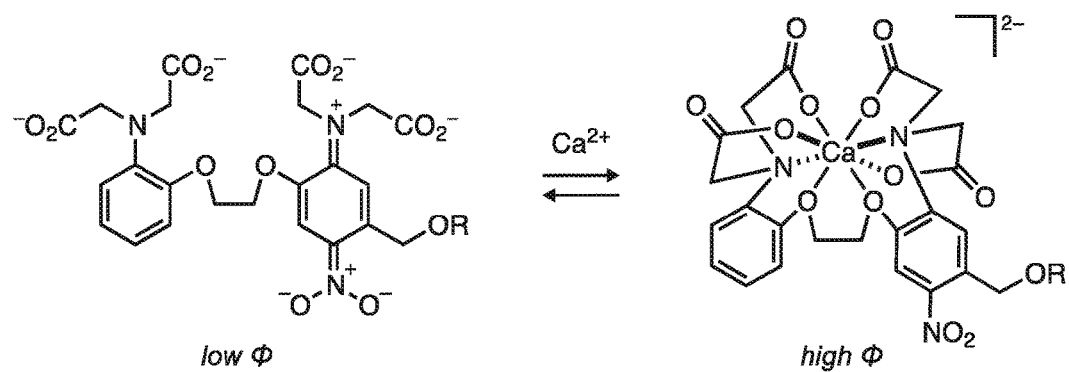
FIG. 3 includes a schematic representation of the function of a compound according to an embodiment disclosed herein.

In this regard, the structure and function of an embodiment of the presently-disclosed compounds is shown in FIG. 3. As illustrated in FIG. 3, in one embodiment, the compound exhibits low photochemical quantum yield in the absence of Ca2+ and high photochemical quantum yield in the presence of Ca2+. The embodied compound incorporates an o-nitrobenzyl photolabile group into the calcium ion chelator moiety 1,2-bis(o-aminophenoxy)ethane-N,N,N',N'-tetraacetic acid (BAPTA). Without being bound by theory or mechanism, in the absence of Ca2+, the para-nitroaniline ring adopts a charge-separated colored form, which exhibits a low-lying triplet state, thus preventing photochemical release. However, binding of an analyte, in this case Ca2+, reverses this effect as the aniline nitrogen lone pair participates in chelation. This recapitulates the o-nitrobenzyl electronic structure and increases photochemical quantum yield. In other embodiments, nitroindoline or the like can be used rather than o-nitrobenzyl.

As discussed herein, the presently disclosed subject matter further includes methods for detecting an analyte in a sample. Exemplary methods for detecting an analyte include methods for detecting calcium in a sample, wherein the methods comprise contacting the sample with a compound of the formula:

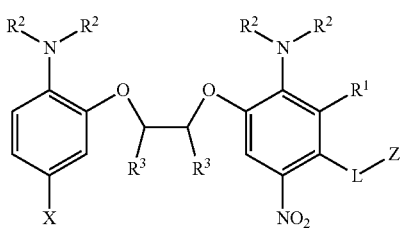

wherein Z includes a fluorophore, L is selected from a bond, C, C(O), O, alkyl, (O)alkyl, $R^1$ is selected from H, alkyl and acyl, each $R^2$ is independently selected from H, alkyl, aryl, and acyl, and is optionally substituted with $CH_2CO_2H$, or the $R^2$ groups, taken together with the carbon atom to which they are bound, form a 4-10 membered ring, each $R^3$ is independently selected from H, alkyl, and alkenyl, and X is selected from, substituted or unsubstituted, alkyl, aryl, alkoxy, and amino. Next, some embodiments of methods for detecting an analyte include a step of exposing the sample to an activation light and an excitation light, and then detecting an emission light from the fluorophore, the emission light indicating the presence of calcium.

The term "activation light" is used herein to refer to electromagnetic radiation capable of releasing a photo-labile group from a compound when the compound is in the presence of an activating analyte (e.g. Ca2+). Exposure of the present compounds to an activation light in the presence of an activating analyte therefore triggers release of a previously bound maskable molecule. In some embodiments the activation light includes a wavelength of about 300 nm, 350 nm, 400 nm, 450 nm, 500 nm, 550 nm, 600 nm, 650 nm, 700 nm, 750 nm, 800 nm, 850 nm, 900 nm, 950 nm, or 1,000 nm.

The term "excitation light" is used herein to refer to electromagnetic radiation capable of exciting a fluorophore so that the fluorophore emits an "emission light." Compounds according to the presently-disclosed subject matter can be exposed to an excitation light at the same time as or subsequent to being exposed to an activation light. In some embodiments the excitation light includes a wavelength of about 300 nm, 350 nm, 400 nm, 450 nm, 500 nm, 550 nm, 600 nm, 650 nm, 700 nm, 750 nm, 800 nm, 850 nm, 900 nm, 950 nm, or 1,000 nm. In some instances the activation light is the same as the excitation light such that exposure to one light source can cause both the release and excitation of a fluorophore. In some embodiments the emission light includes a wavelength of about 300 nm to about 1,000 nm.

While the embodiments described herein are configured to from a photocage in the presence of Ca2+ ions, the present compounds are not limited to Ca2+-dependent embodiments. In other embodiments the present compounds can be Mg2+-dependent photolabile compounds. In other embodiments the present compounds can be Zn2+-dependent photolabile compounds. In other embodiments the present compounds can be Na+-dependent photolabile compounds. In other embodiments the present compounds can be K+-dependent photolabile compounds.

Methods for the detection of one or more analytes illustrate that the present compounds can be utilized to observe, image, and characterize the location and/or concentration of particular analytes. In some embodiments the present compounds can exhibit a high photochemical contrast, and exemplary compounds can exhibit a 10-fold, 20-fold, 30-fold, 40-fold, 50-fold, 60-fold, 70-fold, 80-fold, 90-fold, 100-fold, or more increase in photochemical quantum yield upon chelation. For example, in one embodiment, the compound is a Ca2+-dependent caged molecule which exhibits about a 600-fold increase in photochemical quantum yield upon binding Ca2+ in the presence of an activation light. In some implementations the present compounds can be utilized for post hoc mapping of active cells, including those in complex tissues, with temporal sensitivity. For instance, use of fluorophores with different wavelengths, as well as precipitating or reactive dyes, can enable the post hoc mapping of active cells or subcellular regions with high temporal precision.

The presently disclosed subject matter also includes methods for delivering an active agent, wherein the active agents are be released in an active state from the compounds upon being simultaneously exposed to an activating analyte and an activating light. Methods for delivering an active agent can be configured to target only particular cells, environments, or the like. Embodiments of methods for delivering an active agent can be used in the treatment of diseases or conditions, for experimental purposes, or the like.

Some embodiments of active agent delivery methods include methods for treating a subject, wherein the methods comprise administering to the subject a compound of the formula:

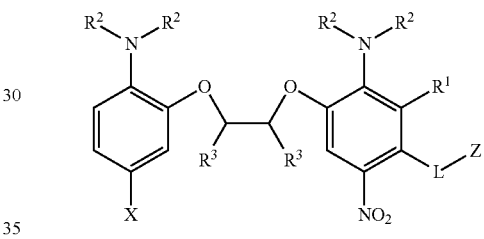

wherein Z includes an active agent, L is selected from a bond, C, C(O), O, alkyl, (O)alkyl, $R^1$ is selected from H, alkyl and acyl, each $R^2$ is independently selected from H, alkyl, aryl, and acyl, and is optionally substituted with $CH_2CO_2H$, or the $R^2$ groups, taken together with the carbon atom to which they are bound, form a 4-10 membered ring, each $R^3$ is independently selected from H, alkyl, and alkenyl, and X is selected from, substituted or unsubstituted, alkyl, aryl, alkoxy, and amino. Next, methods for treating a subject include a step of exposing the sample to an activation light to thereby release the active agent.

Further still, the presently-disclosed subject matter also includes methods for preparing the present compounds as well as their intermediates.

Figure 4:
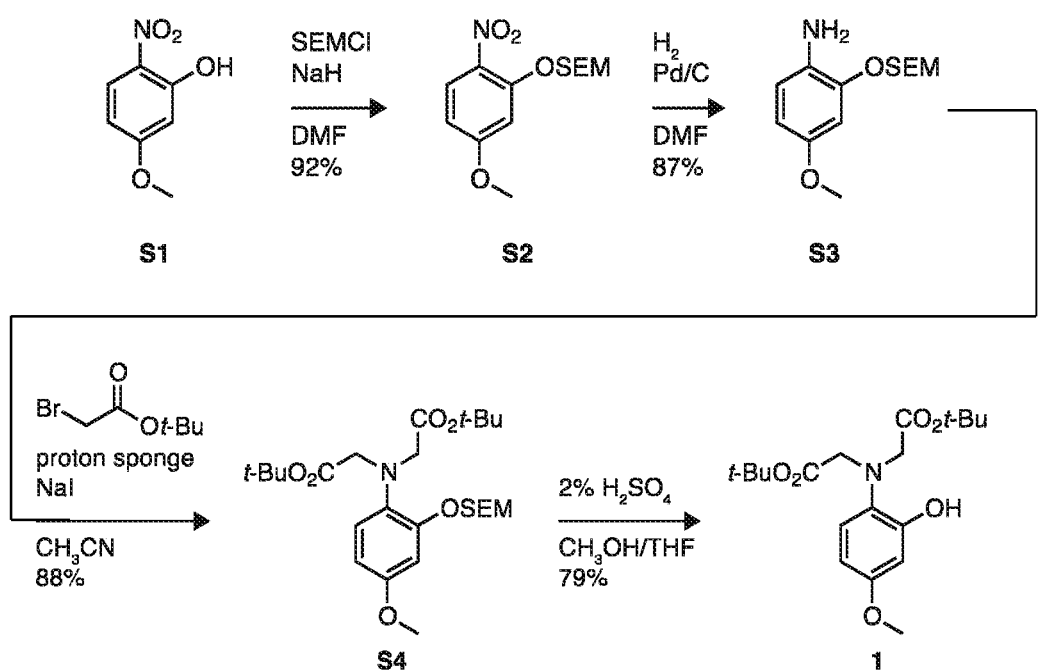
FIG. 4 includes a schematic representation of the synthesis of a compound according to an embodiment of the disclosure.

In some embodiments, preparing the present compounds includes preparing di-tert-butyl 2,2'-((2-hydroxy-4-methoxyphenyl)azanediyl)diacetate (1), the structure of which is shown below. For example, in one embodiment, as shown in FIG. 4 and described in detail in the Examples contained herein, preparing compound 1 includes first combining 5-methoxy-2-nitrophenol (S1) in DMF, NaH, and 2-(trimethylsilyl)ethoxymethyl chloride to form (2-((5-Methoxy-2-nitrophenoxy)methoxy)ethyl)trimethylsilane (S2). Next, Pd/C is added to compound S2 dissolved in DMF, the reaction is flushed with nitrogen and $H_2$, stirred, filtered, and concentrated to form 4-Methoxy-2-((2-(trimethylsilyl)ethoxy)methoxy)aniline (S3). Compound S3 is then dissolved in MeCN, combined with 1,8-bis(dimethylamino)naphthalene, tert-butyl bromoacetate, and NaI, the mixture is stirred, the solvent is evaporated to form a residue, and the residue is diluted, washed, dried, filtered, and concentrated to form di-tert-butyl 2,2'-((4-methoxy-2-((2-(trimethylsilyl)ethoxy)methoxy)phenyl)azanediyl)diacetate (S4). Finally, compound S4 is combined with H₂SO₄ in MeOH, the mixture is stirred, quenched, diluted, and extracted to form compound 1.

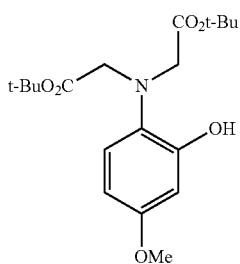

Figure 5:
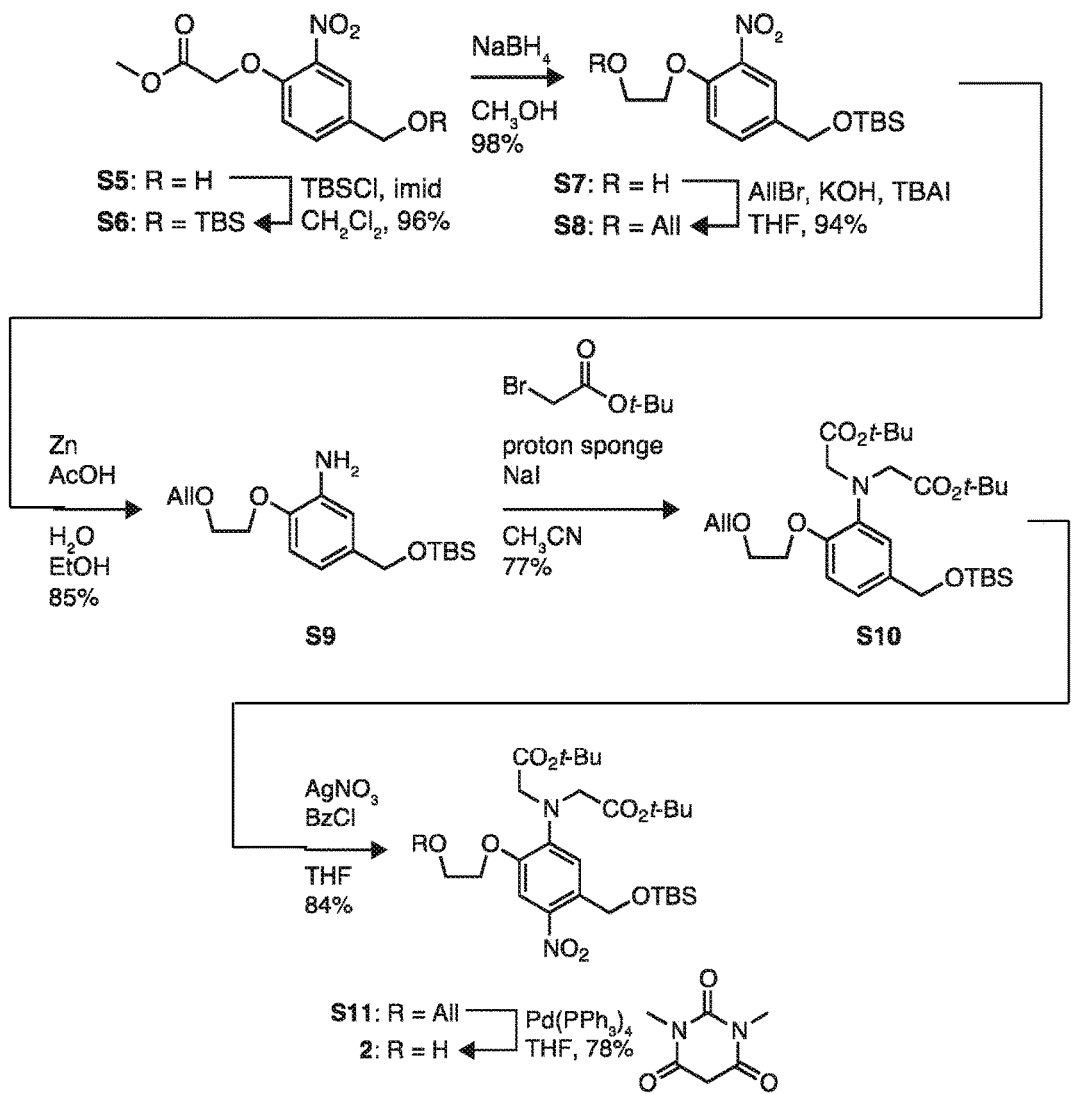
FIG. 5 includes a schematic representation of the synthesis of a compound according to an embodiment of the disclosure.

In some embodiments, preparing the present compounds includes preparing di-tert-butyl 2,2'-((5-(((tert-butyldimethylsilypoxy)methyl)-2-(2-hydroxyethoxy)-4-nitrophenypazanediyl) diacetate (2), the structure of which is shown below. For example, in one embodiment, as shown in FIG. 5 and described in detail in the Examples contained herein, preparing compound 2 includes first combining Methyl 2-[4-(Hydroxymethyl)-2-nitrophenoxy]acetate (S5) and imidazole to form Methyl 2-(4-(((tert-butyldimethylsilypoxy)methyl)-2-nitrophenoxy)acetate (S6). Next, NaBH₄ is added to compound S6 to form 2-(4-(((tert-Butyldimethylsilyl)oxy)methyl)-2-nitrophenoxy)ethanol (S7). After forming S7, a vial is charged with S7, allyl bromide, and tetrabutylammonium iodide, the mixture is stirred, and the stirred mixture is diluted with CH₂Cl₂ and Celite to form ((4-(2-(Allyloxy)ethoxy)-3-nitrobenzypoxy)(tert-butyl)dimethylsilane (S8). S8 then is combined with EtOH, H₂O, AcOH, and zinc powder, stirred, filtered, and rinsed to form 2-(2-(Allyloxy)ethoxy)-5-(((tert-butyldimethylsilyl)oxy) methyDaniline (S9), which is dissolved in MeCN and mixed with 1,8-bis(dimethylamino)naphthalene, tert-butyl bromoacetate, and NaI to form di-tert-butyl 2,2'-((2-(2-(allyloxy)ethoxy)-5-(((tert-butyldimethylsilyl)oxy)methyl)phenyl)azanediyl)diacetate (S10). Thereafter, compound S10 is taken up in MeCN under nitrogen, mixed with AgNO₃ and benzoyl chloride, and filtered to remove AgCl and form di-tert-butyl 2,2'-((2-(2-(allyloxy)ethoxy)-5-(((tert-butyldimethylsilyl)oxy)methyl)-4-nitrophenyl)azanediyl) diacetate (S11). Finally, compound S11 is combined with 1,3-dimethylbarbituric acid and Pd(PPh₃)₄ in a round-bottom flask equipped with a condenser, flushed with nitrogen, mixed with THF, diluted, extracted, and dried to form compound 2.

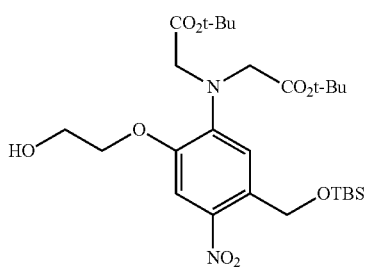

Figure 6:
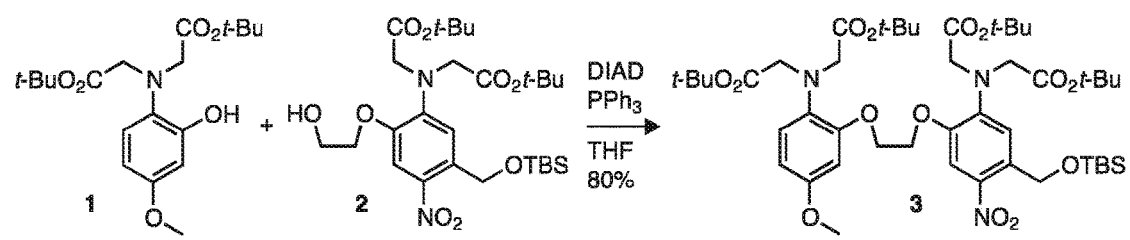
FIG. 6 includes a schematic representation of the synthesis of a compound according to an embodiment of the disclosure.

In some embodiments, preparing the present compounds includes preparing di-tert-butyl 2,2'-((2-(2-(2-(bis(2-(tert-butoxy)-2-oxoethyl)amino)-4-(((tert-butyldimethylsilypoxy)methyl)-5-nitrophenoxy)ethoxy)-4-methoxyphenyl)azanediyl)diacetate (3), the structure of which is shown below. For example, in one embodiment, as shown in FIG. 6 and described in detail in the Examples contained herein, preparing compound 3 includes first charging a vial with a phenol, such as compound 1, an alcohol, such as compound 2, and PPh₃. Next, the vial is sealed and evacuated with nitrogen, THF is added, and the resulting mixture is sonicated. DIAD is then added and the reaction is sonicated again, after which the mixture is purified to provide compound 3.

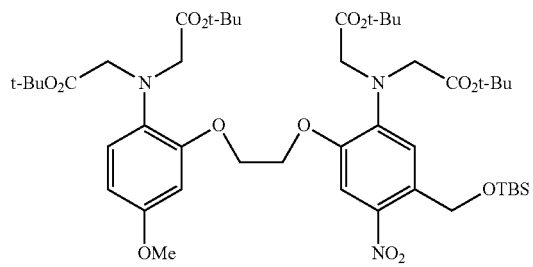

Figure 7:
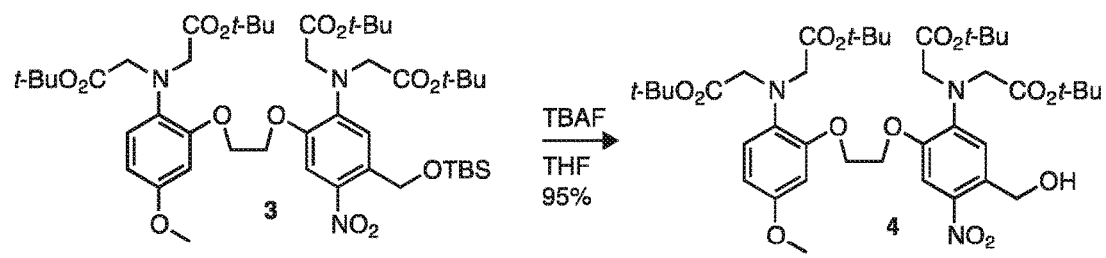
FIG. 7 includes a schematic representation of the synthesis of a compound according to an embodiment of the disclosure.

In some embodiments, preparing the present compounds includes preparing di-tert-butyl 2,2'-((2-(2-(2-(bis(2-(tert-butoxy)-2-oxoethyl)amino)-4-(hydroxymethyl)-5-nitrophenoxy)ethoxy)-4-methoxyphenyl)azanediyl)diacetate (4), the structure of which is shown below. For example, in one embodiment, as shown in FIG. 7 and described in detail in the Examples contained herein, preparing compound 4 includes first combining TBAF with a solution of silyl ether, such as compound 3, in THF. Next, the mixture is stirred, diluted, and extracted. Following extraction, the organic extracts are washed, dried, filtered, and concentrated to provide compound 4.

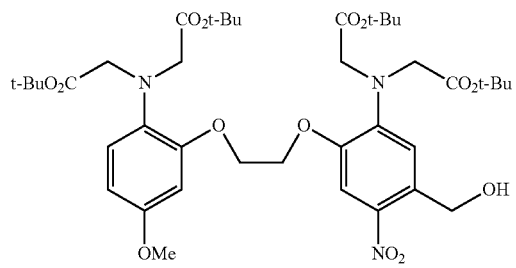

Figure 8:
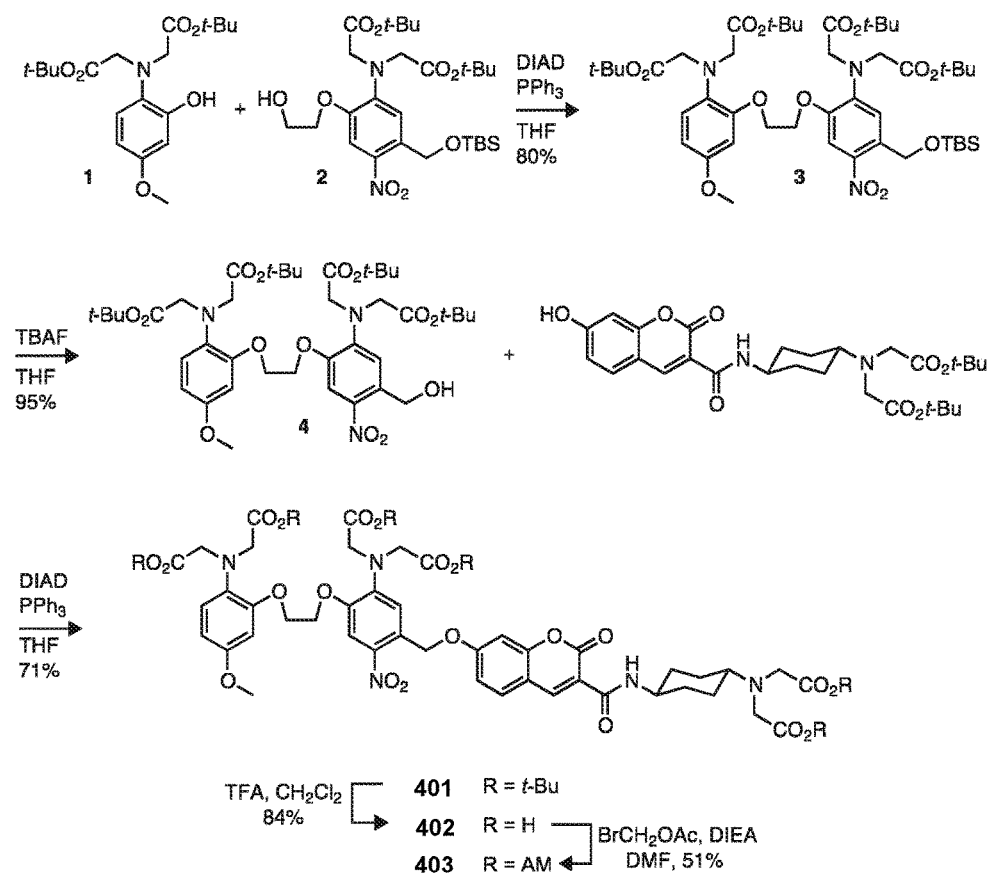
FIG. 8 includes a schematic representation of the synthesis of a compound according to an embodiment of the disclosure.
Figure 9:
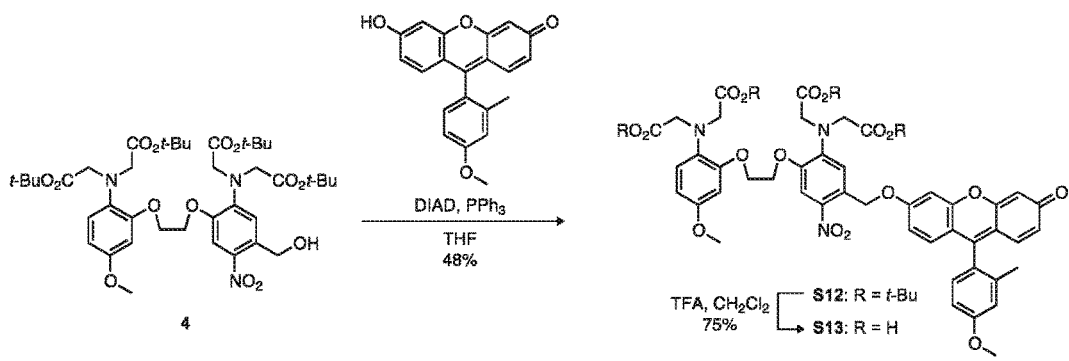
FIG. 9 includes a schematic representation of the synthesis of a compound according to an embodiment of the disclosure.

Additionally or alternatively, any suitable maskable molecule may be added to compound 4. Suitable maskable molecules include, but are not limited to, one or more of the molecules described in the Examples below. Methods of adding the maskable molecules are also described in detail in the Examples below (FIGS. 8 and 9).

Figure 10:
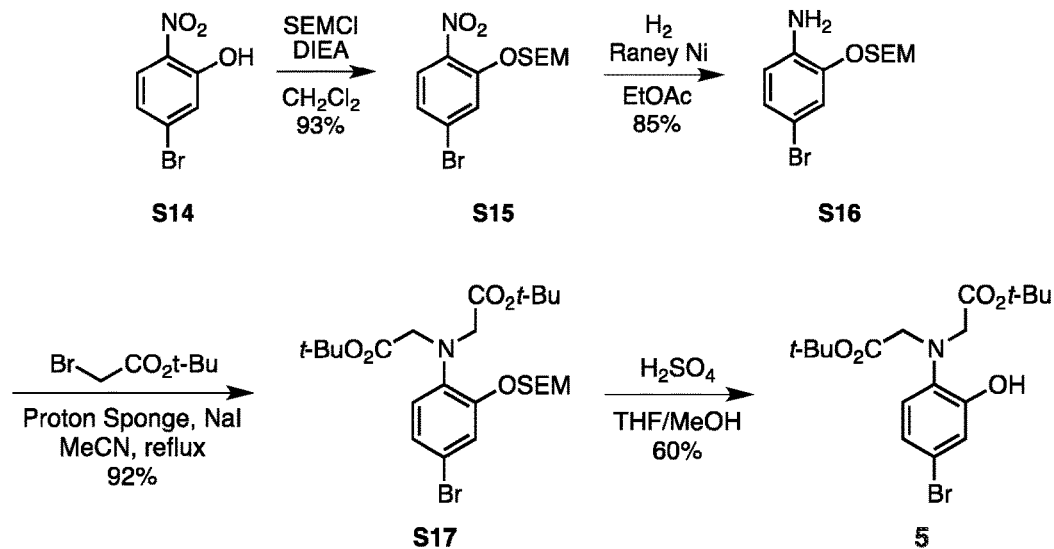
FIG. 10 includes a schematic representation of the synthesis of a compound according to an embodiment of the disclosure.

In some embodiments, preparing the present compounds includes preparing di-tert-butyl 2,2'-((4-bromo-2-hydroxyphenyl)azanediyl)diacetate (5), the structure of which is shown below. For example, in one embodiment, as shown in FIG. 10 and described in detail in the Examples contained herein, preparing compound 5 includes first adding 2-(trimethylsilyl)ethoxymethyl chloride to a solution of 5-bromo-2-nitrophenol (S14) and DIEA, then stirring, diluting, and extracting the mixture to form (2-((5-Bromo-2-nitrophenoxy)methoxy)ethyl)trimethylsilane (S15). Next, a solution of S15 in EtOAc is hydrogenated, concentrated, and purified to form 4-Bromo-2-((2-(trimethylsilyl)ethoxy)methoxy)aniline (S16), which is dissolved in MeCN and combined with tert-butyl bromoacetate, 1,8-bis(dimethylamino)naphthalene, and NaI to form di-tert-butyl 2,2'-((4-bromo-2-((2-(trimethylsilyl)ethoxy)methoxy)phenyl)azanediyl)diacetate (S17). A solution of S17 in 1:1 THF/MeOH is combined with $H_2SO_4$ in MeOH, the reaction is stirred and then quenched with $NaHCO_3$, and the resulting solution is diluted, extracted, washed, dried, filtered, and concentrated to form compound 5.

5

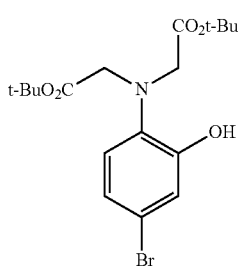

Figure 11:
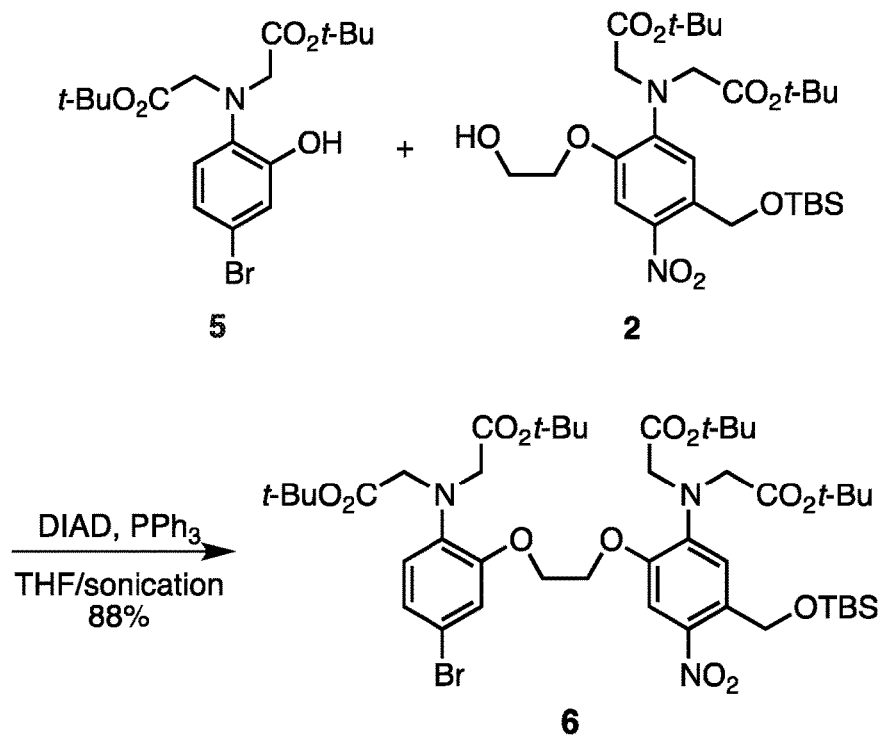
FIG. 11 includes a schematic representation of the synthesis of a compound according to an embodiment of the disclosure.

In some embodiments, preparing the present compounds includes preparing di-ter t-butyl 2,2'-((2-(2-(2-(bis(2-(tert-butoxy)-2-oxoethyl)amino)-4-(((tert-butyldimethylsilypoxy)methyl)-5-nitrophenoxy)ethoxy)-4-bromophenyl) azanediyl)diacetate (6), the structure of which is shown below. For example, in one embodiment, as shown in FIG. 11 and described in detail in the Examples contained herein, preparing compound 6 includes first charging a vial with a phenol, such as compound 5, compound 2, and $PPh_3$. Next, the vial is evacuated with nitrogen, THF is added, and the resulting mixture is sonicated. DIAD is then added and the reaction is further sonicated. Following the additional sonication, the solution is purified to provide compound 6.

6

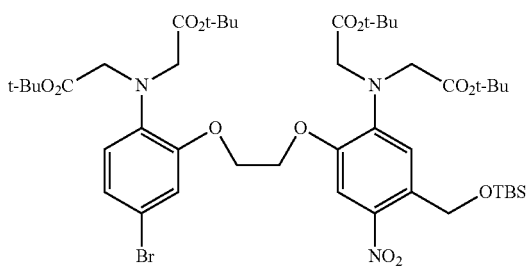

Figure 12:
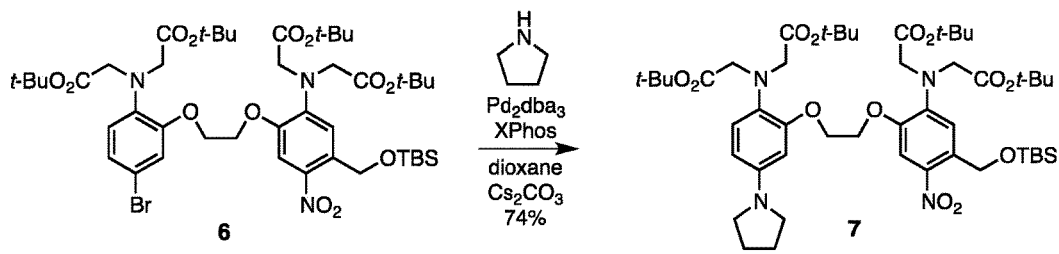
FIG. 12 includes a schematic representation of the synthesis of a compound according to an embodiment of the disclosure.

In some embodiments, preparing the present compounds includes preparing di-tert-butyl 2,2'-((2-(2-(2-(bis(2-(tert-butoxy)-2-oxoethyl)amino)-4-(((tert-butyldimethylsilyl) oxy)methyl)-5-nitrophenoxy)ethoxy)-4-(pyrrolidin-1-yl) phenyl)azanediyl)diacetate (7), the structure of which is shown below. For example, in one embodiment, as shown in FIG. 12 and described in detail in the Examples contained herein, preparing compound 7 includes first charging a vial with compound 6, XPhos, and $Cs_2CO_3$. Next, the vial is evacuated with nitrogen, dioxane is added, and the reaction is flushed again with nitrogen. Following the nitrogen flushing, pyrrolidine is added and the reaction is stirred, then cooled, filtered, and evaporated. The resulting residue is purified to provide compound 7.

7

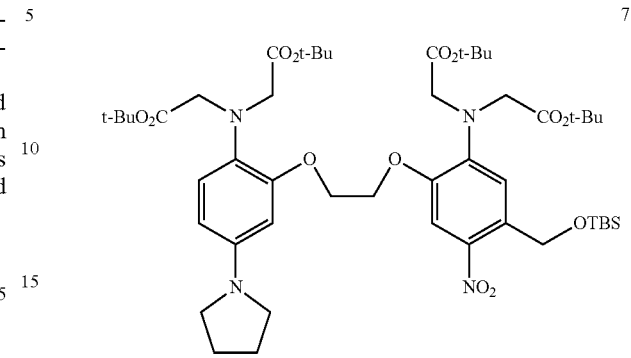

Figure 13:
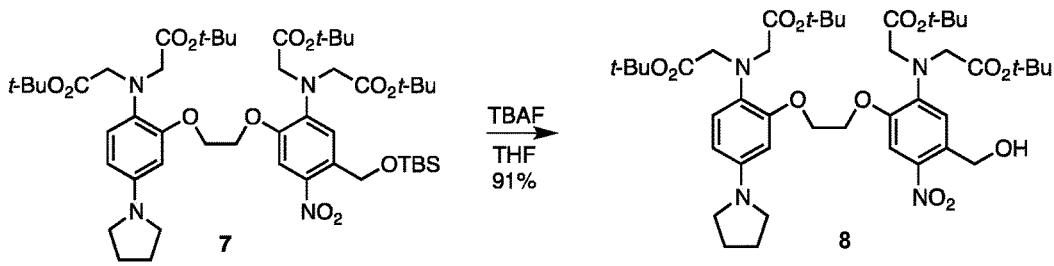
FIG. 13 includes a schematic representation of the synthesis of a compound according to an embodiment of the disclosure.

In some embodiments, preparing the present compounds includes preparing di-tert-butyl 2,2'-((2-(2-(2-(bis(2-(tert-butoxy)-2-oxoethyl)amino)-4-(hydroxymethyl)-5-nitrophenoxy)ethoxy)-4-(pyrrolidin-1-yl)phenyl)azanediyl)diacetate (8), the structure of which is shown below. For example, in one embodiment, as shown in FIG. 13 and described in detail in the Examples contained herein, preparing compound 8 includes first adding TBAF to a solution of silyl ether, such as compound 7, in THF. Next, the reaction is stirred, diluted, and extracted. The organic extracts are then washed, dried, filtered, and concentrated to provide compound 8.

8

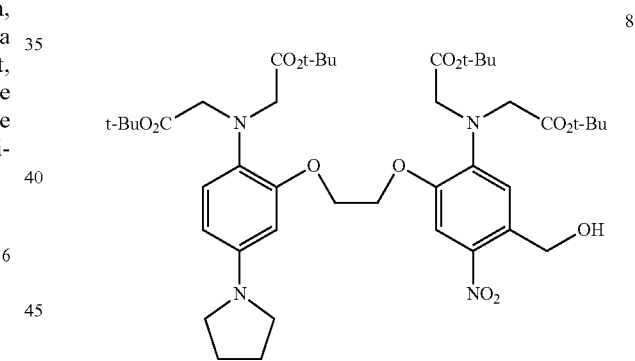

Figure 14:
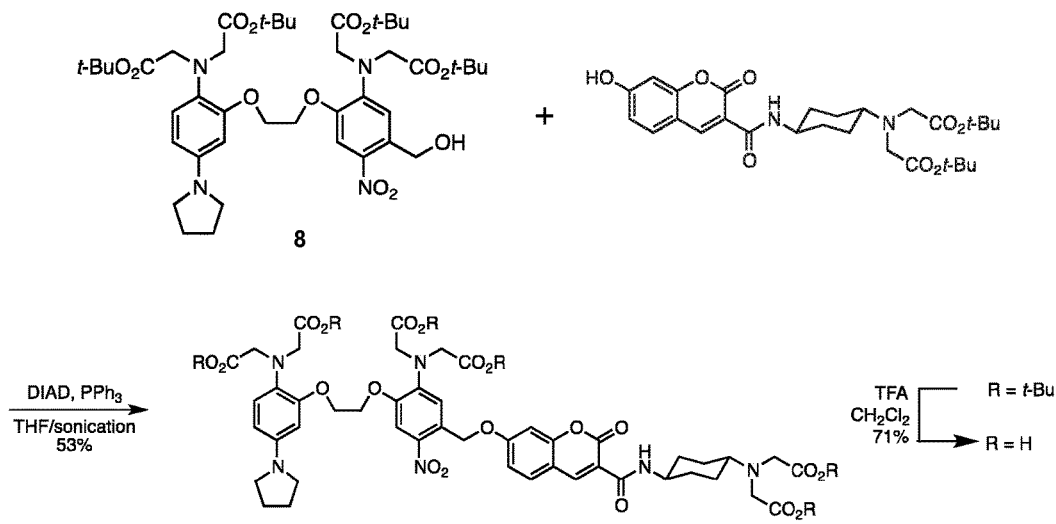
FIG. 14 includes a schematic representation of the synthesis of a compound according to an embodiment of the disclosure.

Additionally or alternatively, any suitable maskable molecule may be added to compound 8. Suitable maskable molecules include, but are not limited to, one or more of the molecules described in the Examples below. Methods of adding the maskable molecules are also described in detail in the Examples below (FIG. 14).

Figure 15:
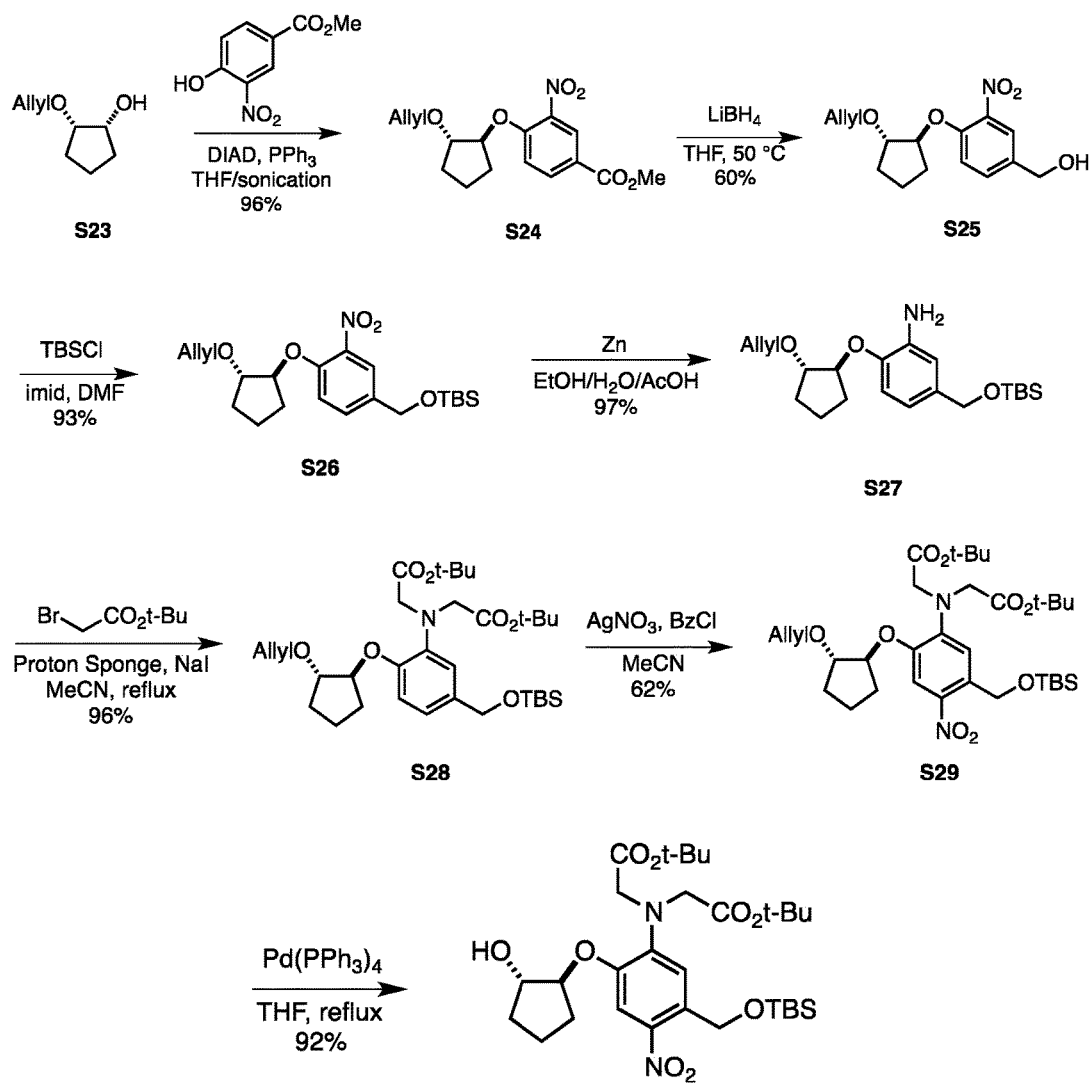
FIG. 15 includes a schematic representation of the synthesis of a compound according to an embodiment of the disclosure.

In some embodiments, preparing the present compounds includes preparing di-tert-butyl 2,2'-((5-(((tert-butyldimethylsilypoxy)methyl)-2-((trans-2-hydroxycyclopentyl)oxy)-4-nitrophenyl)azanediyl)diacetate (9), the structure of which is shown below. For example, in one embodiment, as shown in FIG. 15 and described in detail in the Examples contained herein, preparing compound 9 includes first charging a flask with methyl 4-hydroxy-3-nitrobenzoate, cis-2-(allyloxy)cyclopentanol (S23), and $PPh_3$, sealing and evacuating the flask with nitrogen, adding THF, and then sonicating the resulting mixture. Next, DIAD is added and after additional sonication the mixture is purified to provide Methyl 4-((trans-2-(allyloxy)cyclopentyl)oxy)-3-nitrobenzoate (S24). Lithium borohydride is added to S24 to form (4-((trans-2-(Allyloxy)cyclopentyl)oxy)-3-nitrophenyl)methanol (S25), which is combined with TBSCl and imidazole in DMF to provide ((4-((trans-2-(Allyloxy)cyclopentyl)oxy)-3-nitrobenzyl)oxy)(tert-butyl)dimethylsilane (S26). S26 is then combined with EtOH, AcOH, and zinc powder to provide 2-((trans-2-(Allyloxy)cyclopentyl)oxy)-5-(((tert-butyldimethylsilypoxy)methyl)aniline (S27), which is dissolved in MeCN and combined with tert-butyl bromoacetate, 1,8-bis(dimethylamino)naphthalene, and NaI to provide di-tert-butyl 2,2'-((2-((trans-2-(allyloxy)cyclopentyl)oxy)-5-(((tert-butyldimethylsilyl)oxy)methyl)phenyl)azanediyl)diacetate (S28). Di-tert-butyl 2,2'-((2-((trans-2-(allyloxy)cyclopentyl)oxy)-5-(((tert-butyldimethylsilypoxy)methyl)-4-nitrophenyl)azanediyl)diacetate (S29) is subsequently formed by taking up S28 in MeCN under nitrogen and adding AgNO₃ and benzoyl chloride. Finally, S29 is combined with 1,3-dimethylbarbituric acid and Pd(PPh₃)₄ in a round-bottomed flask equipped with a condenser to form compound 9.

stirring vigorously. Separate solutions of DIAD in toluene and PPh₃ in toluene are then simultaneously added to the heated reaction mixture, after which the mixture is cooled to room temperature and purified to provide TBS-protected Mitsunobu (S31). The intermediate S31 is dissolved in THF, TBAF is added, and the reaction is diluted with saturated NH₄Cl. After extraction with EtOAc, the combined organic extracts are washed, dried, filtered, concentrated, and purified to provide compound 10.

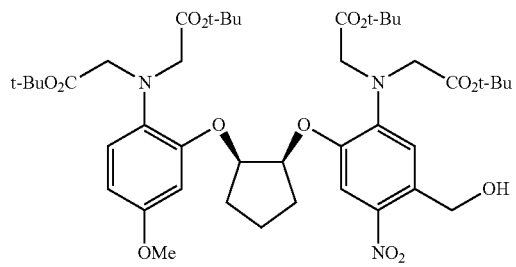

10

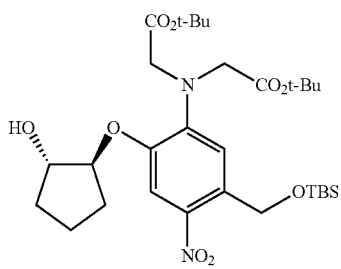

9

Figure 16:
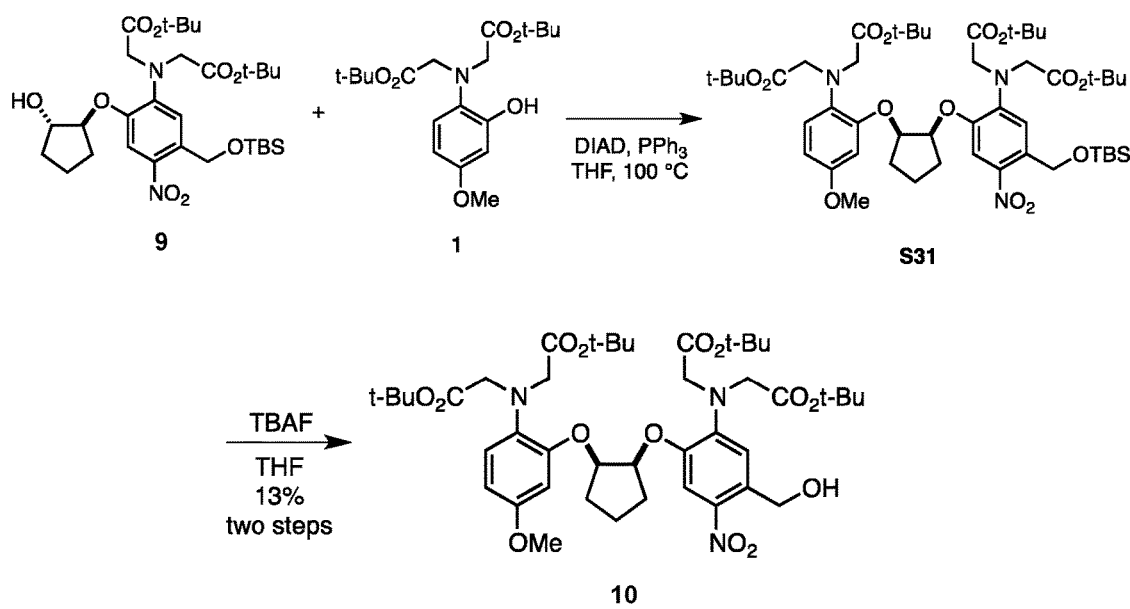
FIG. 16 includes a schematic representation of the synthesis of a compound according to an embodiment of the disclosure.
Figure 17:
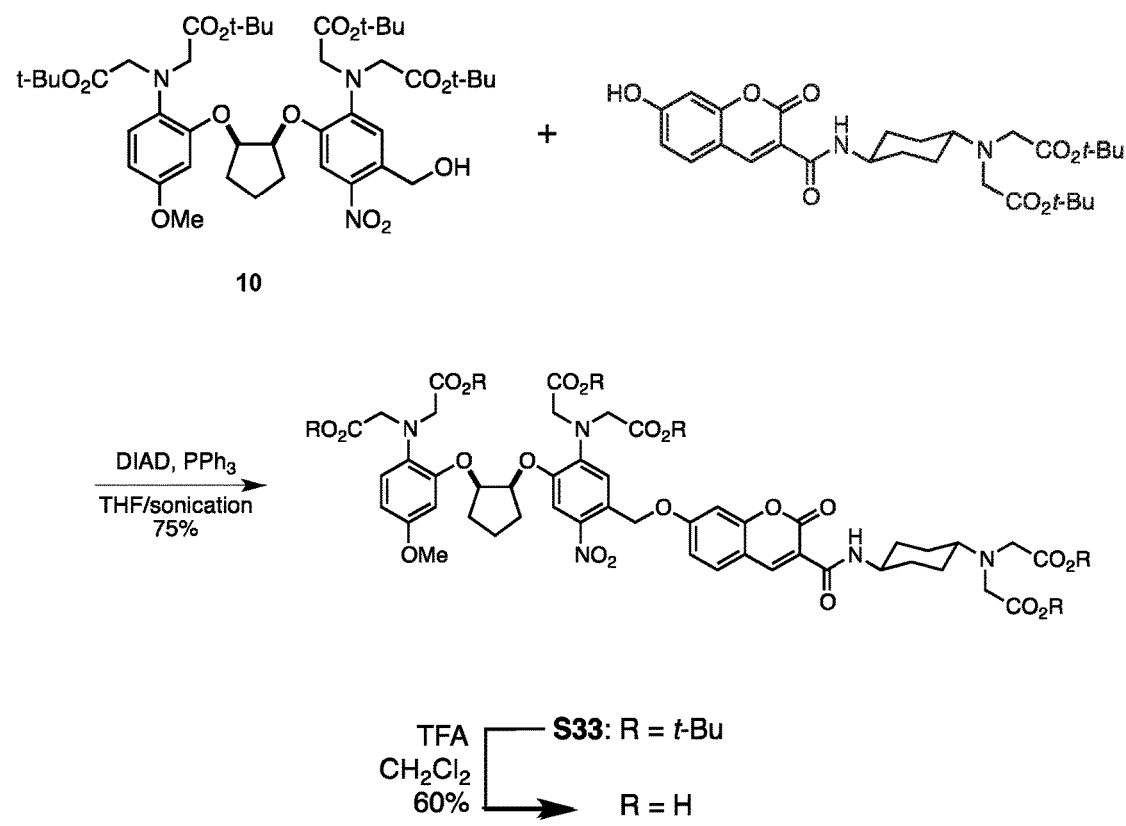
FIG. 17 includes a schematic representation of the synthesis of a cyclopentane-bridged calcium-dependent caged compound according to an embodiment of the disclosure.

In some embodiments, preparing the present compounds includes preparing di-tert-butyl 2,2'-((2-(((cis-2-(2-(bis(2-(tert-butoxy)-2-oxoethyl)amino)-4-(hydroxymethyl)-5-nitrophenoxy)cyclopentyl)oxy)-4-methoxyphenyl)azanediyl)diacetate (10), the structure of which is shown below. For example, in one embodiment, as shown in FIG. 16 and described in detail in the Examples contained herein, preparing compound 10 includes first charging a vial with an alcohol, such as compound 9, and compound 1. Next, the vial is sealed and evacuated with nitrogen, freshly degassed toluene is added, and the resulting mixture is heated while Additionally or alternatively, any suitable maskable molecule may be added to compound 10. Suitable maskable molecules include, but are not limited to, one or more of the molecules described in the Examples below. Methods of adding the maskable molecules are also described in detail in the Examples below (FIG. 17).

Figure 18:
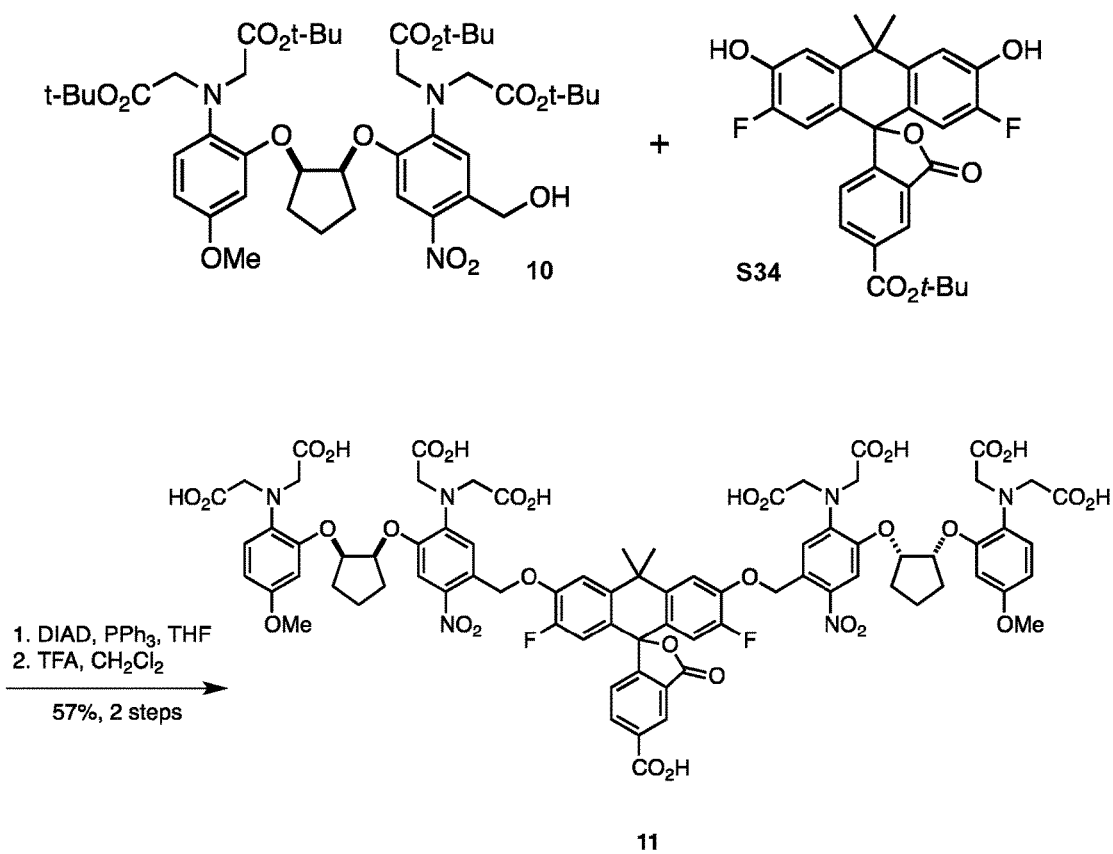
FIG. 18 includes a schematic representation of the synthesis of a two-cage system based on Virginia Orange.

In some embodiments, preparing the present compounds includes preparing a two-cage compound, such as, but not limited to, CpCDC₂—VO (11), the structure of which is shown below. For example, in one embodiment, as shown in FIG. 18 and described in detail in the Examples contained herein, preparing compound 11 includes first charging a vial with an alcohol, such as compound 10, 5-tert-butoxycarbonyl-2',7'-difluorocarbofluorescein (S34), and PPh₃. Next, the vial is evacuated with nitrogen, THF is added, DIAD is added, the reaction is stirred, and then the mixture is purified to provide CpCDC₂—VO (t-Bu)₉. TFA is subsequently added to a solution of the CpCDC₂—VO (t-Bu)₉ nonaester intermediate in CH₂Cl₂, after which toluene is added and the resulting mixture is concentrated to dryness. Finally, the resulting residue is purified to provide compound 11.

11

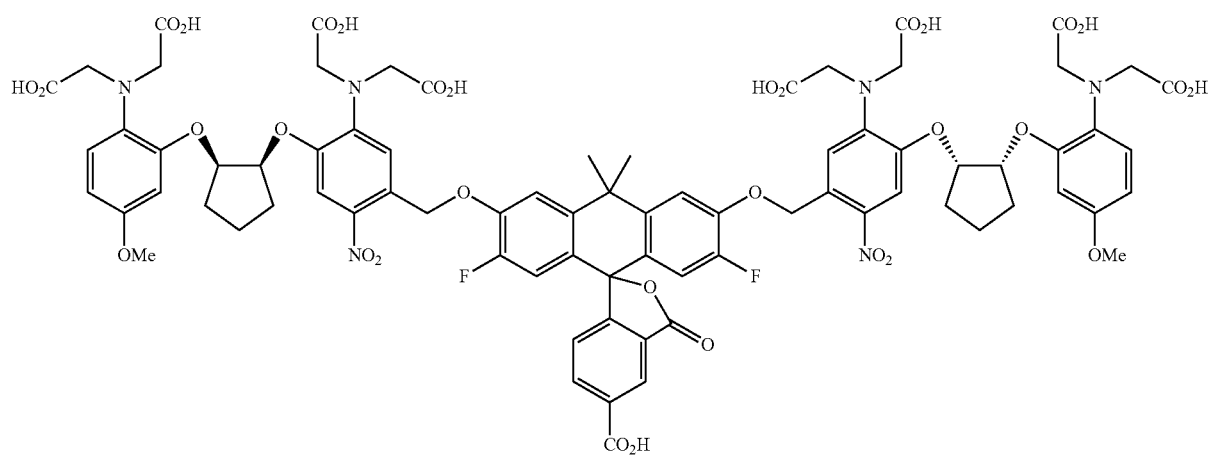

The presently-disclosed subject matter is further illustrated by the following specific but non-limiting examples. The following examples may include compilations of data that are representative of data gathered at various times during the course of development and experimentation related to the present invention.

EXAMPLES

Example 1

This Example describes the synthesis and characterization of an exemplary ion-activated photolabile compound of the presently-disclosed subject matter.

Synthesis and Characterization

The modular synthesis of a light-gated $Ca^{2+}$ chemodosimeter 401 is shown in FIG. 8. Phenol 1 and alcohol 2 were prepared through efficient 4- and 7-step syntheses, respectively (FIGS. 4 and 5). This convergent route includes a high-yielding Mitsunobu reaction between these atypical coupling partners to give bis-phenoxyethane 3. The electron-donating methoxy substituent on module 1 was incorporated to balance the requisite electron-withdrawing nitro group on component 2 and maintain a biologically relevant $K_d$. Compound 3 was selectively deprotected to give benzyl alcohol 4. Attachment of coumarin yielded 401, which could be deprotected to afford the light-gated $Ca^{2+}$ chemodosimeter 402.

Reactions were monitored by thin layer chromatography (TLC) on precoated TLC glass plates (silica gel 60 $F_{254}$, 250 μm thickness) or by LC/MS (4.6 mm×150 mm 5 μm C18 column; 5 μL injection; 10-95% or 50-95% $CH_3CN/H_2O$, linear gradient, with constant 0.1% v/v TFA additive; 20 min run; 1 mL/min flow; ESI; positive ion mode; UV detection at 254 nm). TLC chromatograms were visualized by UV illumination or developed with p-anisaldehyde, ceric ammonium molybdate, or $KMnO_4$ stain. Flash chromatography was performed on an automated purification system using pre-packed silica gel columns. High-resolution mass spectrometry was performed by the Mass Spectrometry Center in the Department of Medicinal Chemistry at the University of Washington.

NMR spectra were recorded on a 400 MHz spectrometer. $^1H$ and $^{13}C$ chemical shifts (δ) were referenced to TMS or residual solvent peaks, and $^{19}F$ chemical shifts (δ) were referenced to $CFCl_3$. Data for $^1H$ NMR spectra are reported as follows: chemical shift (δ ppm), multiplicity (s=singlet, d=doublet, t=triplet, q=quartet, dd=doublet of doublets, m=multiplet), coupling constant (Hz), integration. Data for $^{13}C$ NMR spectra are reported by chemical shift (δ ppm) with hydrogen multiplicity (C, CH, $CH_2$, $CH_3$) information obtained from DEPT spectra.

Figure 19A:
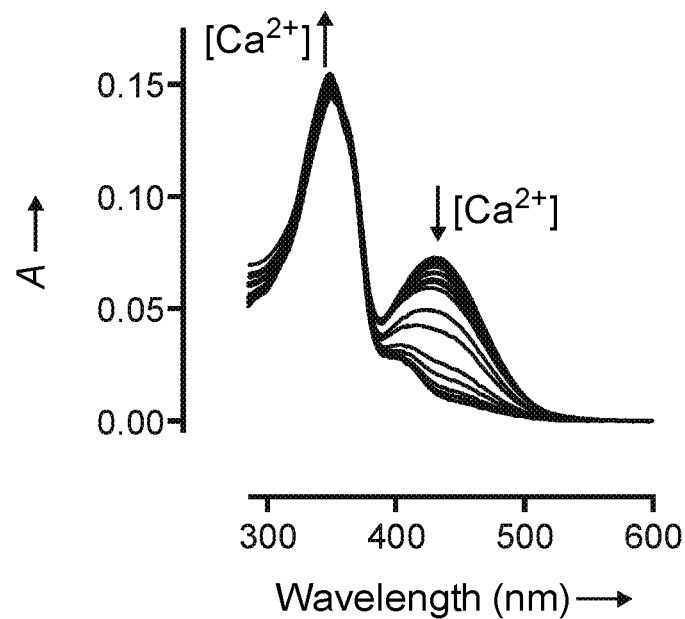
FIG. 19A includes a graph showing the absorbance spectra of 402 in aqueous buffers containing different $[Ca^{2+}]$.

The absorption spectrum of 402 was first examined in buffers containing varying $[Ca^{2+}]$ (FIG. 19A). The visible absorption at 430 nm shows a dramatic decrease as $[Ca^{2+}]$ increases. A small (<5%) but significant increase in absorption around 350 nm was also observed when calcium ion concentration is raised. However, the coumarin moiety dominates absorption in the UV with an extinction coefficient (e)=$2.4\times10^4$ $M^{-1}$ $cm^{-1}$ at 350 nm. These absorbance changes indicate that chelation of calcium causes a switch from the colored quinoid form to the UV-absorbing aromatic form (FIG. 3).

Figure 19B:
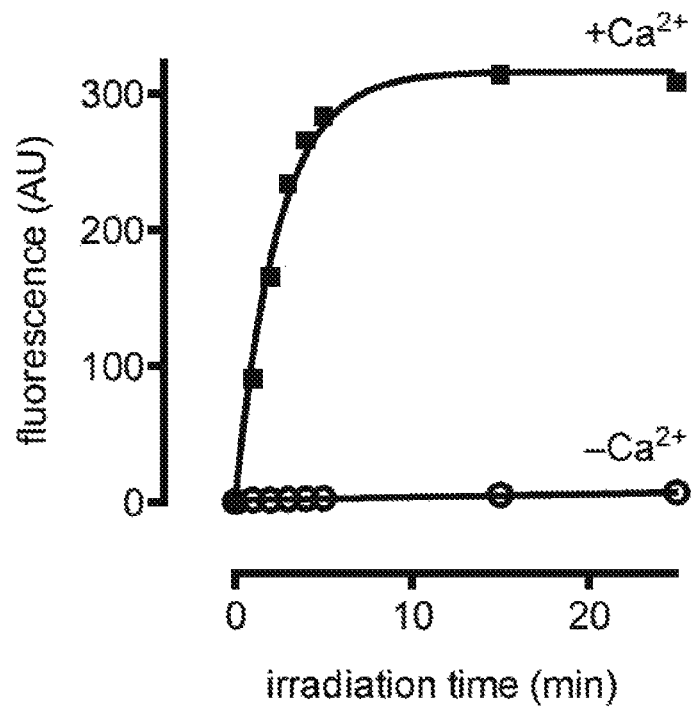
FIG. 19B includes a plot showing the fluorescence of released coumarin versus irradiation (365 nm) time of compound 402 in the presence (●; 10 mM $CaCl_2$) or absence (○; 10 mM EGTA) of $Ca^{2+}$.

Next, the $Ca^{2+}$-dependent uncaging and photochemical characteristics and the imaging capabilities of the ion-activated photolabile compounds were characterized. As shown in FIG. 19B, efficient photochemistry was observed only in the presence of calcium. The caged fluorophore 402 exhibited photochemical quantum yields (Φ) of 0.008% and 4.8% in the absence or presence of $Ca^{2+}$, respectively. This 600-fold enhancement in quantum yield surpasses the fluorescence increase observed with the known fluorescent calcium chemosensors.

Figure 19C:
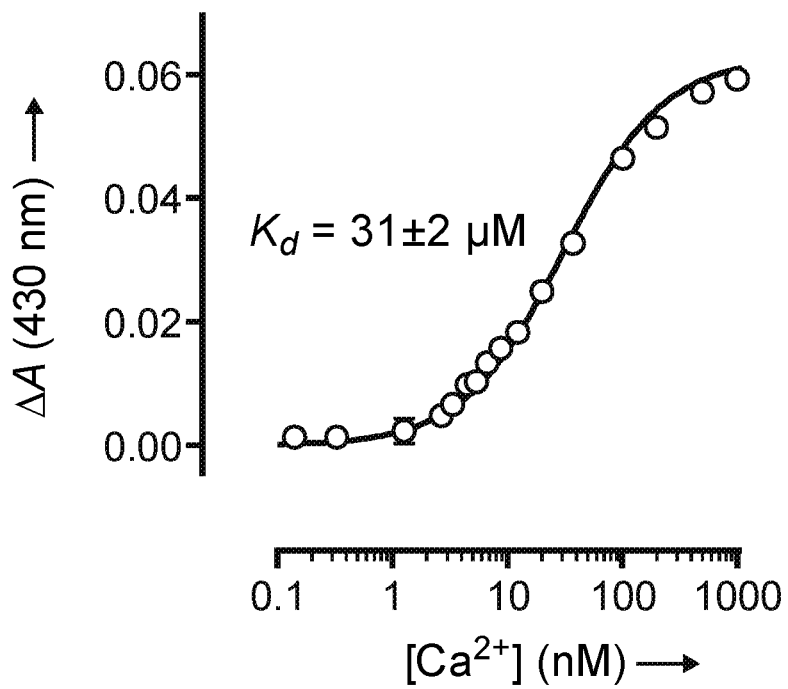
FIG. 19C includes a plot for determination of $K_d$ of compound 402 by the change in absorption at 430 nm (ΔA).
Figure 19D:
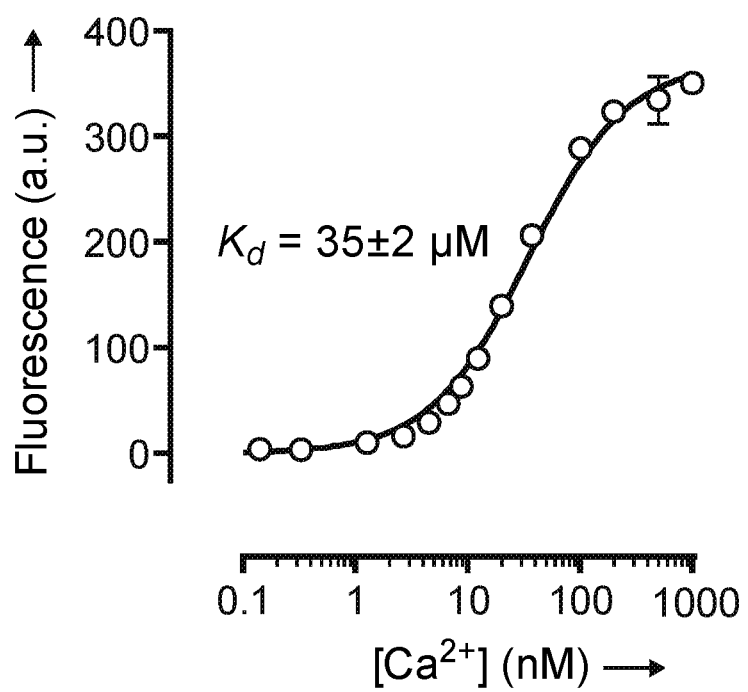
FIG. 19D includes a plot for determination of $K_d$ of compound 402 by the initial rate of fluorescence increase.
Figure 20A:
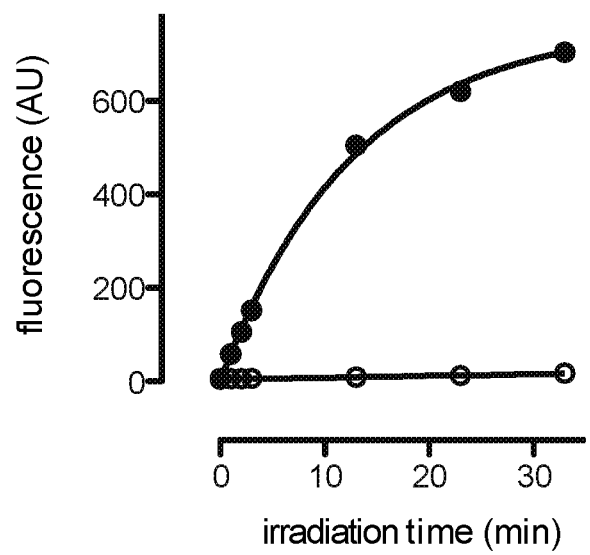
FIG. 20A includes a plot showing the fluorescence of released coumarin versus irradiation (365 nm) time of compound S13 in the presence (●; 10 mM $CaCl_2$) or absence (○; 10 mM EGTA) of $Ca^{2+}$.
Figure 20B:
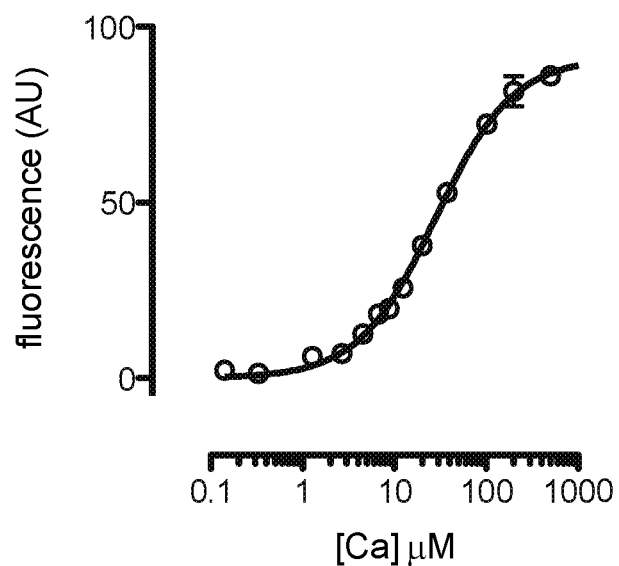
FIG. 20B includes a plot used to determine the $K_d$ of compound S13.

The calcium ion affinity of compound 402 was then characterized by measuring the change in absorption at 430 nm (FIG. 19C) or the initial rate of fluorescence from photoactivation as a function of $[Ca^{2+}]$ (FIG. 19D). The results showed $K_d$ values of 31 and 35 μM for the absorbance and fluorescence measurements, respectively, consistent with the nitro and methoxy substituents on the BAPTA ring. To show the generality of the presently-disclosed compounds, an analogous compound S13 was prepared that was based on Tokyo Green (FIG. 9) and observed $\Phi_{-Ca}$=0.011% and $\Phi_{+Ca}$=1.6% (150-fold enhancement) with similar affinity ($K_d$=28 μM; FIGS. 20A and 20B). Caged coumarins may exhibit higher photochemical quantum yields than other photoactivatable fluorophores due to efficient energy transfer from the coumarin moiety to the cage.

Figure 21A:
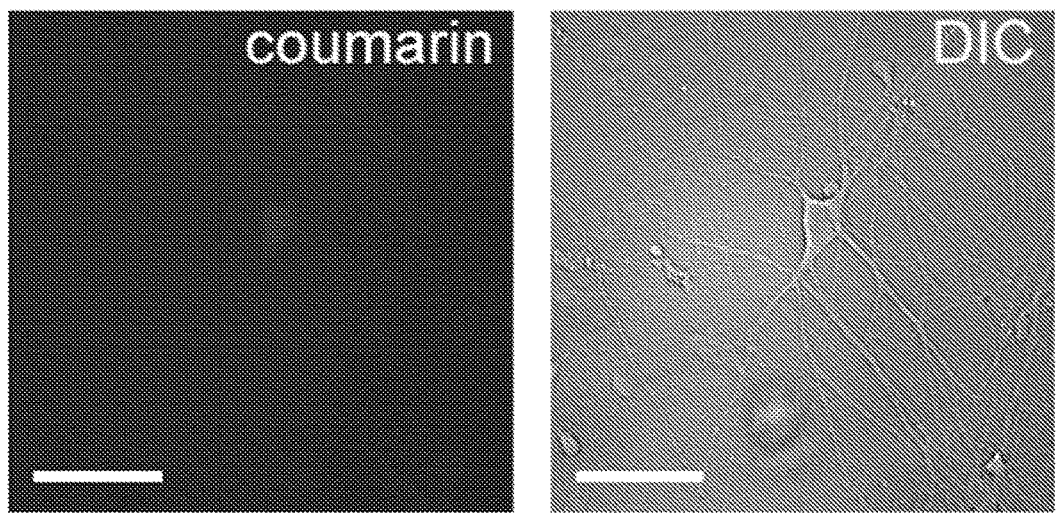
FIG. 21A includes images showing live cultured hippocampal neurons not treated with ionomycin that are incubated with AM ester 403 (10 μm) for 1 h and then illuminated with 365 nm light for 20 s. Scale bars: 100 μm.
Figure 21B:
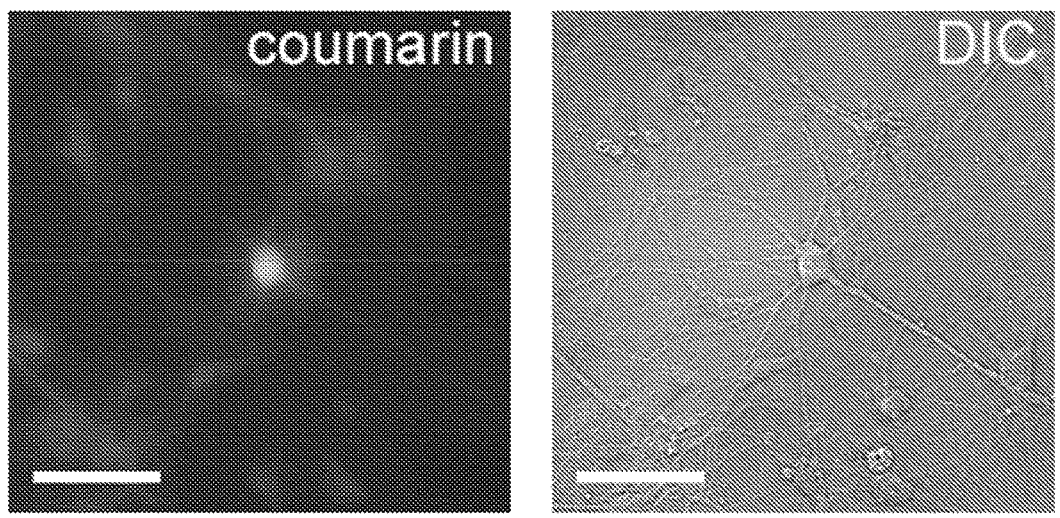
FIG. 21B includes images showing live cultured hippocampal neurons treated with ionomycin that are incubated with AM ester 403 (10 μm) for 1 h and then illuminated with 365 nm light for 20 s. Scale bars: 100 μm.
Figure 21C:
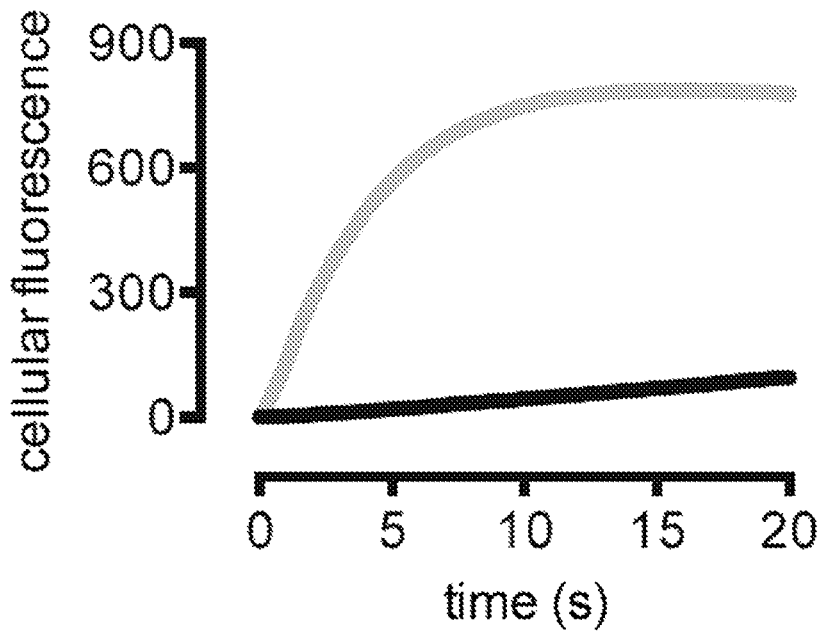
FIG. 21C includes a plot showing the quantification of cellular fluorescence versus irradiation time of the untreated neuron shown in FIG. 21A (black; k=0.0060 s$^{-1}$) and the ionomycin-treated neurons shown in FIG. 21B (cyan; k=0.240 s$^{-1}$).
Figure 22A:
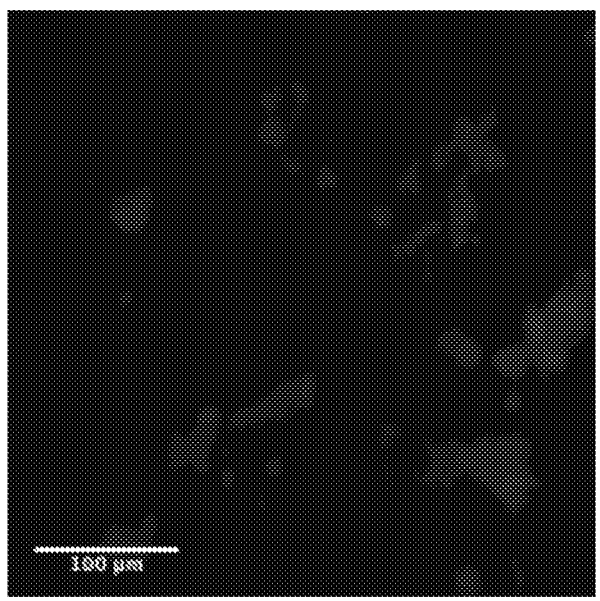
FIG. 22A includes images showing live cultured HEK 293T/17 untreated cells incubated with AM ester 403 (10 μM) for 1 h and then illuminated with 365 nm light for 20 s.
Figure 22B:
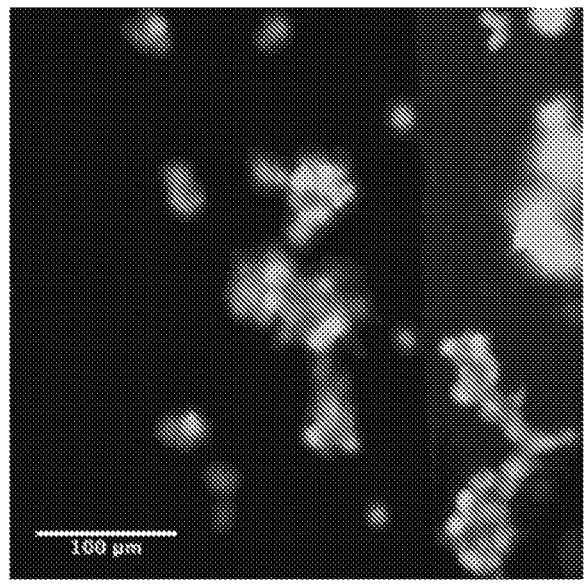
FIG. 22B includes images showing live cultured HEK 293T/17 cells that were treated with ionomycin, incubated with AM ester 403 (10 μM) for 1 h, and then illuminated with 365 nm light for 20 s.
Figure 22C:
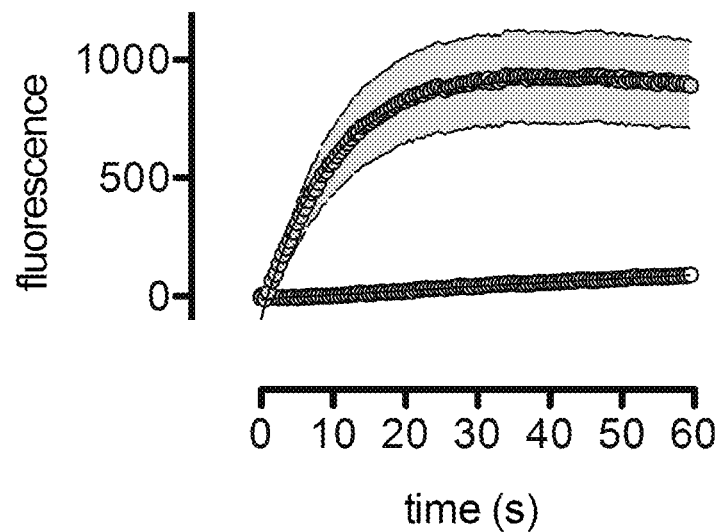
FIG. 22C includes a plot showing cellular fluorescence versus irradiation time of untreated cells in A (black) and ionomycin-treated cells in B (gray). Shading shows ±standard error (n=11).

The utility of the embodied system was then observed in a cellular context. The hexa-acetoxymethyl (AM) ester 403 of compound 402 was prepared (FIG. 8). This membrane-permeant compound enabled loading of cultured hippocampal neurons with the light-gated chemodosimeter. The overlap of the photouncaging wavelength (λ=351 nm) and the excitation spectra ($\lambda_{max}$=402 nm) of the coumarin allowed simultaneous imaging and activation with a single light source centered at 365 nm. Illumination of control cells did not elicit significant fluorescence increase (FIG. 21A). In contrast, cells pretreated with ionomycin to raise intracellular calcium levels showed a 40-fold increase in the accumulation of cellular fluorescence (FIGS. 21B and 21C). Similar results were observed in HEK cells (FIGS. 22A-22C).

Figure 21D:
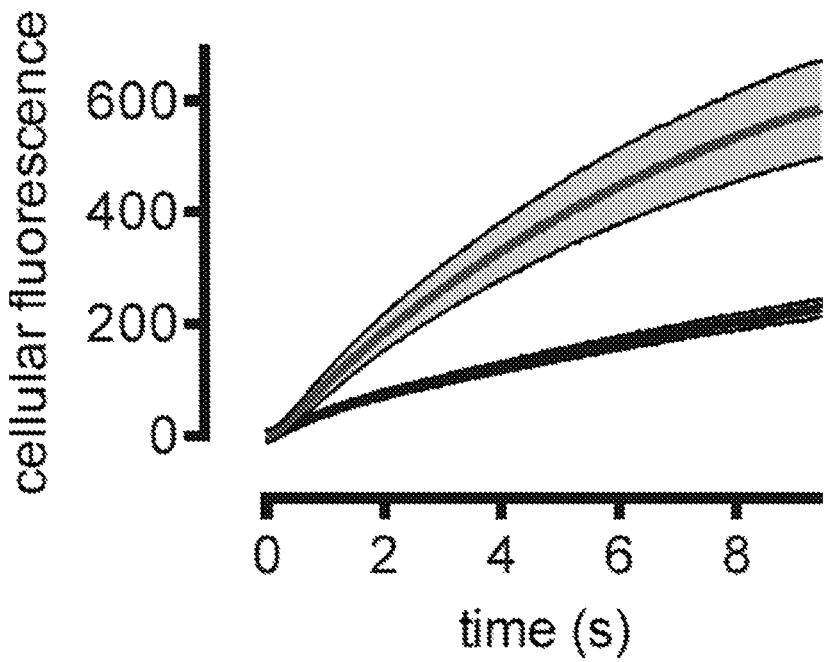
FIG. 21D includes a plot of increase in cellular fluorescence versus irradiation time of cultured neurons without electrical stimulation (black; k=0.0325 s$^{-1}$) and with stimulation (gray; k=0.133 s$^{-1}$). Shading shows ±standard error (n=20).

The present compound was then utilized to measure calcium ion changes in neurons evoked by electrical activity. Low-affinity reversible $Ca^{2+}$ indicators are advantageous for use in biological systems as their low buffering capacity preserves native calcium ion dynamics. Nevertheless, poor signal-to-background ratios of such indicators may restricts their utility to subcellular compartments undergoing extremely high calcium flux (e.g., dendritic spines). The present compounds had a permanent signal that permitted measurement of modest changes in cellular calcium levels using a nonperturbative, low affinity probe. Cells were incubated with AM ester 403 and subjected to the photoactivation imaging protocol. In one population of cells neuronal action potential firing was elicited by field stimulation at 80 Hz. As shown in FIG. 21D, this electrical stimulation caused a 4-fold rate increase in cellular fluorescence relative to unstimulated cells, ultimately giving a permanent 200% increase in cellular fluorescence.

Methods

General.

Commercial reagents were obtained from reputable suppliers and used as received. All solvents were purchased in septum-sealed bottles stored under an inert atmosphere. All reactions were sealed with septa through which a nitrogen atmosphere was introduced unless otherwise noted. Reactions were conducted in round-bottomed flasks or septum-capped crimp-top vials containing Teflon-coated magnetic stir bars. Heating of reactions was accomplished with a silicon oil bath or an aluminum reaction block on top of a stirring hotplate equipped with an electronic contact thermometer to maintain the indicated temperatures.

All measurements were taken at ambient temperature (23±2° C.). Fluorogenic molecules were prepared as stock solutions in DMSO and diluted such that the DMSO concentration did not exceed 1% v/v. Spectroscopy was performed using 1-cm path length quartz or polymethacrylate cuvettes (Starna or Fisher). Absorption measurements were recorded on a Cary Model 100 spectrometer (Varian). Fluorescence measurements spectra were recorded on a Cary Eclipse fluorometer (Varian). Buffer pH was adjusted with KOH. Curve fitting was accomplished with GraphPad Prism 5.

Determination of Photochemical Quantum Yield.

Photochemistry was performed in 1-cm path length/3.5 mL quartz cuvettes (Starna) in a Luzchem LZC 4V photoreactor equipped with 365 nm UV lamps, a carousel, and a timer. The irradiation was determined by potassium ferrioxalate actinometry.[3] A solution of 60 mM $K_3Fe(C_2O_4)_3$ was irradiated using the photoreactor setup. Released $Fe^{2+}$ was determined by complexometry with 1,10 phenanthroline. Using the known photochemical quantum yield of this process, we determined the photon flux (I)=$3.57 \times 10^7$ ein/min·cm². Samples (10 μM, 3.5 mL) were irradiated in either zero calcium buffer (30 mM MOPS pH 7.2, 10 mM EGTA, 100 mM KCl) or calcium-containing buffer (30 mM MOPS pH 7.2, 10 mM $CaCl_2$, 100 mM KCl) and a small aliquot (30 μL) was removed and diluted 100-fold in matching buffer. The fluorescence of these samples was then measured (coumarin 402: $\lambda_{ex}/\lambda_{em}$=402/447 nm; Tokyo Green compound S13: $\lambda_{ex}/\lambda_{em}$=496/520 nm). The quantum yield (Φ, mol/ein) was determined by fitting a plot of fluorescence vs. irradiation time to a one-phase association described by equation 1:

$$F_t = F_{max} - F_{max}(e^{-I\sigma\Phi t}) \quad (1)$$

where $F_{max}$=maximal fluorescence, t=time (min), $F_t$=fluorescence at time t, I=irradiation (ein/min·cm²), and σ=decadic extinction coefficient (cm²/mol; 1000-fold higher than the value with units of $M^{-1}$ $cm^{-1}$ based on cuvette geometry). For compound 402 we determined Φ=4.8±0.2% (mean±SE) in the presence of 10 mM $Ca^{2+}$ and Φ=0.0079±0.0003% in the presence of 10 mM EGTA (FIG. 19B). For compound S13 we found Φ=1.63±0.05% in the presence of 10 mM $Ca^{2+}$ and Φ=0.0110±0.0004% in the presence of 10 mM EGTA (FIG. 20A).

Determination of $K_d$.

For $[Ca^{2+}]$<40 μM, the free calcium concentration was controlled by a commercial EGTA buffer system (Invitrogen). Briefly, different proportions of EGTA buffer (30 mM MOPS pH 7.2, 10 mM EGTA, 100 mM KCl) or Ca.EGTA buffer (30 mM MOPS pH 7.2, 10 mM Ca.EGTA, 100 mM KCl) were mixed to give solutions with different free $[Ca^{2+}]$ based on a $K_d$ of Ca.EGTA=141.5 nM (value from maxchelator.stanford.edu at 25° C. 0.1 M ionic strength, pH 7.2). For $[Ca^{2+}]$>40 μM, buffers were prepared with 1 mM EGTA and excess $CaCl_2$ in 30 mM MOPS pH 7.2 and 100 mM KCl. Different buffer solutions containing 100 nM of 402 or S13 were irradiated in clean glass vials for 1 min using the photoreactor setup described above. The samples were then transferred to a black, clear bottom, 96-well polystyrene microplate with a nonbinding surface coating (Corning). Fluorescence was read from the bottom on a FlexStation3 fluorescence microplate reader (Molecular Devices; for coumarin 402: $\lambda_{ex}/\lambda_{em}$=402/447 nm; for Tokyo Green compound S13: $\lambda_{ex}/\lambda_{em}$=496/520 nm). The plot of fluorescence vs. $[Ca^{2+}]$ was fit to one site-specific binding curve to determine the $K_d$. Found: 28.3±0.6 μM (±SE) for 402 and 28.0±0.8 μM for S13.

Cell Culture.

HEK293T/17 cells (ATCC) were cultured according to instructions in poly-D-lysine-coated 24-well CellBind plates (Corning) in Dulbecco's modified eagle medium (DMEM; Invitrogen) supplemented with 10% v/v fetal bovine serum (FBS; Invitrogen) and maintained at 37° C. in a humidified 5% $CO_2$ v/v environment. Primary rat hippocampal neurons were prepared and cultured as described previously. Imaging buffer for HEK293T/17 cells consisted of Dulbecco's phosphate buffered saline (DPBS; Invitrogen). Imaging buffer for cultured neurons consisted of: 145 mM NaCl, 2.5 KCl, 10 mM glucose, 10 mM HEPES pH 7.4, 2 mM $CaCl_2$, and 1 mM $MgCl_2$. To load cells with the dosimeter, a stock solution of 403 (1 mM) in DMSO containing 10% w/v Pluronic F-127 (Sigma) was added to a final concentration of 10 μM in imaging buffer. Cells were incubated in this solution for 1 h at 37° C., after which the cells were washed with imaging buffer (3×) and imaged. The final imaging buffer wash for cultured neurons additionally contained pharmacological agents (10 μM CNQX, 10 μM (R)-CPP, 10 μM gabazine, and 1 mM (S)-MCPG; Tocris) to block spontaneous cellular activity.

Live Cell Wide-Field Fluorescence Microscopy.

Cells were imaged on a Olympus IX-81 microscope using a 10× or 20× objective and a DAPI filter set (Semrock DAPI-5060C-000; excitation: 352-402 nm, dichroic cutoff: 409 nm, emission: 417-477 nm) filtering a mercury arc lamp. Excitation/photoactivation light was attenuated using a neutral density filter giving a light intensity of 60 mW/cm². To raise intracellular calcium ion levels (FIGS. 19B, 21B, and 22B), cells were incubated with 10 μM ionomycin (Sigma) and 4 mM $CaCl_2$ for 2 min prior to imaging.

Light-Gated Integration of $Ca^{2+}$ Evoked by Electrical Stimulation (FIG. 21D).

Cultured neurons loaded with compound 403 were stimulated electrically to induce action potential firing at 80 Hz for one second prior to and during illumination with excitation/photoactivation light. A Grass S48 Stimulator (Grass Technologies) was used with a custom-built platinum wire field stimulation electrode.

Modeling of the Rate of Uncaging in Stimulated and Unstimulated Cells.

The expected release rate of compound 402 under different $Ca^{2+}$ concentrations can be calculated using equation 2:

$$k = I(\sigma_f C_f \Phi_f + \sigma_b C_b \Phi_b) \quad (2)$$

where k=the rate of photochemical reaction, I=irradiation intensity (ein/min·cm²), σ=the decadic extinction coefficient (in units of cm²/mol; 1000-fold higher than the e value with units of $M^1$ $cm^1$ based on cuvette geometry), C=the concentration of indicator, Φ=the photochemical quantum yield of the cage, and subscripts b and f indicate $Ca^{2+}$-bound and $Ca^{2+}$-free, respectively. To find $C_b$ and $C_f$ we use the following Equations S1-S3 where the $[Ca^{2+}]_t$ is the total calcium ion concentration and $[Ca^{2+}]_b$ and $[Ca^{2+}]_f$ are the concentrations of bound and free calcium ion, respectively:

$$K_d = \frac{C_f \times [Ca^{2+}]_f}{C_b} \quad (S1)$$

$$C_f = C_t - C_b \quad (S2)$$

$$[Ca^{2+}]_f = [Ca^{2+}]_t - C_b \quad (S3)$$

Putting everything in terms of bound indicator ($C_b$) gives Equation S4

$$K_d = \frac{(C_t - C_b) \times ([Ca^{2+}]_t - C_b)}{C_b} \quad (S4)$$

Rearrange and simplify to yield Equation S5:

$$C_b^2 - C_b([Ca^{2+}]_t + C_t + K_d) - (C_t \times [Ca^{2+}]_t) = 0 \quad (S5)$$

Solving the quadratic equation gives Equation 3:

$$C_b = \frac{(C_t + [Ca^{2+}]_t + K_d) - \sqrt{(C_t + [Ca^{2+}]_t + K_d)^2 - 4(C_t \times [Ca^{2+}]_t)}}{2} \quad (3)$$

where $C_t$=total concentration of indicator, $[Ca^{2+}]$ is the calcium ion concentration in the cells, and $K_d$ is the dissociation constant of the $Ca^{2+}$-sensitive cage indicator.

Figure 23A:
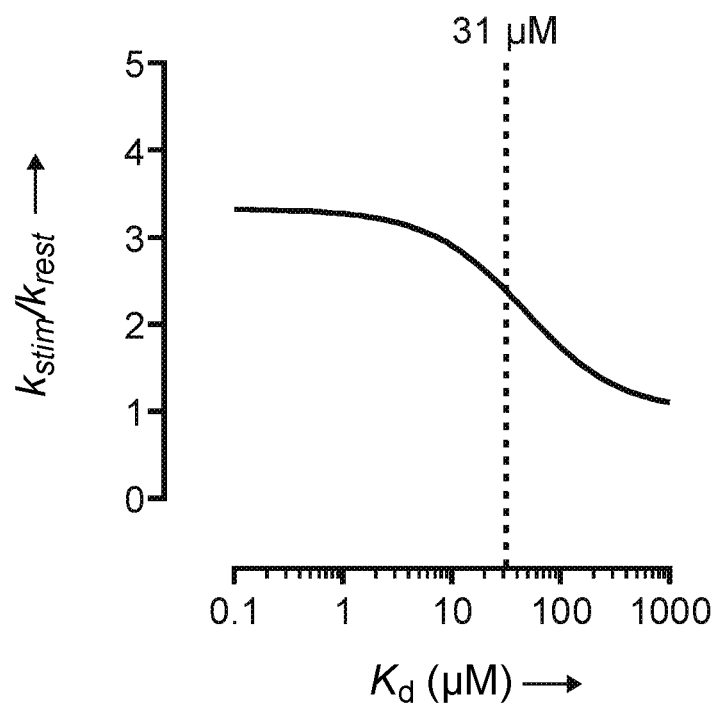
FIG. 23A includes a plot showing theoretical uncaging contrast ($k_{stim}/k_{rest}$) as a function of $K_d$. Dashed line shows $K_d$ for compound 402 (28 µM).
Figure 23B:
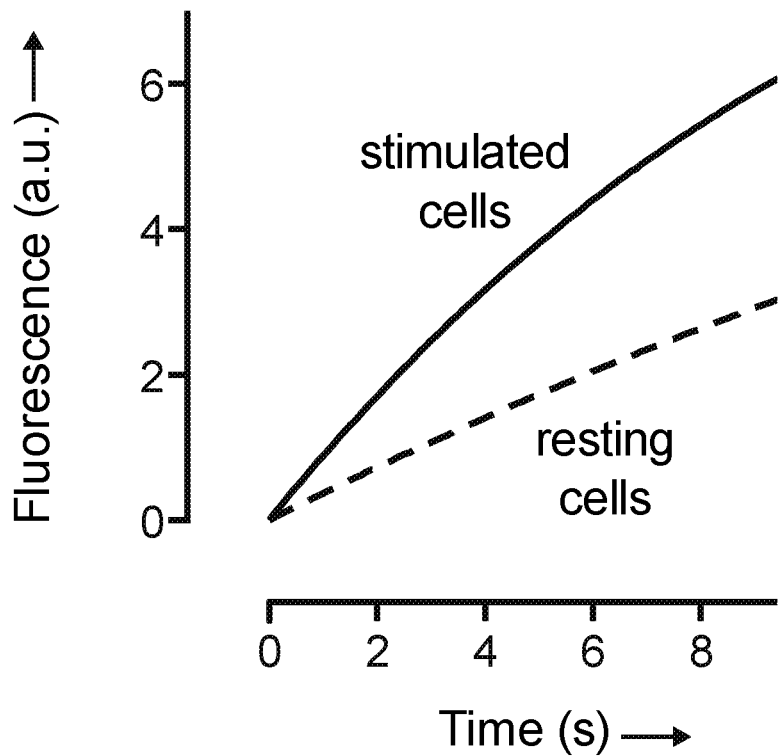
FIG. 23B includes a plot showing theoretical rate of fluorescence increase using probe 402 in cells, assuming an average [$Ca^{2+}$] of 245 nM and 62 nM in stimulated and resting cells, respectively.

The concentration of free indicator ($C_f$) can be calculated from $C_t$ and $C_b$. The rate of uncaging was modeled first in stimulated cells relative to the rate in resting cells (FIG. 23A; $k_{stim}/k_{rest}$, the uncaging contrast) as a function of $K_d$, assuming average $[Ca^{2+}]$ of 245 nM and 62 nM in stimulated and resting cells, respectively,[24] an indicator concentration ($C_t$) of 10 μM (FIG. 23A) and an irradiation time of 5 s. Without wishing to be bound by theory, under these conditions, the maximum achievable contrast is predicted to be 330%. This value is largely dictated by the ~4-fold increase in $Ca^{2+}$ concentration and non-cooperative binding of BAPTA (Hill coefficient=1). Moreover, this mathematical modeling predicts that decreasing the $K_d$ has only a modest effect on contrast; compound 402 ($K_d$=31) should still give a $k_{stim}/k_{rest}$ of 240% (FIG. 23A) resulting in a clear delineation of stimulated and unstimulated cells (FIG. 23B). To model the increase in fluorescence over time in simulated and resting cells the same parameters as above were assumed and a light intensity (I) of $1.67 \times 10^4$ ein/s·cm², correcting for the depletion of indicator concentration (C) during the course of the reaction.

Example 2

Figure 24A:
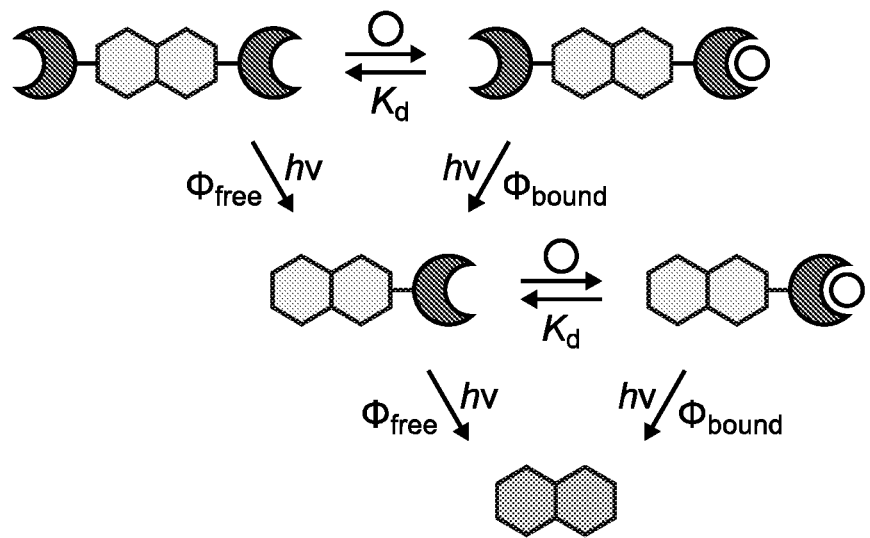
FIG. 24A is a schematic illustration showing the equilibria of a two-cage system.
Figure 24B:
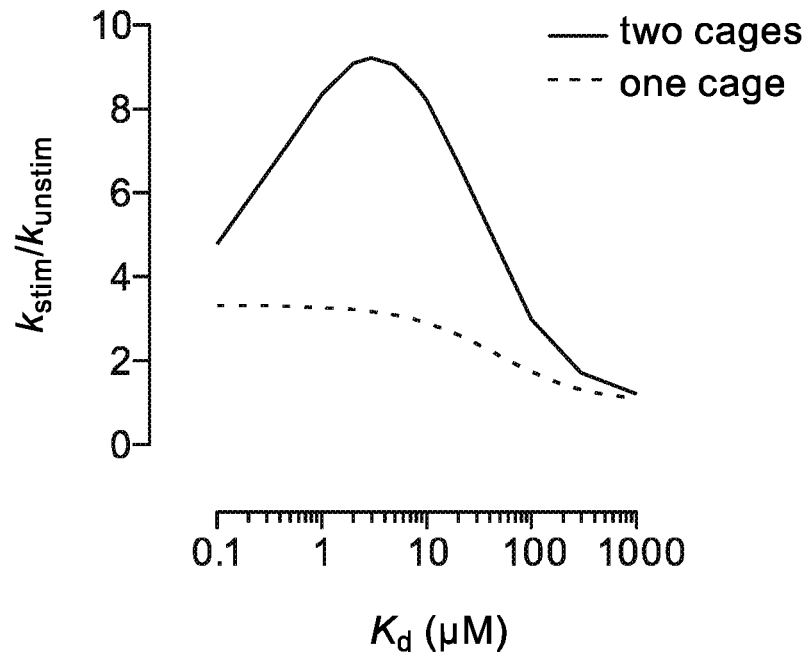
FIG. 24B includes a plot showing the theoretical uncaging contrast ($k_{stim}/k_{rest}$) as a function of $K_d$. Dashed line shows model for one-cage system, solid line shows model for two-cage system.

This Example considers systems with two calcium-dependent cages per fluorophore, where both must be removed to obtain and fluorescence increase (FIG. 24A). The predicted photochemical contrast ($k_{stim}/k_{unstim}$) was plotted using the assumptions above (FIG. 23A). The model predicted that a two-cage system would show improved performance with optimal performance at $K_d \approx 5$ μM (FIG. 24B).

Figure 24C:
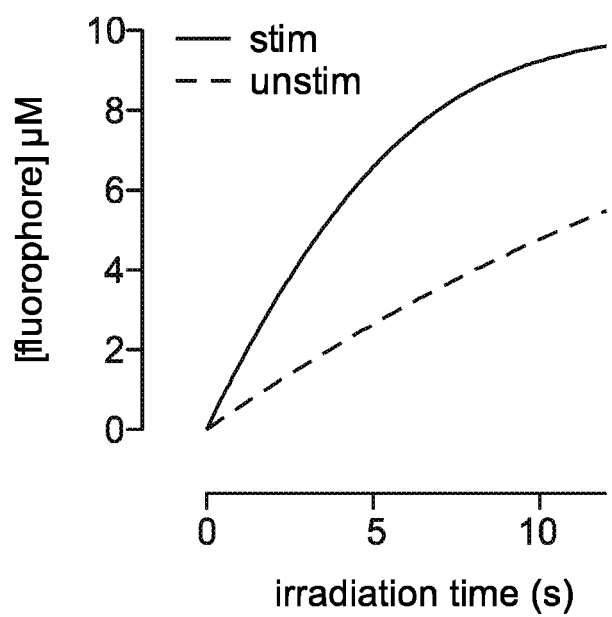
FIG. 24C includes a plot showing theoretical rate of fluorescence increase using a single-cage probe in cells, assuming a $K_d$ of 8 µM and an average [$Ca^{2+}$] of 245 nM and 62 nM in stimulated and resting cells, respectively.
Figure 24D:
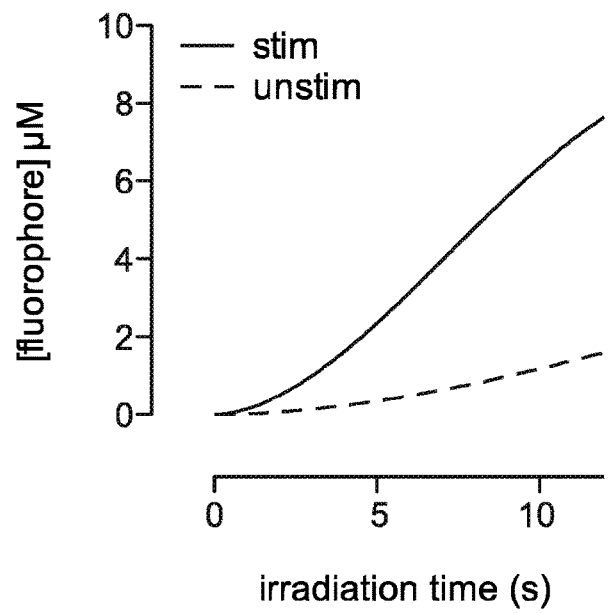
FIG. 24D includes a plot showing theoretical rate of fluorescence increase using a dual-cage probe in cells, assuming an $K_d$ of 8 µM and an average [$Ca^{2+}$] of 245 nM and 62 nM in stimulated and resting cells, respectively.
Figure 24E:
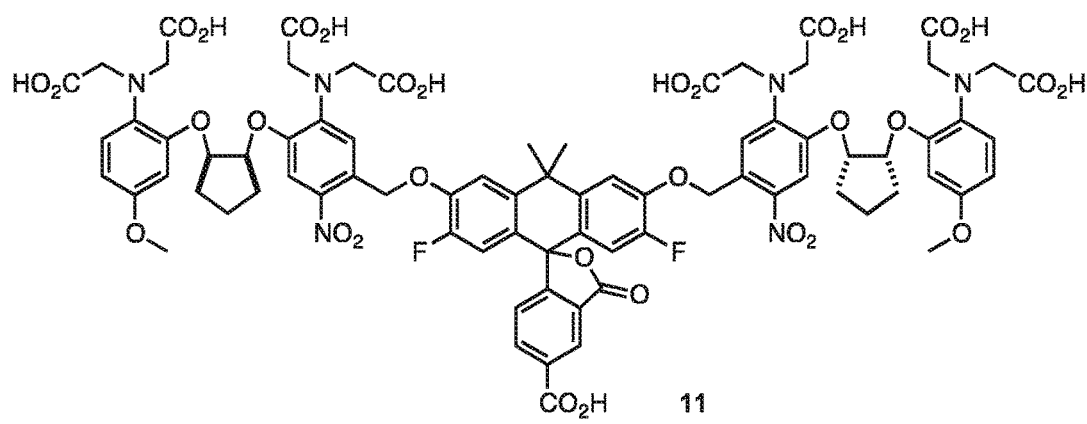
FIG. 24E illustrates the chemical structure of a dual-cage compound 11 based on Virginia Orange.
Figure 24F:
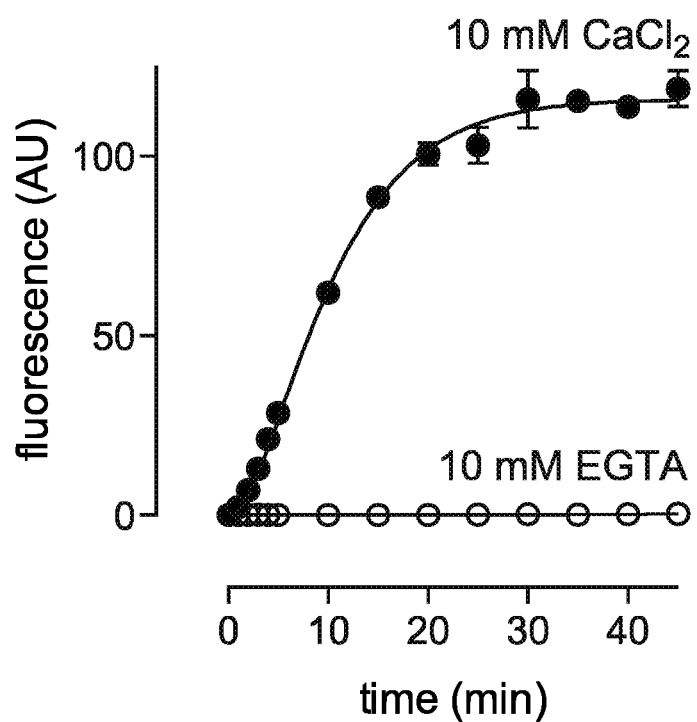
FIG. 24F includes a plot showing fluorescence (AU) of released coumarin versus irradiation (365 nm) of 11 in the presence (●; 10 mM $CaCl_2$) or absence (○; 10 mM EGTA) of $Ca^{2+}$.

In view thereof, one or more of the cages described herein were modified through at least one of two strategies. First, the methoxy substituent in compound 402 was replaced with a more electron-donating pyrrolidine group to make the compound of FIG. 14, where R=H. Surprisingly, this modification did not increase, probably due to competing protonation of this more basic motif in aqueous solution. Another modification to increase calcium affinity in BAPTA chelators includes cyclization of the ethylene glycol bridge, as in the cyclopentane compound shown in FIG. 17, where R=H. This did improve affinity with the compound of FIG. 17 showing a $K_d$=8 μM. Using the instant model, a one cage system (FIG. 24C) was compared with a two cage system (FIG. 24D), which predicted improved contrast with the two cage system at all time points during the experiment. A two cage system was then synthesized using the Virginia Orange fluorophore[25] (11, FIGS. 18 and 24E). Evaluation of this compound in vitro showed excellent performance (FIG. 24F) with higher contrst than the single-cage compound 402 (FIG. 8).

Example 3

(2-((5-Methoxy-2-nitrophenoxy)methoxy)ethyl)trimethylsilane (S2)

To a solution of 5-methoxy-2-nitrophenol (S1, 576 mg, 3.41 mmol) in DMF (60 mL) under nitrogen was added NaH (60%, 163 mg, 4.09 mmol, 1.2 eq). After stirring for 10 minutes, 2-(trimethylsilyl)ethoxymethyl chloride (723 μL, 4.09 mmol, 1.2 eq) was added. The reaction was stirred for 4 h at room temperature while shielded from light. The reaction was diluted with saturated NH$_4$Cl and extracted with EtOAc (3×). The organic layers were dried (MgSO$_4$), filtered, and concentrated in vacuo. The residue was purified by flash chromatography (0-20% EtOAc/hexanes, linear gradient; dry load with Celite) to afford S2 as an off-white, waxy solid (935 mg, 92%) (structure shown below).

$^1$H NMR (CDCl$_3$, 400 MHz) δ 7.95 (d, J=9.2 Hz, 1H), 6.82 (d, J=2.6 Hz, 1H), 6.56 (dd, J=9.2, 2.6 Hz, 1H), 5.34 (s, 2H), 3.87 (s, 3H), 3.85-3.79 (m, 2H), 1.01-0.92 (m, 2H), 0.01 (s, 9H); $^{13}$C NMR (CDCl$_3$, 101 MHz) δ 164.49 (C), 153.6 (C), 134.0 (C), 128.0 (CH), 106.8 (CH), 102.8 (CH), 94.0 (CH$_2$), 67.4 (CH$_2$), 56.0 (CH$_3$), 18.2 (CH$_2$), −1.3 (CH$_3$); HRMS (ESI) calcd for C$_{13}$H$_{21}$NO$_5$SiNa [M+Na]$^+$ 322.1081, found 322.1080.

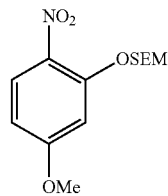

Example 4

4-Methoxy-2-((2-(trimethylsilyl)ethoxy)methoxy)aniline (S3)

Compound S2 (900 mg, 3.01 mmol) was dissolved in DMF (12 mL). After adding Pd/C (10% Pd, 90 mg), the reaction was flushed with nitrogen for 10 minutes. An H$_2$ balloon was attached to the flask, and the reaction vessel was flushed with H$_2$. The reaction was then stirred at room temperature under H$_2$ for 24 h (shielded from light). The reaction was filtered through Celite with CH$_2$Cl$_2$ and concentrated in vacuo to give a brown residue. Flash chromatography (5-60% EtOAc/hexanes, linear gradient) provided 702 mg (87%) of S3 as a yellow oil (structure shown below).

$^1$H NMR (CDCl$_3$, 400 MHz) δ 6.73 (d, J=2.7 Hz, 1H), 6.66 (d, J=8.5 Hz, 1H), 6.42 (dd, J=8.5, 2.7 Hz, 1H), 5.22 (s, 2H), 3.81-3.75 (m, 2H), 3.74 (s, 3H), 3.52 (s, 2H), 1.02-0.93 (m, 2H), 0.01 (s, 9H); $^{13}$C NMR (CDCl$_3$, 101 MHz) δ 153.2 (C), 146.2 (C), 130.5 (C), 116.0 (CH), 106.8 (CH), 103.0 (CH), 93.9 (CH$_2$), 66.5 (CH$_2$), 56.0 (CH$_3$), 18.2 (CH$_2$), −1.2 (CH$_3$); HRMS (ESI) calcd for C$_{13}$H$_{24}$NO$_3$Si [M+H]$^+$ 270.1520, found 270.1524.

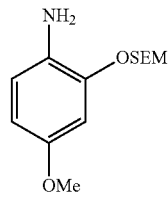

Example 5

Di-tert-butyl 2,2'-((4-methoxy-2-((2-(trimethylsilyl)ethoxy)methoxy)phenyl)azanediyl)diacetate (S4)

Aniline S3 (400 mg, 1.49 mmol) was dissolved in MeCN (30 mL); 1,8-bis(dimethylamino)naphthalene (1.274 g, 5.945 mmol, 4 eq), tert-butyl bromoacetate (1.739 g, 8.917 mmol, 6 eq) and NaI (67 mg, 0.446 mmol, 0.3 eq) were added sequentially. The resulting mixture was stirred at reflux for 18 h while being shielded from light. The reaction was cooled to room temperature, and the solvent was evaporated. The residue was diluted into $CH_2Cl_2$, washed with water (3×) and brine, dried ($MgSO_4$), filtered, and concentrated in vacuo. Purification by flash chromatography (0-20% EtOAc/hexanes, linear gradient) yielded S4 as a pale yellow gum (650 mg, 88%) (structure shown below).

$^1$H NMR ($CDCl_3$, 400 MHz) δ 6.83 (d, J=8.8 Hz, 1H), 6.74 (d, J=2.8 Hz, 1H), 6.45 (dd, J=8.8, 2.8 Hz, 1H), 5.22 (s, 2H), 3.95 (s, 4H), 3.81-3.75 (m, 2H), 3.74 (s, 3H), 1.42 (s, 18H), 1.02-0.89 (m, 2H), 0.01 (s, 9H); $^{13}$C NMR ($CDCl_3$, 101 MHz) δ 170.8 (C), 155.6 (C), 150.8 (C), 133.6 (C), 120.8 (CH), 106.3 (CH), 104.1 (CH), 93.8 ($CH_2$), 81.1 (C), 66.4 ($CH_2$), 55.7 ($CH_3$), 55.2 ($CH_2$), 28.3 ($CH_3$), 18.2 ($CH_2$), −1.2 ($CH_3$); HRMS (ESI) calcd for $C_{25}H_{44}NO_7Si$ [M+H]$^+$ 498.2882, found 498.2891.

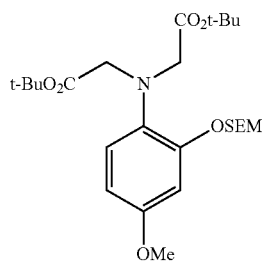

Example 6

Di-tert-butyl 2,2'-((2-hydroxy-4-methoxyphenyl)azanediyl)diacetate (1)

To a solution of S4 (624 mg, 1.25 mmol) in 1:1 THF/MeOH (76 mL) was added $H_2SO_4$ (2.51 mL) in MeOH (38 mL). The reaction was stirred at room temperature for 2 h (shielded from light). The reaction was carefully quenched with 0.1 M $NaHCO_3$, diluted with additional saturated $NaHCO_3$, and extracted with EtOAc (3×). The organic layers were dried ($MgSO_4$), filtered, and concentrated in vacuo. The brown residue was purified by silica gel chromatography (2-10% iPrOH/hexanes, linear gradient) to afford 362 mg (79%) of 1 as a photosensitive, off-white solid (structure shown below).

$^1$H NMR ($CDCl_3$, 400 MHz) δ 8.25 (s, 1H), 7.24 (d, J=8.7 Hz, 1H), 6.51 (d, J=2.9 Hz, 1H), 6.34 (dd, J=8.7, 2.9 Hz, 1H), 3.75 (s, 3H), 3.70 (s, 4H), 1.45 (s, 18H); $^{13}$C NMR ($CDCl_3$, 101 MHz) δ 171.6 (C), 159.2 (C), 155.1 (C), 130.6 (C), 127.4 (CH), 105.8 (CH), 100.8 (CH), 81.9 (C), 57.7 ($CH_2$), 55.5 ($CH_3$), 28.2 ($CH_3$); HRMS (ESI) calcd for $C_{19}H_{30}NO_6$ [M+H]$^+$ 368.2068, found 368.2062.

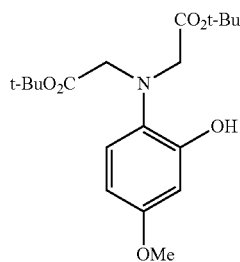

Example 7

Methyl 2-(4-(((tert-butyldimethylsilyl)oxy)methyl)-2-nitrophenoxy)acetate (S6)

Methyl 2-[4-(Hydroxymethyl)-2-nitrophenoxy]acetate (S5, 1.000 g, 4.146 mmol), TBSCl (750 mg, 4.98 mmol, 1.2 eq), and imidazole (423 mg, 6.22 mmol, 1.5 eq) were combined in $CH_2Cl_2$ (83 mL) and stirred at room temperature for 2 h while shielded from light. The reaction was diluted with brine and extracted with $CH_2Cl_2$ (3×). The combined organic extracts were dried ($MgSO_4$), filtered, and concentrated in vacuo. Flash chromatography of the crude product (0-20% EtOAc/hexanes, linear gradient, with constant 20% v/v $CH_2Cl_2$ additive) provided S6 (1.418 g, 96%) as a pale yellow solid (structure shown below).

$^1$H NMR ($CDCl_3$, 400 MHz) δ 7.82 (d, J=2.2 Hz, 1H), 7.47 (dd, J=8.6, 2.2 Hz, 1H), 6.97 (d, J=8.6 Hz, 1H), 4.77 (s, 2H), 4.70 (s, 2H), 3.80 (s, 3H), 0.94 (s, 9H), 0.10 (s, 6H); $^{13}$C NMR ($CDCl_3$, 101 MHz) δ 168.5 (C), 150.2 (C), 140.4 (C), 136.0 (C), 131.5 (CH), 123.5 (CH), 115.5 (CH), 67.0 ($CH_2$), 63.6 ($CH_2$), 52.6 ($CH_3$), 26.0 ($CH_3$), 18.5 (C), −5.2 ($CH_3$); HRMS (ESI) calcd for $C_{16}H_{25}NO_6SiNa$ [M+Na]$^+$ 378.1343, found 378.1347.

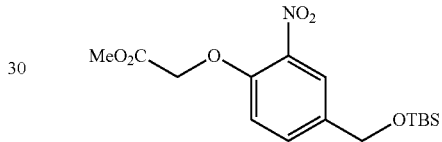

Example 8

2-(4-(((tert-Butyldimethylsilyl)oxy)methyl)-2-nitrophenoxy)ethanol (S7)

Ester S6 (1.392 g, 3.916 mmol) was taken up in MeOH (20 mL) under nitrogen and cooled to 0° C. $NaBH_4$ (1.481 g, 39.16 mmol, 10 eq) was added portionwise. The reaction was covered in foil and stirred at 0° C. for 4 h. It was subsequently quenched with $H_2O$ and extracted with EtOAc (3×). The combined organics were washed with brine, dried ($MgSO_4$), and evaporated. The resulting residue was purified by silica gel chromatography (0-30% EtOAc/hexanes, linear gradient, with constant 20% v/v $CH_2Cl_2$ additive) to give 1.260 g (98%) of S7 as a yellow oil (structure shown below).

$^1$H NMR ($CDCl_3$, 400 MHz) δ 7.83 (d, J=2.2 Hz, 1H), 7.50 (dd, J=8.6, 2.2 Hz, 1H), 7.07 (d, J=8.6 Hz, 1H), 4.71 (s, 2H), 4.27-4.20 (m, 2H), 3.98 (q, J=5.0 Hz, 2H), 2.46 (t, J=6.3 Hz, 1H), 0.94 (s, 9H), 0.11 (s, 6H); $^{13}$C NMR ($CDCl_3$, 101 MHz) δ 151.3 (C), 139.9 (C), 135.0 (C), 132.0 (CH), 123.5 (CH), 115.4 (CH), 71.7 ($CH_2$), 63.7 ($CH_2$), 61.2 ($CH_2$), 26.0 ($CH_3$), 18.5 (C), −5.1 ($CH_3$); HRMS (ESI) calcd for $C_{15}H_{25}NO_5SiNa$ [M+Na]$^+$ 350.1394, found 350.1396.

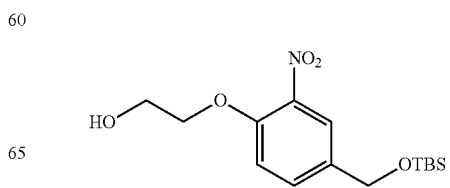

Example 9

((4-(2-(Allyloxy)ethoxy)-3-nitrobenzyl)oxy)(tert-butyl)dimethylsilane (S8)

A vial was charged with alcohol S7 (1.250 g, 3.817 mmol), allyl bromide (1.778 g, 14.70 mmol, 3.85 eq), KOH (1.008 g, 7.291 mmol, 1.91 eq), and tetrabutylammonium iodide (71 mg, 0.191 mmol, 0.05 eq). The resulting mixture was stirred at room temperature for 1 h while being shielded from light. The reaction was then diluted with $CH_2Cl_2$, combined with Celite, and evaporated to dryness. Flash chromatography (0-20% EtOAc/hexanes, linear gradient; dry load with Celite) afforded S8 as a yellow solid (1.316 g, 94%) (structure shown below).

$^1$H NMR (CDCl$_3$, 400 MHz) δ 7.79 (d, J=2.2 Hz, 1H), 7.47 (dd, J=8.6, 2.2 Hz, 1H), 7.08 (d, J=8.6 Hz, 1H), 5.92 (ddt, J=17.2, 10.4, 5.6 Hz, 1H), 5.31 (dq, J=17.2, 1.6 Hz, 1H), 5.20 (dq, J=10.4, 1.4 Hz, 1H), 4.70 (s, 2H), 4.29-4.22 (m, 2H), 4.11 (dt, J=5.6, 1.4 Hz, 2H), 3.88-3.81 (m, 2H), 0.93 (s, 9H), 0.10 (s, 6H); NMR (CDCl$_3$, 101 MHz) δ 151.4 (C), 140.1 (C), 134.61 (C), 134.60 (CH), 131.7 (CH), 123.3 (CH), 117.5 (CH$_2$), 115.3 (CH), 72.7 (CH$_2$), 70.0 (CH$_2$), 68.3 (CH$_2$), 63.7 (CH$_2$), 26.0 (CH$_3$), 18.5 (C), −5.1 (CH$_3$); HRMS (ESI) calcd for $C_{18}H_{29}NO_5SiNa$ [M+Na]$^+$ 390.1707. found 390.1712.

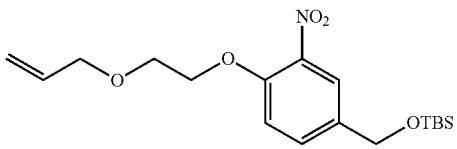 [SMILES: C=CCOCCOc1ccc(CO[Si](C)(C)C(C)(C)C)cc1[N+](=O)[O-]]

Example 10

2-(2-(Allyloxy)ethoxy)-5-(((tert-butyldimethylsilyl)oxy)methyl)aniline (S9)

A flask was charged with S8 (1.300 g, 3.537 mmol); EtOH (35.4 mL), H$_2$O (6.8 mL), and AcOH (3.8 mL) were added sequentially. Zinc powder (7.170 g, 109.7 mmol, 31 eq) was then added portionwise. The reaction was stirred at room temperature for 30 min (shielded from light). The mixture was filtered, and the filter and was rinsed with warm EtOH. The combined filtrate was diluted with brine and extracted with CH$_2$Cl$_2$ (3×). The combined organics were washed with water (3×) and saturated NaHCO$_3$, dried (MgSO$_4$), filtered, and concentrated in vacuo. The brown residue was purified by flash chromatography (0-40% EtOAc/hexanes, linear gradient) to yield 1.014 g (85%) of S9 as a yellow oil (structure shown below).

$^1$H NMR (CDCl$_3$, 400 MHz) δ 6.76 (d, J=8.2 Hz, 1H), 6.70 (d, J=2.0 Hz, 1H), 6.63 (dd, J=8.1, 2.0 Hz, 1H), 5.94 (ddt, J=17.2, 10.4, 5.6 Hz, 1H), 5.31 (dq, J=17.2, 1.6 Hz, 1H), 5.20 (dq, J=10.4, 1.3 Hz, 1H), 4.60 (s, 2H), 4.17-4.11 (m, 2H), 4.08 (dt, J=5.6, 1.4 Hz, 2H), 3.85 (s, 2H), 3.82-3.76 (m, 2H), 0.93 (s, 9H), 0.08 (s, 6H); $^{13}$C NMR (CDCl$_3$, 101 MHz) δ 145.6 (C), 137.0 (C), 135.1 (C), 134.8 (CH), 117.4 (CH$_2$), 116.3 (CH), 113.7 (CH), 112.9 (CH), 72.4 (CH$_2$), 68.9 (CH$_2$), 68.7 (CH$_2$), 65.1 (CH$_2$), 26.2 (CH$_3$), 18.6 (C), −5.0 (CH$_3$); HRMS (ESI) calcd for $C_{18}H_{32}NO_3Si$ [M+H]$^+$ 338.2146, found 338.2145.

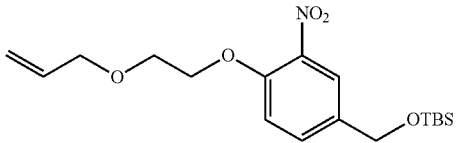 [SMILES: C=CCOCCOc1ccc(CO[Si](C)(C)C(C)(C)C)cc1[N+](=O)[O-]]

Example 11

Di-tert-butyl 2,2'((2-(2-(allyloxy)ethoxy)-5-(((tert-butyldimethylsilyl)oxy)methyl)phenyl)azanediyl) diacetate (S10)

Aniline S9 (1.000 g, 2.963 mmol) was dissolved in MeCN (30 mL); 1,8-bis(dimethylamino)naphthalene (2.540 g, 11.85 mmol, 4 eq), tert-butyl bromoacetate (3.467 g, 17.78 mmol, 6 eq) and NaI (133 mg, 0.889 mmol, 0.3 eq) were added sequentially. The resulting mixture was stirred at reflux for 18 h while being shielded from light. The reaction was cooled to room temperature, and the solvent was evaporated. The residue was diluted into CH$_2$Cl$_2$, washed with water (3×) and brine, dried (MgSO$_4$), filtered, and concentrated in vacuo. Purification by flash chromatography (0-20% EtOAc/hexanes, linear gradient) yielded S10 as a pale yellow oil (1.295 g, 77%) (structure shown below).

$^1$H NMR (CDCl$_3$, 400 MHz) δ 6.86-6.76 (m, 3H), 5.93 (ddt, J=17.2, 10.5, 5.6 Hz, 1H), 5.29 (dq, J=17.2, 1.6 Hz, 1H), 5.18 (dq, J=10.4, 1.3 Hz, 1H), 4.61 (s, 2H), 4.16 (dd, J=5.7, 4.8 Hz, 2H), 4.06 (dt, J=5.7, 1.5 Hz, 2H), 4.05 (s, 4H), 3.78 (dd, J=5.7, 4.8 Hz, 2H), 1.42 (s, 18H), 0.92 (s, 9H), 0.07 (s, 6H); $^{13}$C NMR (CDCl$_3$, 101 MHz) δ 170.7 (C), 149.6 (C), 139.6 (C), 134.9 (CH), 134.7 (C), 119.9 (CH), 117.8 (CH), 117.2 (CH$_2$), 114.9 (CH), 81.1 (C), 72.3 (CH$_2$), 68.8 (CH$_2$), 68.6 (CH$_2$), 65.1 (CH$_2$), 54.6 (CH$_2$), 28.3 (CH$_3$), 26.2 (CH$_3$), 18.6 (C), −5.0 (CH$_3$); HRMS (ESI) calcd for $C_{30}H_{52}NO_7Si$ [M+H]$^+$ 566.3508, found 566.3508.

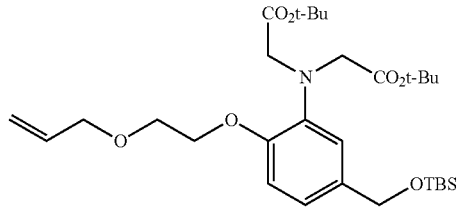 [SMILES: C=CCOCCOc1ccc(CO[Si](C)(C)C(C)(C)C)cc1N(CC(=O)OC(C)(C)C)CC(=O)OC(C)(C)C]

Example 12

Di-tert-butyl 2,2'((2-(2-(allyloxy)ethoxy)-5-(((tert-butyldimethylsilyl)oxy)methyl)-4-nitrophenyl)azanediyl) diacetate (S11)

Compound S10 (1.280 g, 2.262 mmol) was taken up in MeCN (22.6 mL) under nitrogen. AgNO$_3$ (422 mg, 2.49 mmol, 1.1 eq) and benzoyl chloride (384 mg, 2.49 mmol, 1.1 eq) were added sequentially while maintaining the temperature at or below 25° C. The reaction was then shielded from light and stirred at ≤25° C. for 30 min. The reaction mixture was filtered to remove AgCl, and the filter and was washed with saturated NaHCO$_3$. The combined filtrate was extracted with EtOAc (3×). The organic extracts were dried (MgSO$_4$), filtered, and concentrated in vacuo. The yellow residue was purified by silica gel chromatography (0-30% EtOAc/hexanes, linear gradient; dry load with Celite) to afford 1.155 g (84%) of S11 as a yellow solid (structure shown below).

$^1$H NMR (CDCl$_3$, 400 MHz) δ 7.76 (s, 1H), 7.17 (s, 1H), 5.93 (ddt, J=17.2, 10.5, 5.6 Hz, 1H), 5.30 (dq, J=17.2, 1.6 Hz, 1H), 5.20 (dq, J=10.4, 1.3 Hz, 1H), 5.06 (d, J=0.8 Hz, 2H), 4.24-4.19 (m, 2H), 4.17 (s, 4H), 4.06 (dt, J=5.6, 1.4 Hz, 2H), 3.82-3.76 (m, 2H), 1.45 (s, 18H), 0.97 (s, 9H), 0.13 (s, 6H); $^{13}$C NMR (CDCl$_3$, 101 MHz) δ 169.4 (C), 146.9 (C), 145.0 (C), 137.6 (C), 134.6 (CH), 134.4 (C), 117.4 (CH$_2$), 114.6 (CH), 111.1 (CH), 81.9 (C), 72.3 (CH$_2$), 69.0 (CH$_2$), 68.2 (CH$_2$), 62.8 (CH$_2$), 55.1 (CH$_2$), 28.3 (CH$_3$), 26.2 (CH$_3$), 18.6 (C), −5.1 (CH$_3$); HRMS (ESI) calcd for $C_{30}H_{50}N_2O_9SiNa$ [M+Na]$^+$ 633.3178, found 633.3182.

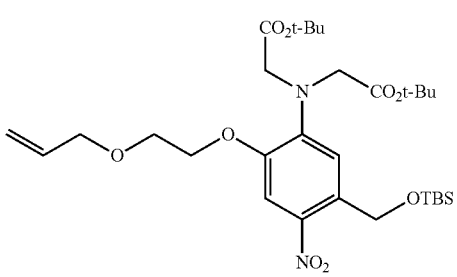 [SMILES: C=CCOCCOc1cc([N+](=O)[O-])c(CO[Si](C)(C)C(C)(C)C)cc1N(CC(=O)OC(C)(C)C)CC(=O)OC(C)(C)C]

Example 13

Di-tert-butyl 2,2'-((5-(((tert-butyldimethylsilyl)oxy)methyl)-2-(2-hydroxyethoxy)-4-nitrophenyl)azanediyl) diacetate (2)

A round-bottomed flask equipped with a condenser was charged with S11 (100 mg, 0.164 mmol), 1,3-dimethylbarbituric acid (51 mg, 0.327 mmol, 2 eq), and Pd(PPh$_3$)$_4$ (95 mg, 0.0819 mmol, 0.5 eq). After thoroughly flushing the reaction with nitrogen, THF (1.64 mL) was added. The reaction was shielded from light and stirred at reflux for 8 h. It was subsequently diluted with saturated NaHCO$_3$ and extracted with EtOAc (3×). The combined organics were washed with brine, dried (MgSO$_4$), filtered, and evaporated. The resulting orange residue was purified by flash chromatography (2-10% iPrOH/hexanes, linear gradient) to provide 2 (73 mg, 78%) as a yellow solid (structure shown below).

$^1$H NMR (CDCl$_3$, 400 MHz) δ 7.72 (s, 1H), 7.15 (s, 1H), 5.06 (d, J=0.7 Hz, 2H), 4.16-4.12 (m, 2H), 4.11 (s, 4H), 3.92-3.85 (m, 2H), 3.41 (t, J=7.1 Hz, 1H), 1.49 (s, 18H), 0.96 (s, 9H), 0.13 (s, 6H); $^{13}$C NMR (CDCl$_3$, 101 MHz) δ 170.3 (C), 147.0 (C), 145.0 (C), 137.8 (C), 134.4 (C), 114.2 (CH), 110.5 (CH), 82.7 (C), 72.2 (CH$_2$), 62.7 (CH$_2$), 60.8 (CH$_2$), 55.5 (CH$_2$), 28.2 (CH$_3$), 26.2 (CH$_3$), 18.6 (C), −5.1 (CH$_3$); HRMS (ESI) calcd for C$_{27}$H$_{47}$N$_2$O$_9$Si [M+H]$^+$ 571.3045, found 571.3059.

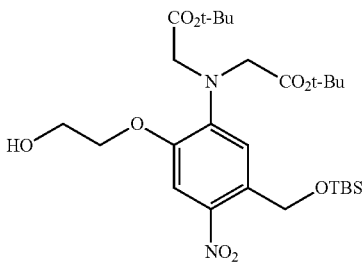 [SMILES: CC(C)(C)OC(=O)CN(CC(=O)OC(C)(C)C)c1cc(CO[Si](C)(C)C(C)(C)C)c([N+](=O)[O-])cc1OCCO]

Example 14

Di-tert-butyl 2,2'-((2-(2-(2-(bis(2-(tert-butoxy)-2-oxoethyl)amino)-4-(((tert-butyldimethylsilyl)oxy)methyl)-5-nitrophenoxy)ethoxy)-4-methoxyphenyl)azanediyl)diacetate (3)

A vial was charged with phenol 1 (77 mg, 0.210 mmol, 1.2 eq), alcohol 2 (100 mg, 0.175 mmol), and PPh$_3$ (51 mg, 0.193 mmol, 1.1 eq). The vial was sealed and evacuated/backfilled with nitrogen (3×). THF (160 μL) was added, and the resulting mixture was sonicated for 5 min to give a yellow slurry. DIAD (38 μL, 0.193 mmol, 1.1 eq) was added over 5 min (5 portions of 7-8 μL each, 1 min apart) while sonicating. The reaction was sonicated for an additional 20 min. It was then directly purified by silica gel chromatography (0-30% EtOAc/hexanes, linear gradient) to afford 3 as a yellow gum (129 mg, 80%) (structure shown below).

$^1$H NMR (CDCl$_3$, 400 MHz) δ 7.78 (s, 1H), 7.21 (s, 1H), 6.92 (d, J=8.7 Hz, 1H), 6.53 (d, J=2.8 Hz, 1H), 6.46 (dd, J=8.7, 2.8 Hz, 1H), 5.07 (s, 2H), 4.38 (s, 4H), 4.18 (s, 4H), 3.97 (s, 4H), 3.74 (s, 3H), 1.42 (s, 18H), 1.39 (s, 18H), 0.97 (s, 9H), 0.14 (s, 6H); $^{13}$C NMR (CDCl$_3$, 101 MHz) δ 170.5 (C), 169.4 (C), 155.8 (C), 151.9 (C), 146.9 (C), 145.1 (C), 137.7 (C), 134.5 (C), 133.8 (C), 121.7 (CH), 114.9 (CH), 111.1 (CH), 106.1 (CH), 103.6 (CH), 82.0 (C), 81.1 (C), 68.4 (CH$_2$), 67.6 (CH$_2$), 62.7 (CH$_2$), 55.7 (CH$_3$), 55.1 (CH$_2$), 54.9 (CH$_2$), 28.27 (CH$_3$), 28.26 (CH$_3$), 26.2 (CH$_3$), 18.6 (C), −5.1 (CH$_3$); HRMS (ESI) calcd for C$_{46}$H$_{73}$N$_3$O$_{14}$SiNa [M+Na]$^+$ 942.4754, found 942.4756.

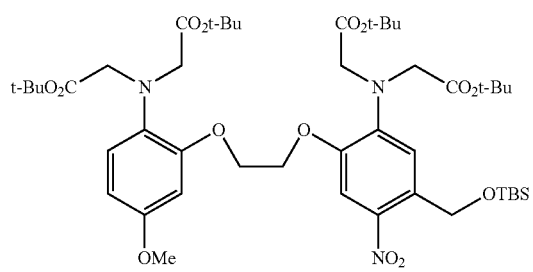

Example 15

Di-tert-butyl 2,2'((2-(2-(2-(bis(2-(tert-butoxy)-2-oxoethyl)amino)-4-(hydroxymethyl)-5-nitrophenoxy)ethoxy)-4-methoxyphenyl)azanediyl)diacetate (4)

To a solution of silyl ether 3 (170 mg, 0.185 mmol) in THF (5 mL) was added TBAF (1 M in THF, 222 μL, 0.222 mmol, 1.2 eq). After stirring for 10 min at room temperature, the reaction was diluted with saturated NH$_4$Cl and extracted with EtOAc (2×). The organic extracts were washed with brine, dried (MgSO$_4$), filtered, and concentrated in vacuo. Flash chromatography on silica gel (0-50% EtOAc/hexanes, linear gradient) provided 141 mg (95%) of 4 as a yellow solid (structure shown below).

$^1$H NMR (CDCl$_3$, 400 MHz) δ 7.76 (s, 1H), 6.92 (d, J=8.7 Hz, 1H), 6.86 (s, 1H), 6.52 (d, J=2.8 Hz, 1H), 6.46 (dd, J=8.7, 2.8 Hz, 1H), 4.87 (d, J=6.7 Hz, 2H), 4.39 (s, 4H), 4.18 (s, 4H), 3.96 (s, 4H), 3.74 (s, 3H), 2.64 (t, J=6.9 Hz, 1H), 1.45 (s, 18H), 1.39 (s, 18H); $^{13}$C NMR (CDCl$_3$, 101 MHz) δ 170.5 (C), 169.5 (C), 155.9 (C), 151.9 (C), 147.5 (C), 145.2 (C), 138.8 (C), 133.8 (C), 132.9 (C), 121.8 (CH), 116.9 (CH), 111.2 (CH), 106.1 (CH), 103.7 (CH), 82.2 (C), 81.1 (C), 68.4 (CH$_2$), 67.5 (CH$_2$), 63.4 (CH$_2$), 55.7 (CH$_3$), 55.1 (CH$_2$), 54.9 (CH$_2$), 28.3 (CH$_3$), 28.2 (CH$_3$); HRMS (ESI) calcd for C$_{40}$H$_{60}$N$_3$O$_{14}$ [M+H]$^+$ 806.4070, found 806.4074.

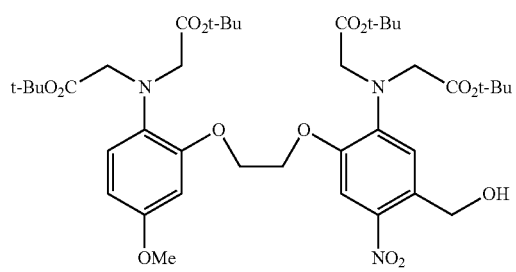

Example 16

Di-tert-butyl 2,2'((2-(2-(2-(bis(2-(tert-butoxy)-2-oxoethyl)amino)-4-(((3-(((1r,4r)-4-(bis(2-(tert-butoxy)-2-oxo ethyl)amino)cyclohexyl)carbamoyl)-2-oxo-2H-ehromen-7-yl)oxy)methyl)-5-nitrophenoxy)ethoxy)-4-methoxy phenyl)azanediyl)diacetate (401)

A vial was charged with alcohol 4 (30 mg, 37.2 μmol), 7-hydroxycoumarin-3-carboxamide (23.7 mg, 44.7 μmol, 1.2 eq), and PPh₃ (11.7 mg, 44.7 μmol, 1.2 eq). The vial was sealed and evacuated/backfilled with nitrogen (3×). THF (75 μL) was added, and the resulting mixture was sonicated for 5 min to give a yellow solution. DIAD (8.8 μL, 44.7 lima 1.2 eq) was added over 15 min (3 portions of ~3 μL each, 5 min apart) while sonicating. The reaction was sonicated for an additional 30 min. It was then directly purified by silica gel chromatography (10-50% EtOAc/hexanes, linear gradient) to afford 401 as a yellow gum (35 mg, 71%) (structure shown below).

$^1$H NMR (CDCl₃, 400 MHz) δ 8.83 (s, 1H), 8.61 (d, J=7.9 Hz, 1H), 7.85 (s, 1H), 7.61 (d, J=8.8 Hz, 1H), 7.03 (dd, J=8.7, 2.4 Hz, 1H), 7.01 (s, 1H), 6.97 (d, J=2.3 Hz, 1H), 6.93 (d, J=8.7 Hz, 1H), 6.53 (d, J=2.8 Hz, 1H), 6.47 (dd, J=8.7, 2.8 Hz, 1H), 5.55 (s, 2H), 4.41 (s, 4H), 4.15 (s, 4H), 3.97 (s, 4H), 3.92-3.84 (m, 1H), 3.74 (s, 3H), 3.47 (s, 4H), 2.77-2.67 (m, 1H), 2.16-2.08 (m, 2H), 2.00-1.92 (m, 2H), 1.46 (s, 18H), 1.42 (s, 18H), 1.40 (s, 18H), 1.38-1.23 (m, 4H); $^{13}$C NMR (CDCl₃, 101 MHz) δ 171.8 (C), 170.5 (C), 169.3 (C), 163.3 (C), 161.8 (C), 161.2 (C), 156.6 (C), 155.9 (C), 151.8 (C), 148.1 (CH), 147.7 (C), 145.2 (C), 138.0 (C), 133.8 (C), 131.2 (CH), 127.8 (C), 121.8 (CH), 115.6 (C), 114.6 (CH), 114.2 (CH), 113.2 (C), 111.1 (CH), 106.2 (CH), 103.8 (CH), 102.1 (CH), 82.2 (C), 81.1 (C), 80.8 (C), 68.4 (CH₂), 68.3 (CH₂), 67.5 (CH₂), 60.4 (CH), 55.7 (CH₃), 55.3 (CH₂), 54.9 (CH₂), 53.9 (CH₂), 48.6 (CH), 32.0 (CH₂), 29.4 (CH₂), 28.28 (CH₃), 28.26 (CH₃), 28.22 (CH₃); HRMS (ESI) calcd for C₆₈H₉₅N₅O₂₁Na [M+Na]⁺ 1340.6412, found 1340.6461; HRMS (ESI) calcd for C₆₈H₉₅N₅O₂₁Na₂ [M+2Na]²⁺ 681.8152, found 681.8155.

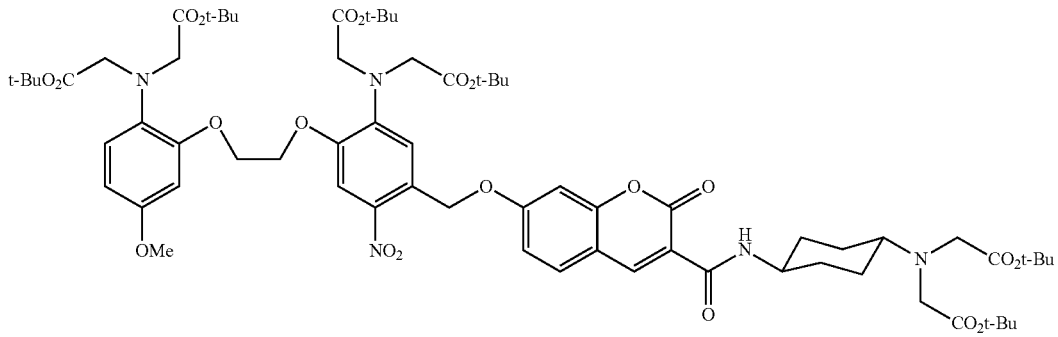

Example 17

2,2'((2-(2-(2-(Bis(carboxymethyl)amino)-4-(((3-(((1r,4r)-4-(bis(carboxymethyl)amino)cyclohexyl)carbamoyl)-2-oxo-2H-chromen-7-yl)oxy)methyl)-5-nitrophenoxy)ethoxy)-4-methoxyphenyl)azanediyl)diacetic acid (402)

To a solution of ester 401 (32 mg, 24.3 μmol) in CH₂Cl₂ (2.5 mL) was added TFA (0.5 mL). The reaction was stirred at room temperature for 24 h while shielded from light. Toluene (2 mL) was added, and the resulting mixture was concentrated to dryness. The residue was purified by reverse phase HPLC (10-95% MeCN/H₂O, linear gradient, with constant 0.1% v/v TFA additive) to afford 402 as a yellow solid (TFA salt, 22.3 mg, 84%) (structure shown below).

$^1$H NMR (DMSO-d₆, 400 MHz) δ 12.50 (s, 6H), 8.82 (s, 1H), 8.47 (d, J=7.7 Hz, 1H), 7.94 (d, J=8.9 Hz, 1H), 7.76 (s, 1H), 7.17 (d, J=2.1 Hz, 1H), 7.09 (dd, J=8.8, 2.3 Hz, 1H), 6.85 (s, 1H), 6.77 (d, J=8.8 Hz, 1H), 6.56 (d, J=2.7 Hz, 1H), 6.45 (dd, J=8.8, 2.7 Hz, 1H), 5.56 (s, 2H), 4.41-4.23 (m, 4H), 4.17 (s, 4H), 3.94 (s, 4H), 3.82-3.58 (m, 5H), 3.69 (s, 3H), 2.91-2.81 (m, 1H), 2.06-1.77 (m, 4H), 1.50-1.20 (m, 4H); Analytical HPLC: 98.2% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; UV detection at 254 nm); HRMS (ESI) calcd for C₄₄H₄₇N₅O₂₁Na [M+Na]⁺ 1004.2656, found 1004.2654.

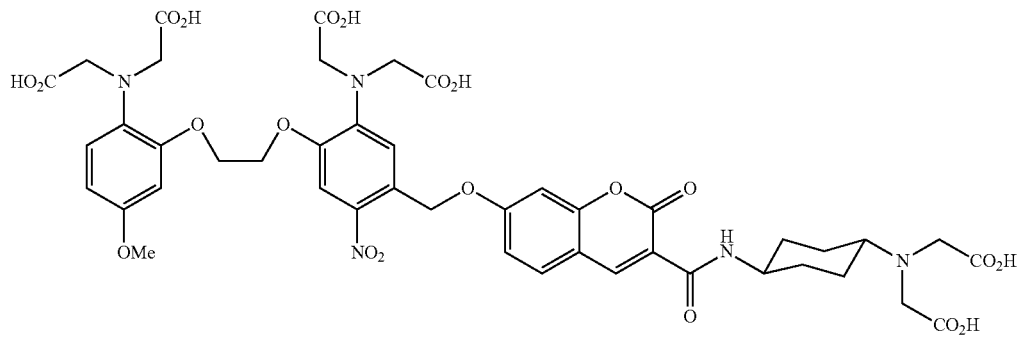 [SMILES: COc1ccc(N(CC(=O)O)CC(=O)O)c(OCCOc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]

Example 18

Bis(acetoxymethyl) 2,2'-((2-(2-(2-(bis(2-(acetoxymethoxy)-2-oxoethyl)amino)-4-(((3-(((1r,4r)-4-(bis(2-(acetoxy methoxy)-2-oxoethyl)amino)cyclohexyl)carbamoyl)-2-oxo-2H-chromen-7-yl)oxy) methyl)-5-nitrophenoxy) ethoxy)-4-methoxyphenyl) azanediyl)diacetate (403)

Acid 402 (15 mg, 13.7 μmol) was dissolved in DMF (2 mL); bromomethyl acetate (34 μL, 342 μmol, 25 eq) and DIEA (60 μL, 342 μmol, 25 eq) were added, and the reaction was stirred at room temperature for 24 h while shielded from light. The crude reaction mixture was concentrated in vacuo, and the resulting residue was purified by reverse phase HPLC (30-95% MeCN/H$_2$O, linear gradient, with constant 0.1% v/v TFA additive). Product fractions were combined, concentrated to remove MeCN, diluted with saturated NaHCO$_3$, and extracted with CH$_2$Cl$_2$ (2×). The combined organic extracts were dried (MgSO$_4$), filtered, and evaporated. Flash chromatography on silica gel (50-100% EtOAc/hexanes, linear gradient) afforded 9.8 mg (51%) of 403 as a yellow foam (structure shown below).

$^1$H NMR (CDCl$_3$, 400 MHz) δ 8.83 (s, 1H), 8.60 (d, J=7.9 Hz, 1H), 7.84 (s, 1H), 7.63 (d, J=8.8 Hz, 1H), 7.04 (dd, J=8.7, 2.4 Hz, 1H), 7.01-6.93 (m, 3H), 6.49-6.43 (m, 2H), 5.76 (s, 4H), 5.66 (s, 4H), 5.59 (s, 4H), 5.56 (s, 2H), 4.42-4.38 (m, 2H), 4.34-4.29 (m, 2H), 4.27 (s, 4H), 4.11 (s, 4H), 3.91-3.82 (m, 1H), 3.76 (s, 3H), 3.64 (s, 4H), 2.78-2.69 (m, 1H), 2.15-2.10 (m, 2H), 2.13 (s, 6H), 2.072 (s, 6H), 2.066 (s, 6H), 1.99-1.90 (m, 2H), 1.44-1.24 (m, 4H); Analytical HPLC: 98.9% purity (4.6 mm×150 mm 5 um C18 column; 5 μL injection; 30-95% CH$_3$CN/H$_2$O, linear gradient, with constant 0.1% v/v TFA additive; 20 min run; 1 mL/min flow; ESI; positive ion mode; UV detection at 254 nm); HRMS (ESI) calcd for C$_{62}$H$_{71}$N$_5$O$_{33}$Na [M+Na]$^+$ 1436.3924, found 1436.3960; HRMS (ESI) calcd for C$_{62}$H$_{71}$N$_5$O$_{33}$Na$_2$ [M+2Na]$^{2+}$ 729.6908, found 729.6903.

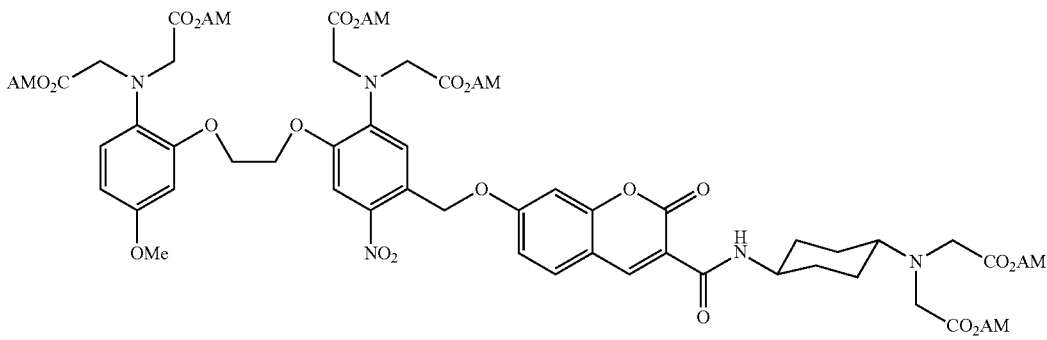

Example 19

Di-tert-butyl 2,2'-((2-(2-(2-(bis(2-(tert-butoxy)-2-oxoethyl)amino)-4-(((9-(4-methoxy-2-methylphenyl)-3-oxo-3H-xanthen-6-yl)oxy)methyl)-5-nitrophenoxy)ethoxy)-4-methoxyphenyl)azanediyl) diacetate (S12)

This compound (48%, orange solid), the structure of which is shown below, was prepared from 4 and Tokyo-Green[30] according to the procedure described for di-tert-butyl 2,2'-((2-(2-(2-(bis(2-(tert-butoxy)-2-oxoethyl)amino)-4-(((3-(((1r,4r)-4-(bis(2-(tert-butoxy)-2-oxo ethyl)amino) cyclohexyl)carbamoyl)-2-oxo-2H-chromen-7-yl)oxy) methyl)-5-nitrophenoxy)ethoxy)-4-methoxy phenyl) azanediyl)diacetate.

¹H NMR (CDCl₃, 400 MHz) δ 7.85 (s, 1H), 7.11-7.04 (m, 3H), 7.01 (s, 1H), 6.99 (d, J=9.7 Hz, 1H), 6.95-6.89 (m, 3H), 6.88-6.83 (m, 1H), 6.57 (dd, J=9.7, 1.9 Hz, 1H), 6.52 (d, J=2.8 Hz, 1H), 6.47 (dd, J=8.7, 2.8 Hz, 1H), 6.45 (d, J=1.9 Hz, 1H), 5.57 (s, 2H), 4.40 (s, 4H), 4.16 (s, 4H), 3.97 (s, 4H), 3.90 (s, 3H), 3.74 (s, 3H), 2.06 (s, 3H), 1.42 (s, 18H), 1.40 (s, 18H); ¹³C NMR (CDCl₃, 101 MHz) δ 186.0 (C), 170.5 (C), 169.4 (C), 162.8 (C), 160.5 (C), 159.0 (C), 155.9 (C), 154.6 (C), 151.8 (C), 149.4 (C), 147.6 (C), 145.2 (C), 138.0 (C), 137.8 (C), 133.8 (C), 130.8 (CH), 130.6 (CH), 130.3 (CH), 129.9 (CH), 128.1 (C), 124.7 (C), 121.8 (CH), 119.2 (C), 116.2 (CH), 115.5 (C), 114.6 (CH), 113.4 (CH), 111.7 (CH), 111.1 (CH), 106.2 (CH), 106.0 (CH), 103.9 (CH), 102.2 (CH), 82.2 (C), 81.1 (C), 68.4 (CH₂), 68.2 (CH₂), 67.5 (CH₂), 55.7 (CH₃), 55.5 (CH₃), 55.3 (CH₂), 54.9 (CH₂), 28.3 (CH₃), 28.2 (CH₃), 20.1 (CH₃); HRMS (ESI) calcd for C₆₁H₇₃N₃O₁₇Na [M+Na]⁺ 1142.4832, found 1142.4816.

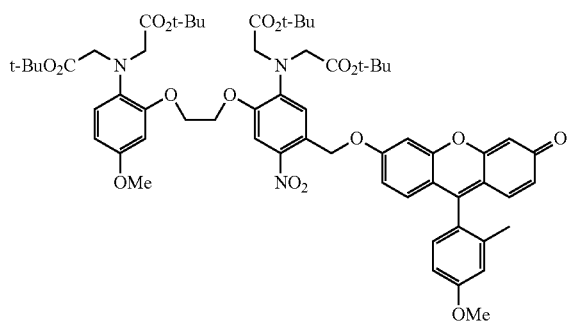

Example 20

2,2'-((2-(2-(2-(Bis(carboxymethyl)amino)-4-(((9-(4-methoxy-2-methylphenyl)-3-oxo-3H-xanthen-6-yl)oxy)methyl)-5-nitrophenoxy)ethoxy)-4-methoxyphenyl)azanediyl)diacetic acid (S13)

This compound (TFA salt, 75%, yellow-orange solid), the structure of which is shown below, was prepared from S12 according to the procedure described for 2,2'-((2-(2-(2-(Bis(carboxymethyl)amino)-4-(((3-(((1r,4r)-4-(bis(carboxymethyl)amino)cyclohexyl)carbamoyl)-2-oxo-2H-chromen-7-yl)oxy)methyl)-5-nitrophenoxy)ethoxy)-4-methoxyphenyl)azanediyl)diacetic acid.

¹H NMR (DMSO-d₆, 400 MHz) δ 12.47 (s, 4H), 7.78 (s, 1H), 7.45 (d, J=2.3 Hz, 1H), 7.24 (d, J=8.4 Hz, 1H), 7.17 (d, J=9.0 Hz, 1H), 7.14-7.08 (m, 3H), 7.03 (dd, J=8.4, 2.4 Hz, 1H), 6.86 (s, 1H), 6.77 (d, J=8.8 Hz, 1H), 6.68 (dd, J=9.6, 1.9 Hz, 1H), 6.58-6.53 (m, 2H), 6.45 (dd, J=8.8, 2.7 Hz, 1H), 5.64 (s, 2H), 4.39-4.32 (m, 2H), 4.31-4.25 (m, 2H), 4.18 (s, 4H), 3.94 (s, 4H), 3.87 (s, 3H), 3.69 (s, 3H), 2.01 (s, 3H); Analytical HPLC: 97.9% purity (4.6 mm×150 mm 5 μm C18 column; 5 μL injection; 10-95% CH₃CN/H₂O, linear gradient, with constant 0.1% v/v TFA additive; 20 min run; 1 mL/min flow; ESI; positive ion mode; UV detection at 254 nm); HRMS (ESI) calcd for C₄₅H₄₂N₃O₁₇ [M+H]⁺ 896.2509, found 896.2505.

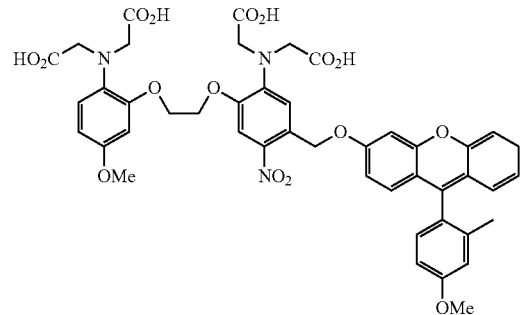 [SMILES: COc1ccc(C2=C3C=CCC=C3Oc3cc(OCc4cc(N(CC(=O)O)CC(=O)O)c(OCCOc5cc(OC)ccc5N(CC(=O)O)CC(=O)O)cc4[N+](=O)[O-])ccc32)c(C)c1]

Example 21

(2-((5-Bromo-2-nitrophenoxy)methoxy)ethyl)trimethylsilane (S15)

To a solution of 5-bromo-2-nitrophenol (S14, 1.00 g, 4.59 mmol) and DIEA (1.60 mL, 9.17 mmol, 2 eq) in CH₂Cl₂ (10 mL) was added 2-(trimethylsilyl)ethoxymethyl chloride (1.22 mL, 6.88 mmol, 1.5 eq). After stirring the reaction for 1 h at room temperature, it was diluted with water and extracted with CH₂Cl₂ (2×). The organic layers were washed with brine, dried (MgSO₄), filtered, and concentrated in vacuo. The residue was purified by flash chromatography (0-15% EtOAc/hexanes, linear gradient) to afford S15 as a yellow oil (1.49 g, 93%) (structure shown below).

¹H NMR (CDCl₃, 400 MHz) δ 7.71 (d, J=8.7 Hz, 1H), 7.53 (d, J=1.9 Hz, 1H), 7.21 (dd, J=8.7, 1.9 Hz, 1H), 5.34 (s, 2H), 3.87-3.76 (m, 2H), 1.02-0.91 (m, 2H), 0.01 (s, 9H); ¹³C NMR (CDCl₃, 101 MHz) δ 151.4 (C), 139.5 (C), 128.2 (C), 126.6 (CH), 124.7 (CH), 120.7 (CH), 94.1 (CH₂), 67.7 (CH₂), 18.1 (CH₂), −1.3 (CH₃); HRMS (EI) calcd for C₉H₉BrNO₄ [M-SiMe₃]⁺ 273.9715, found 273.9710.

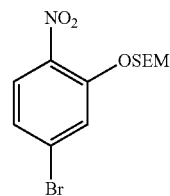

Example 22

4-Bromo-2-((2-(trimethylsilyl)ethoxy)methoxy)aniline (S16)

A solution of S15 (1.24 g, 3.56 mmol) in EtOAc (70 mL) was hydrogenated on an H-Cube Pro continuous-flow hydrogenation reactor (Raney Ni cartridge, 50° C., 60 bar, 1 mL/min). After a single pass through the hydrogenation reactor, the product solution was concentrated. The crude material was purified by silica gel chromatography (0-25% EtOAc/hexanes, linear gradient) to provide 959 mg (85%) of S16 as a pale yellow oil (structure shown below).

¹H NMR (CDCl₃, 400 MHz) δ 7.18 (d, J=2.1 Hz, 1H), 6.94 (dd, J=8.3, 2.1 Hz, 1H), 6.59 (d, J=8.3 Hz, 1H), 5.22 (s, 2H), 3.93-3.67 (m, 4H), 1.03-0.92 (m, 2H), 0.02 (s, 9H); ¹³C NMR (CDCl₃, 101 MHz) δ 145.8 (C), 136.0 (C), 125.1 (CH), 118.0 (CH), 116.3 (CH), 109.6 (C), 93.8 (CH₂), 66.7

(CH$_2$), 18.2 (CH$_2$), −1.3 (CH$_3$); HRMS (ESI) calcd for C$_{12}$H$_{21}$BrNO$_2$Si [M+H]$^+$ 318.0525, found 318.0534.

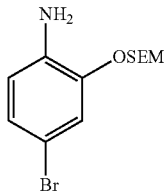

Example 23

Di-tert-butyl 2,2'-((4-bromo-2-((2-(trimethylsilyl) ethoxy)methoxy)phenyl)azanediyl)diacetate (S17)

Aniline S16 (900 mg, 2.83 mmol) was dissolved in MeCN (20 mL); tert-butyl bromoacetate (5.52 g, 28.3 mmol, 10 eq), 1,8-bis(dimethylamino)naphthalene (3.03 g, 14.1 mmol, 5 eq), and NaI (424 mg, 2.83 mmol, 1 eq) were added sequentially. The resulting mixture was stirred at reflux for 48 h. The reaction was cooled to room temperature, diluted with water, and extracted with EtOAc (2×). The combined organic extracts were washed with 0.5 N HCl and brine, dried (MgSO$_4$), filtered, and evaporated. Flash chromatography (0-20% Et$_2$O/hexanes, linear gradient) yielded S17 as a colorless oil (1.42 g, 92%) (structure shown below).

$^1$H NMR (CDCl$_3$, 400 MHz) δ 7.25 (d, J=2.3 Hz, 1H), 6.99 (dd, J=8.6, 2.3 Hz, 1H), 6.64 (d, J=8.6 Hz, 1H), 5.18 (s, 2H), 3.96 (s, 4H), 3.79-3.72 (m, 2H), 1.44 (s, 18H), 1.01-0.92 (m, 2H), 0.01 (s, 9H); $^{13}$C NMR (CDCl$_3$, 101 MHz) δ 170.5 (C), 149.8 (C), 139.1 (C), 125.0 (CH), 120.0 (CH), 119.6 (CH), 113.7 (C), 93.8 (CH$_2$), 81.4 (C), 66.7 (CH$_2$), 54.9 (CH$_2$), 28.3 (CH$_3$), 18.2 (CH$_2$), −1.2 (CH$_3$); HRMS (ESI) calcd for C$_{24}$H$_{41}$BrNO$_6$Si [M+H]$^+$ 546.1887, found 546.1899.

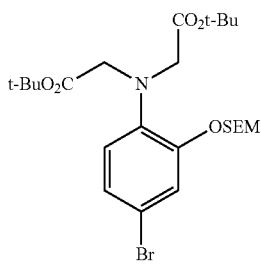

Example 24

Di-tert-butyl 2,2'-((4-bromo-2-hydroxyphenyl) azanediyl)diacetate (5)

To a solution of S17 (250 mg, 0.457 mmol) in 1:1 THF/MeOH (16 mL) was added H$_2$SO$_4$ (450 μL) in MeOH (8 mL). The reaction was stirred at room temperature for 45 min. It was then carefully quenched with saturated NaHCO$_3$, diluted with water, and extracted with EtOAc (2×). The organic layers were washed with brine, dried (MgSO$_4$), filtered, and concentrated in vacuo. The resulting residue was purified by silica gel chromatography (0-30% Et$_2$O/hexanes, linear gradient) to afford 115 mg (60%) of 5 as a colorless gum (structure shown below).

$^1$H NMR (CDCl$_3$, 400 MHz) δ 8.28 (s, 1H), 7.17 (d, J=8.4 Hz, 1H), 7.10 (d, J=2.3 Hz, 1H), 6.91 (dd, J=8.4, 2.3 Hz, 1H), 3.70 (s, 4H), 1.45 (s, 18H); $^{13}$C NMR (CDCl$_3$, 101 MHz) δ 171.4 (C), 154.9 (C), 136.7 (C), 127.8 (CH), 123.1 (CH), 120.2 (C), 119.2 (CH), 82.3 (C), 57.0 (CH$_2$), 28.2 (CH$_3$); HRMS (ESI) calcd for C$_{18}$H$_{26}$BrNO$_5$Na [M+Na]$^+$ 438.0892, found 438.0902.

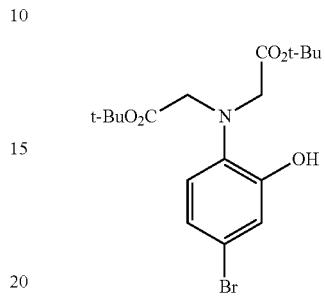

Example 25

Di-tert-butyl 2,2'-((2-(2-(2-(bis(2-(tert-butoxy)-2-oxoethyl)amino)-4-(((tert-butyldimethylsilyl)oxy) methyl)-5-nitrophenoxy)ethoxy)-4-bromophenyl) azanediyl)diacetate (6)

A vial was charged with phenol 5 (88 mg, 0.210 mmol, 1.2 eq), di-tert-butyl 2,2'-((5-(((tert-butyldimethylsilyl)oxy) methyl)-2-(2-hydroxyethoxy)-4-nitrophenyl)azanediyl) diacetate (2, 100 mg, 0.175 mmol), and PPh$_3$ (51 mg, 0.193 mmol, 1.1 eq). The vial was sealed and evacuated/backfilled with nitrogen (3×). THF (160 μL) was added, and the resulting mixture was sonicated for 5 min to give a yellow slurry. DIAD (38 μL, 0.193 mmol, 1.1 eq) was added over 5 min (5 portions of 7-8 μL each, 1 min apart) while sonicating. The reaction was sonicated for an additional 25 min. It was then directly purified by silica gel chromatography (0-25% EtOAc/hexanes, linear gradient) to provide 149 mg (88%) of 6 as a yellow solid (structure shown below).

$^1$H NMR (CDCl$_3$, 400 MHz) δ 7.77 (s, 1H), 7.22 (s, 1H), 7.05-7.00 (m, 2H), 6.79-6.74 (m, 1H), 5.07 (s, 2H), 4.41-4.33 (m, J=2.9 Hz, 4H), 4.17 (s, 4H), 4.00 (s, 4H), 1.43 (s, 18H), 1.40 (s, 18H), 0.97 (s, 9H), 0.14 (s, 6H); $^{13}$H NMR (CDCl$_3$, 101 MHz) δ 170.1 (C), 169.3 (C), 151.1 (C), 146.8 (C), 145.1 (C), 139.3 (C), 137.7 (C), 134.6 (C), 125.1 (CH), 121.2 (CH), 118.8 (CH), 115.0 (CH), 114.1 (C), 111.2 (CH), 82.0 (C), 81.5 (C), 68.2 (CH$_2$), 67.8 (CH$_2$), 62.7 (CH$_2$), 55.1 (CH$_2$), 54.5 (CH$_2$), 28.26 (CH$_3$), 28.25 (CH$_3$), 26.2 (CH$_3$), 18.6 (C), −5.1 (CH$_3$); HRMS (ESI) calcd for C$_{45}$H$_{71}$BrN$_3$O$_{13}$Si [M+H]$^+$ 968.3940, found 968.3951.

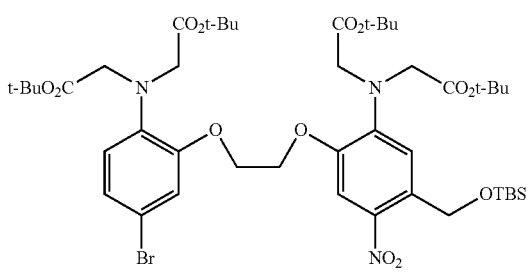

Example 26

Di-tert-butyl 2,2'-((2-(2-(2-(bis(2-(tert-butoxy)-2-oxoethyl)amino)-4-(((tert-butyldimethylsilyl)oxy)methyl)-5-nitrophenoxy)ethoxy)-4-(pyrrolidin-1-yl)phenyl)azanediyl)diacetate (7)

A vial was charged with 6 (150 mg, 155 µmol), Pd$_2$dba$_3$ (7.1 mg, 7.74 µmol, 0.05 eq), XPhos (11.1 mg, 23.2 µmol, 0.15 eq), and Cs$_2$CO$_3$ (81 mg, 248 µmol, 1.6 eq). The vial was sealed and evacuated/backfilled with nitrogen (3×). Dioxane (1.5 mL) was added, and the reaction was flushed again with nitrogen (3×). After adding pyrrolidine (19.4 µL, 232 µmol, 1.5 eq), the reaction was stirred at 80° C. for 24 h. It was then cooled to room temperature, filtered through Celite with CH$_2$Cl$_2$, and evaporated. The residue was purified by silica gel chromatography (0-30% EtOAc/hexanes, linear gradient) to afford 7 as a yellow solid (110 mg, 74%) (structure shown below).

$^1$H NMR (CDCl$_3$, 400 MHz) δ 7.79 (s, 1H), 7.20 (s, 1H), 6.94 (d, J=8.5 Hz, 1H), 6.18 (d, J=2.6 Hz, 1H), 6.15 (dd, J=8.6, 2.6 Hz, 1H), 5.07 (s, 2H), 4.48-4.41 (m, 2H), 4.40-4.33 (m, 2H), 4.20 (s, 4H), 3.95 (s, 4H), 3.25-3.16 (m, 4H), 2.01-1.91 (m, 4H), 1.43 (s, 18H), 1.40 (s, 18H), 0.97 (s, 9H), 0.14 (s, 6H); $^{13}$C NMR (CDCl$_3$, 101 MHz) δ 170.8 (C), 169.4 (C), 152.2 (C), 147.0 (C), 145.3 (C), 145.0 (C), 137.7 (C), 134.3 (C), 129.7 (C), 123.0 (CH), 114.7 (CH), 111.0 (CH), 105.6 (CH), 101.5 (CH), 81.9 (C), 80.9 (C), 68.6 (CH$_2$), 67.7 (CH$_2$), 62.8 (CH$_2$), 55.1 (CH$_2$), 48.1 (CH$_2$), 28.30 (CH$_3$), 28.27 (CH$_3$), 26.2 (CH$_3$), 25.6 (CH$_2$), 18.6 (C), −5.1 (CH$_3$); HRMS (ESI) calcd for C$_{49}$H$_{79}$N$_4$O$_{13}$Si [M+H]$^+$ 959.5413, found 959.5406.

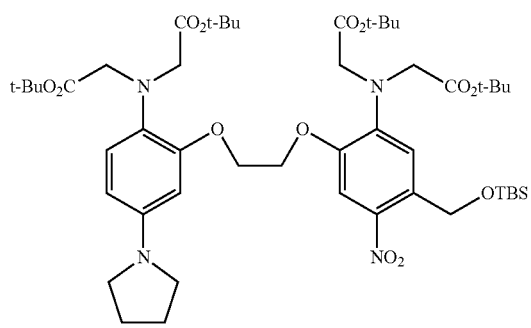

Example 27

Di-tert-butyl 2,2'-((2-(2-(2-(bis(2-(tert-butoxy)-2-oxoethyl)amino)-4-(hydroxymethyl)-5-nitrophenoxy)ethoxy)-4-(pyrrolidin-1-yl)phenyl)azanediyl)diacetate (8)

To a solution of silyl ether 7 (139 mg, 0.145 mmol) in THF (5 mL) was added TBAF (1 M in THF, 174 µL, 0.174 mmol, 1.2 eq). After stirring for 10 min at room temperature, the reaction was diluted with saturated NH$_4$Cl and extracted with EtOAc (2×). The organic extracts were washed with brine, dried (MgSO$_4$), filtered, and concentrated in vacuo. Flash chromatography on silica gel (0-50% EtOAc/hexanes, linear gradient) provided 111 mg (91%) of 8 as a yellow-orange foam (structure shown below).

$^1$H NMR (CDCl$_3$, 400 MHz) δ 7.76 (s, 1H), 6.94 (d, J=8.4 Hz, 1H), 6.85 (s, 1H), 6.19-6.13 (m, 2H), 4.87 (s, 2H), 4.48-4.41 (m, 2H), 4.41-4.34 (m, 2H), 4.20 (s, 4H), 3.93 (s, 4H), 3.25-3.14 (m, 4H), 2.73 (s, 1H), 2.01-1.92 (m, 4H), 1.46 (s, 18H), 1.40 (s, 18H); $^{13}$C NMR (CDCl$_3$, 101 MHz) δ 170.8 (C), 169.6 (C), 152.2 (C), 147.6 (C), 145.3 (C), 145.2 (C), 138.8 (C), 132.7 (C), 129.8 (C), 123.0 (CH), 116.9 (CH), 111.1 (CH), 105.7 (CH), 101.6 (CH), 82.1 (C), 80.9 (C), 68.5 (CH$_2$), 67.7 (CH$_2$), 63.5 (CH$_2$), 55.1 (CH$_2$), 48.1 (CH$_2$), 28.29 (CH$_3$), 28.25 (CH$_3$), 25.5 (CH$_2$); HRMS (ESI) calcd for C$_{43}$H$_{65}$N$_4$O$_{13}$ [M+H]$^+$ 845.4548, found 845.4559.

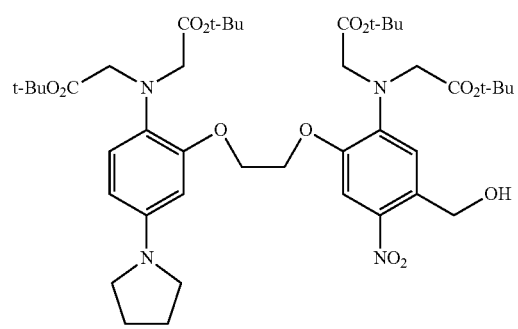

Example 28

Di-tert-butyl 2,2'-((2-(2-(2-(bis(2-(tert-butoxy)-2-oxoethyl)amino)-4-(((3-(((1r,4r)-4-(bis(2-(tert-butoxy)-2-oxoethyl)amino)cyclohexyl)carbamoyl)-2-oxo-2H-chromen-7-yl)oxy)methyl)-5-nitrophenoxy)ethoxy)-4-(pyrrolidin-1-yl)phenyl)azanediyl)diacetate (S22)

A vial was charged with alcohol 8 (35 mg, 41.4 µmol), 7-hydroxycoumarin-3-carboxamide (26.4 mg, 49.7 umol, 1.2 eq), and PPh$_3$ (13.0 mg, 49.7 umol, 1.2 eq). The vial was sealed and evacuated/backfilled with nitrogen (3×). THF (75 µL) was added, and the resulting mixture was sonicated for 5 min to give a yellow slurry. DIAD (9.8 µL, 49.7 µmol, 1.2 eq) was added over 15 min (3 portions of ~3 µL each, 5 min apart) while sonicating. The reaction was sonicated for an additional 30 min. It was then directly purified by silica gel chromatography (15-60% EtOAc/hexanes, linear gradient) to afford S22 as a yellow-orange gum (30 mg, 53%) (structure shown below).

$^1$H NMR (CDCl$_3$, 400 MHz) δ 8.83 (s, 1H), 8.62 (d, J=7.9 Hz, 1H), 7.86 (s, 1H), 7.62 (d, J=8.8 Hz, 1H), 7.03 (dd, J=8.7, 2.4 Hz, 1H), 7.00 (s, 1H), 6.98 (d, J=2.2 Hz, 1H), 6.95 (d, J=8.5 Hz, 1H), 6.20-6.14 (m, 2H), 5.55 (s, 2H), 4.49-4.43 (m, 2H), 4.43-4.37 (m, 2H), 4.17 (s, 4H), 3.94 (s, 4H), 3.92-3.82 (m, 1H), 3.48 (s, 4H), 3.25-3.16 (m, 4H), 2.78-2.67 (m, 1H), 2.16-2.07 (m, 2H), 2.01-1.90 (m, 6H), 1.46 (s, 18H), 1.43 (s, 18H), 1.40 (s, 18H), 1.38-1.26 (m, 4H); $^{13}$C NMR (CDCl$_3$, 101 MHz) δ 171.8 (C), 170.7 (C), 169.4 (C), 163.3 (C), 161.8 (C), 161.2 (C), 156.5 (C), 152.2 (C), 148.1 (CH), 147.8 (C), 145.3 (C), 145.2 (C), 137.9 (C), 131.2 (CH), 129.8 (C), 127.7 (C), 123.0 (CH), 115.5 (C), 114.4 (CH), 114.2 (CH), 113.1 (C), 111.0 (CH), 105.7 (CH), 102.0 (CH), 101.7 (CH), 82.2 (C), 80.9 (C), 80.8 (C), 68.6 (CH$_2$), 68.3 (CH$_2$), 67.7 (CH$_2$), 60.4 (CH), 55.3 (CH$_2$), 55.1 (CH$_2$), 53.9 (CH$_2$), 48.5 (CH), 48.0 (CH$_2$), 32.0 (CH$_2$), 29.4 (CH$_2$), 28.3 (CH$_3$), 28.2 (CH$_3$), 25.5 (CH$_2$); HRMS (ESI) calcd for C$_{71}$H$_{101}$N$_6$O$_{20}$ [M+H]$^+$ 1357.7071, found 1357.7108.

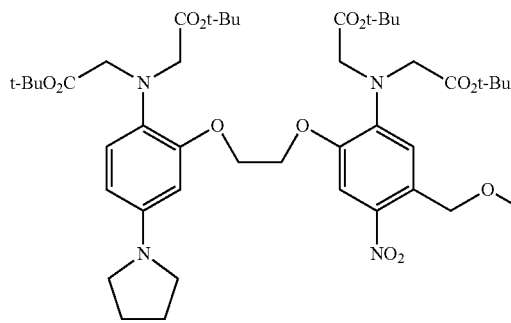

Example 29

Example 30

2,2'-((2-(2-(2-(Bis(carboxymethyl)amino)-4-(((3-(((1r,4r)-4-(bis(carboxymethyl)amino)cyclohexyl) carbamoyl)-2-oxo-2H-chromen-7-yl)oxy)methyl)-5-nitrophenoxy)ethoxy)-4-(pyrrolidin-1-yl)phenyl) azanediyl)diacetic acid To a solution of ester S22 (25 mg, 18.4 μmol) in CH$_2$Cl$_2$ (2.5 mL) was added TFA (0.5 mL). The reaction was stirred at room temperature for 24 h while shielded from light. Toluene (3 mL) was added, and the resulting mixture was concentrated to dryness. The residue was purified by reverse phase HPLC (10-95% MeCN/H$_2$O, linear gradient, with constant 0.1% v/v TFA additive) to afford 2,2'-((2-(2-(2-(Bis(carboxymethyl)amino)-4-(((3-(((1r,4r)-4-(bis(carboxymethyl)amino)cyclohexyl)carbamoyl)-2-oxo-2H-chromen-7-yl)oxy)methyl)-5-nitrophenoxy)ethoxy)-4-(pyrrolidin-1-yl) phenyl)azanediyl)diacetic acid as a yellow solid (TFA salt, 14.9 mg, 71%) (structure shown below).

$^1$H NMR (DMSO-d$_6$, 400 MHz) δ 12.44 (s, 6H), 8.82 (s, 1H), 8.48 (d, J=7.8 Hz, 1H), 7.93 (d, J=8.9 Hz, 1H), 7.78 (s, 1H), 7.17 (d, J=2.1 Hz, 1H), 7.09 (dd, J=8.7, 2.3 Hz, 1H), 6.87 (s, 1H), 6.81 (d, J=8.6 Hz, 1H), 6.22 (s, 1H), 6.10 (d, J=8.4 Hz, 1H), 5.56 (s, 2H), 4.41-4.27 (m, 4H), 4.20 (s, 4H), 3.98 (s, 4H), 3.90 (s, 4H), 3.85-3.76 (m, 1H), 3.21-3.15 (m, 5H), 2.08-1.86 (m, 8H), 1.67-1.51 (m, 2H), 1.44-1.29 (m, 2H); Analytical HPLC: 98.9% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; UV detection at 254 nm); HRMS (ESI) calcd for C$_{47}$H$_{53}$N$_6$O$_{20}$ [M+H]$^+$ 1021.3315, found 1021.3350.

Methyl 4-((trans-2-(allyloxy)cyclopentyl)oxy)-3-nitrobenzoate (S24)

A flask was charged with methyl 4-hydroxy-3-nitrobenzoate (2.47 g, 12.5 mmol), cis-2-(allyloxy)cyclopentanol (S23, 2.32 g, 16.3 mmol, 1.3 eq), and PPh$_3$ (4.94 g, 18.8 mmol, 1.5 eq). The flask was sealed and evacuated/back-filled with nitrogen (3×). THF (11 mL) was added dropwise over 15 min while sonicating, and the resulting mixture was sonicated for 5 min to give a yellow slurry. DIAD (3.71 mL, 18.8 mmol, 1.5 eq) was added dropwise over 15 min while sonicating. The reaction was sonicated for an additional 1 h, concentrated in vacuo, and purified by silica gel chromatography (0-25% EtOAc/hexanes, linear gradient) to yield 3.89 g (96%) of S24 as a pale yellow oil (structure shown below).

$^1$H NMR (CDCl$_3$, 400 MHz) δ 8.47 (d, J=2.2 Hz, 1H), 8.18 (dd, J=8.8, 2.2 Hz, 1H), 7.22 (d, J=8.9 Hz, 1H), 5.91 (ddt, J=17.2, 10.4, 5.6 Hz, 1H), 5.29 (dq, J=17.2, 1.6 Hz, 1H), 5.19 (dq, J=10.4, 1.3 Hz, 1H), 4.84-4.78 (m, 1H), 4.11-4.02 (m, 2H), 4.00-3.94 (m, 1H), 3.93 (s, 3H), 2.24-2.11 (m, 1H), 2.11-2.01 (m, 1H), 1.90-1.69 (m, 4H); $^{13}$C NMR (CDCl$_3$, 101 MHz) δ 165.1 (C), 154.5 (C), 140.0 (C), 135.0 (CH), 134.6 (CH), 127.3 (CH), 122.4 (C), 117.4 (CH$_2$), 115.3 (CH), 85.7 (CH), 84.2 (CH), 70.5 (CH$_2$), 52.6 (CH$_3$), 30.6 (CH$_2$), 30.4 (CH$_2$), 21.9 (CH$_2$); HRMS (ESI) calcd for C$_{16}$H$_{19}$NO$_6$Na [M+Na]$^+$ 344.1110, found 344.1119.

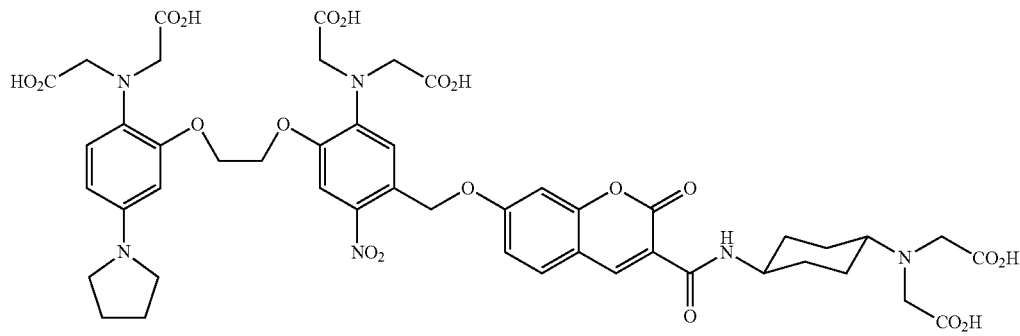 [SMILES: O=C(O)CN(CC(=O)O)c1ccc(N2CCCC2)cc1OCCOc1cc([N+](=O)[O-])c(COc2ccc3cc(C(=O)NC4CCC(N(CC(=O)O)CC(=O)O)CC4)c(=O)oc3c2)cc1N(CC(=O)O)CC(=O)O]

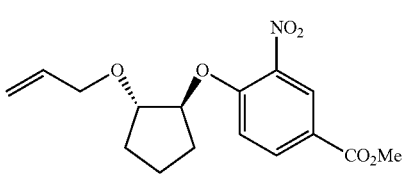 [SMILES: C=CCO[C@H]1CCC[C@@H]1Oc1ccc(C(=O)OC)cc1[N+](=O)[O-]]

Example 31

(4-((trans-2-(Allyloxy)cyclopentyl)oxy)-3-nitrophenyl)methanol (S25)

Ester S24 (3.59 g, 11.2 mmol) was taken up in THF (50 mL) under nitrogen. Lithium borohydride (2 M in THF, 14.0 mL, 28.0 mmol, 2.5 eq) was added, and the reaction was stirred at 50° C. for 90 min. The reaction mixture was cooled to room temperature, diluted with water, and extracted with EtOAc (2×). The combined organics were washed with brine, dried (MgSO$_4$), filtered, and evaporated. Silica gel chromatography (5-100% EtOAc/hexanes, linear gradient) afforded S25 as a yellow oil (1.95 g, 60%) (structure shown below).

$^1$H NMR (CDCl$_3$, 400 MHz) δ 7.81 (d, J=2.2 Hz, 1H), 7.51 (dd, J=8.6, 2.2 Hz, 1H), 7.15 (d, J=8.6 Hz, 1H), 5.91 (ddt, J=17.2, 10.4, 5.6 Hz, 1H), 5.28 (dq, J=17.2, 1.6 Hz, 1H), 5.18 (dq, J=10.4, 1.3 Hz, 1H), 4.77-4.71 (m, 1H), 4.68 (d, J=5.8 Hz, 2H), 4.10-4.01 (m, 2H), 3.97 (ddt, J=12.7, 5.7, 1.4 Hz, 1H), 2.19-2.00 (m, 2H), 1.88-1.67 (m, 5H); $^{13}$C NMR (CDCl$_3$, 101 MHz) δ 150.7 (C), 140.4 (C), 134.7 (CH), 133.3 (C), 132.4 (CH), 124.1 (CH), 117.3 (CH$_2$), 116.0 (CH), 85.2 (CH), 84.3 (CH), 70.5 (CH$_2$), 63.8 (CH$_2$), 30.5 (CH$_2$), 30.4 (CH$_2$), 21.9 (CH$_2$); HRMS (ESI) calcd for C$_{15}$H$_{19}$NO$_5$Na [M+Na]$^+$ 316.1161, found 316.1167.

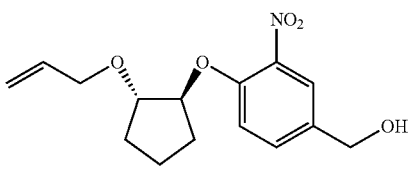 [SMILES: C=CCO[C@H]1CCC[C@@H]1Oc1ccc(CO)cc1[N+](=O)[O-]]

Example 32

((4-((trans-2-(Allyloxy)cyclopentyl)oxy)-3-nitrobenzyl)oxy)(tert-butyl)dimethylsilane (S26)

Alcohol S25 (2.19 g, 7.47 mmol), TBSCl (1.69 g, 11.2 mmol, 1.5 eq), and imidazole (762 mg, 11.2 mmol, 1.5 eq) were combined in DMF (30 mL) and stirred at room temperature for 90 min. The reaction was diluted with water and extracted with EtOAc (2×). The combined organic extracts washed with water and brine, dried (MgSO$_4$), filtered, and concentrated in vacuo. Flash chromatography of the crude product (0-10% EtOAc/hexanes, linear gradient) provided S25 as a pale yellow oil (2.83 g, 93%) (structure shown below).

$^1$H NMR (CDCl$_3$, 400 MHz) δ 7.75 (d, J=2.2 Hz, 1H), 7.45 (dd, J=8.6, 2.2 Hz, 1H), 7.12 (d, J=8.7 Hz, 1H), 5.91 (ddt, J=17.2, 10.4, 5.6 Hz, 1H), 5.28 (dq, J=17.2, 1.6 Hz, 1H), 5.17 (dq, J=10.4, 1.3 Hz, 1H), 4.75-4.70 (m, 1H), 4.69 (s, 2H), 4.10-4.01 (m, 2H), 3.97 (ddt, J=12.7, 5.7, 1.4 Hz, 1H), 2.19-1.99 (m, 2H), 1.88-1.65 (m, 4H), 0.94 (s, 9H), 0.11 (s, 6H); $^{13}$C NMR (CDCl$_3$, 101 MHz) δ 150.2 (C), 140.4 (C), 134.8 (CH), 134.0 (C), 131.4 (CH), 123.3 (CH), 117.3 (CH$_2$), 115.8 (CH), 85.1 (CH), 84.3 (CH), 70.5 (CH$_2$), 63.7 (CH$_2$), 30.6 (CH$_2$), 30.4 (CH$_2$), 26.0 (CH$_3$), 21.9 (CH$_2$), 18.5 (C), −5.1 (CH$_3$); HRMS (ESI) calcd for C$_{21}$H$_{33}$NO$_5$SiNa [M+Na]$^+$ 430.2026, found 430.2034.

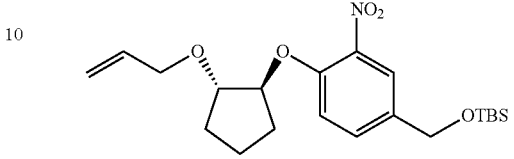

Example 33

2-((trans-2-(Allyloxy)cyclopentyl)oxy)-5-(((tert-butyldimethylsilyl)oxy)methyl)aniline (S27)

A flask was charged with S26 (2.41 g, 5.91 mmol); EtOH (62 mL), H$_2$O (12 mL), and AcOH (6 mL) were added sequentially. Zinc powder (11.6 g, 177 mmol, 30 eq) was then added portionwise. The reaction was stirred at room temperature for 30 min. The mixture was filtered through Celite with EtOH and CH$_2$Cl$_2$; the resulting filtrate was neutralized with saturated NaHCO$_3$ and extracted with CH$_2$Cl$_2$ (3×). The combined organics were washed with saturated NaHCO$_3$ and brine, dried (MgSO$_4$), filtered, and concentrated in vacuo. The residue was purified by flash chromatography (0-25% EtOAc/hexanes, linear gradient) to yield 2.12 g (95%) of S27 as a colorless oil (structure shown below).

$^1$H NMR (CDCl$_3$, 400 MHz) δ 6.80 (d, J=8.2 Hz, 1H), 6.70 (d, J=2.0 Hz, 1H), 6.64 (dd, J=8.2, 2.1 Hz, 1H), 5.92 (ddt, J=17.2, 10.4, 5.6 Hz, 1H), 5.27 (dq, J=17.2, 1.7 Hz, 1H), 5.17 (dq, J=10.4, 1.3 Hz, 1H), 4.64-4.60 (m, 1H), 4.60 (s, 2H), 4.07-3.96 (m, 3H), 3.74 (s, 2H), 2.16-1.95 (m, 2H), 1.85-1.66 (m, 4H), 0.93 (s, 9H), 0.09 (s, 6H); $^{13}$C NMR (CDCl$_3$, 101 MHz) δ 144.5 (C), 136.8 (C), 135.0 (CH), 134.5 (C), 117.0 (CH$_2$), 116.4 (CH), 113.6 (CH), 113.2 (CH), 84.5 (CH), 83.6 (CH), 70.4 (CH$_2$), 65.0 (CH$_2$), 30.8 (CH$_2$), 30.6 (CH$_2$), 26.2 (CH$_3$), 22.0 (CH$_2$), 18.6 (C), −5.0 (CH$_3$); HRMS (ESI) calcd for C$_{21}$H$_{36}$NO$_3$Si [M+H]$^+$ 378.2464, found 378.2465.

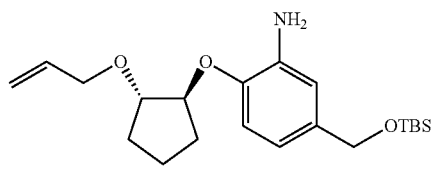 [SMILES: C=CCO[C@H]1CCC[C@@H]1Oc1ccc(CO[Si](C)(C)C(C)(C)C)cc1N]

Example 34

Di-tert-butyl 2,2'-((2-((trans-2-(allyloxy)cyclopentyl)oxy)-5-(((tert-butyldimethylsilyl)oxy)methyl)phenyl) azanediyl)diacetate (S28)

Aniline S27 (2.09 g, 5.54 mmol) was dissolved in MeCN (50 mL); tert-butyl bromoacetate (10.8 g, 55.4 mmol, 10 eq), 1,8-bis(dimethylamino)naphthalene (5.93 g, 27.7 mmol, 5 eq), and NaI (830 mg, 5.54 mmol, 1 eq) were added sequentially. The resulting mixture was stirred at reflux for 18 h. The reaction was cooled to room temperature, diluted with water, and extracted with EtOAc (2×). The combined organic extracts were washed with 1 N HCl and brine, dried (MgSO$_4$), filtered, and evaporated. Silica gel chromatography (0-10% EtOAc/hexanes, linear gradient) afforded S28 as a colorless oil (3.23 g, 96%) (structure shown below).

$^1$H NMR (CDCl$_3$, 400 MHz) δ 6.87-6.81 (m, 2H), 6.75 (s, 1H), 5.90 (ddt, J=17.2, 10.4, 5.6 Hz, 1H), 5.25 (dq, J=17.2, 1.6 Hz, 1H), 5.18-5.10 (m, 1H), 4.70-4.63 (m, 1H), 4.60 (s, 2H), 4.03 (s, 4H), 4.02-3.93 (m, 3H), 2.13-1.96 (m, 2H), 1.86-1.65 (m, 4H), 1.43 (s, 18H), 0.92 (s, 9H), 0.07 (s, 6H); $^{13}$C NMR (CDCl$_3$, 101 MHz) δ 170.6 (C), 148.4 (C), 139.4 (C), 135.1 (CH), 133.9 (C), 119.8 (CH), 117.8 (CH), 117.0 (CH$_2$), 114.7 (CH), 84.5 (CH), 83.5 (CH), 81.1 (C), 70.3 (CH$_2$), 65.1 (CH$_2$), 54.3 (CH$_2$), 30.92 (CH$_2$), 30.86 (CH$_2$), 28.3 (CH$_3$), 26.1 (CH$_3$), 22.4 (CH$_2$), 18.6 (C), −5.0 (CH$_3$); HRMS (ESI) calcd for C$_{33}$H$_{56}$NO$_7$Si [M+H]$^+$ 606.3826, found 606.3813.

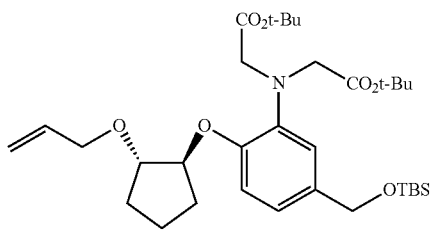 [SMILES: C=CCO[C@H]1CCC[C@@H]1Oc1ccc(CO[Si](C)(C)C(C)(C)C)cc1N(CC(=O)OC(C)(C)C)CC(=O)OC(C)(C)C]

Example 35

Di-tert-butyl 2,2'-((2-((trans-2-(allyloxy)cyclopentyl)oxy)-5-(((tert-butyldimethylsilyl)oxy)methyl)-4-nitrophenyl)azanediyl)diacetate (S29)

Compound S28 (3.31 g, 5.46 mmol) was taken up in MeCN (60 mL) under nitrogen. AgNO$_3$ (1.02 g, 6.01 mmol, 1.1 eq) and benzoyl chloride (845 mg, 6.01 mmol, 1.1 eq) were added sequentially while maintaining the temperature at or below 25° C. The reaction was then shielded from light and stirred at ≤25° C. for 2 h. The reaction mixture was filtered through Celite with EtOAc; the resulting filtrate was diluted with saturated NaHCO$_3$ and extracted with EtOAc (2×). The organic extracts were washed with brine, dried (MgSO$_4$), filtered, and concentrated in vacuo. The crude material was purified by flash chromatography (0-25% Et$_2$O/hexanes, linear gradient) to provide 2.19 g (62%) of S29 as a yellow gum (structure shown below).

$^1$H NMR (CDCl$_3$, 400 MHz) δ 7.85 (s, 1H), 7.15 (s, 1H), 5.95 (ddt, J=17.2, 10.4, 5.7 Hz, 1H), 5.28 (dq, J=17.2, 1.6 Hz, 1H), 5.21-5.13 (m, 1H), 5.08-5.03 (m, 2H), 4.72-4.64 (m, 1H), 4.14 (AB quartet, □$_A$=1664.2 Hz, □$_B$=1645.3 Hz, J$_{AB}$=18.9 Hz, 4H), 4.07-3.94 (m, 3H), 2.25-2.11 (m, 1H), 2.05-1.93 (m, 1H), 1.88-1.68 (m, 4H), 1.46 (s, 18H), 0.96 (s, 9H), 0.13 (s, 6H); $^{13}$C NMR (CDCl$_3$, 101 MHz) δ 169.4 (C), 145.9 (C), 144.9 (C), 137.8 (C), 134.8 (CH), 133.7 (C), 117.4 (CH$_2$), 114.7 (CH), 111.2 (CH), 84.8 (CH), 84.1 (CH), 82.1 (C), 70.6 (CH), 62.7 (CH$_2$), 54.7 (CH$_2$), 30.9 (CH$_2$), 30.8 (CH$_2$), 28.3 (CH$_3$), 26.2 (CH$_3$), 22.5 (CH$_2$), 18.6 (C), −5.1 (CH$_3$); HRMS (ESI) calcd for C$_{33}$H$_{55}$N$_2$O$_9$Si [M+H]$^+$ 651.3677, found 651.3688.

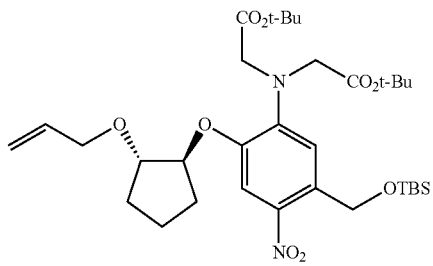 [SMILES: C=CCO[C@H]1CCC[C@@H]1Oc1cc([N+](=O)[O-])c(CO[Si](C)(C)C(C)(C)C)cc1N(CC(=O)OC(C)(C)C)CC(=O)OC(C)(C)C]

Example 36

Di-tert-butyl 2,2'-((5-(((tert-butyldimethylsilyl)oxy)methyl)-2-((trans-2-hydroxycyclopentyl)oxy)-4-nitrophenyl)azanediyl)diacetate (9)

A round-bottomed flask equipped with a condenser was charged with S29 (500 mg, 0.768 mmol), 1,3-dimethylbarbituric acid (240 mg, 1.54 mmol, 2 eq), and Pd(PPh$_3$)$_4$ (444 mg, 0.384 mmol, 0.5 eq). The apparatus was sealed and evacuated/backfilled with nitrogen (3×). THF (10 mL) was added; the reaction was shielded from light and stirred at reflux for 8 h. It was subsequently cooled to room temperature, diluted with saturated NaHCO$_3$ and extracted with EtOAc (2×). The combined organics were washed with brine, dried (MgSO$_4$), filtered, and evaporated. Flash chromatography on silica gel (0-40% EtOAc/hexanes, linear gradient) afforded 9 as a yellow gum (432 mg, 92%) (structure shown below).

$^1$H NMR (CDCl$_3$, 400 MHz) δ 7.75 (s, 1H), 7.20 (s, 1H), 5.06 (d, J=0.7 Hz, 2H), 4.50-4.44 (m, 1H), 4.32-4.26 (m, 1H), 4.13 (s, 4H), 2.63 (d, J=3.7 Hz, 1H), 2.37-2.22 (m, 1H), 2.09-1.98 (m, 1H), 1.90-1.59 (m, 4H), 1.46 (s, 18H), 0.97 (s, 9H), 0.13 (s, 6H); $^{13}$C NMR (CDCl$_3$, 101 MHz) δ 169.7 (C), 146.8 (C), 145.4 (C), 138.2 (C), 134.1 (C), 115.2 (CH), 112.5 (CH), 87.6 (CH), 82.4 (C), 77.1 (CH), 62.7 (CH$_2$), 55.1 (CH$_2$), 31.5 (CH$_2$), 29.6 (CH$_2$), 28.3 (CH$_3$), 26.2 (CH$_3$), 20.6 (CH$_2$), 18.6 (C), −5.1 (CH$_3$); HRMS (ESI) calcd for C$_{30}$H$_{51}$N$_2$O$_9$Si [M+H]$^+$ 611.3364, found 611.3356.

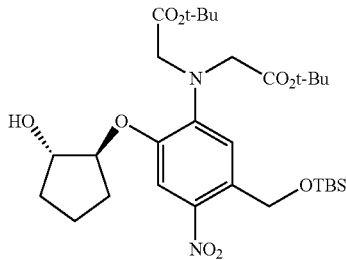 [SMILES: CC(C)(C)OC(=O)CN(CC(=O)OC(C)(C)C)c1cc(CO[Si](C)(C)C(C)(C)C)c([N+](=O)[O-])cc1O[C@H]1CCC[C@@H]1O]

Example 37

Di-tert-butyl 2,2'-((2-((cis-2-(2-(bis(2-(tert-butoxy)-2-oxoethyl)amino)-4-(hydroxymethyl)-5-nitrophenoxy)cyclopentyl)oxy)-4-methoxyphenyl)azanediyl)diacetate (10)

A vial was charged with alcohol 9 (360 mg, 0.589 mmol) and di-tert-butyl 2,2'-((2-hydroxy-4-methoxyphenyl)

azanediyl)diacetate (1, 325 mg, 0.884 mmol, 1.5 eq). The vial was sealed and evacuated/backfilled with nitrogen (3×). Freshly degassed toluene (800 μL) was added, and the mixture was heated to 100° C. while stirring vigorously. Separate solutions of DIAD (232 μL, 1.18 mmol, 2 eq) in toluene (800 μL) and PPh$_3$ (309 mg, 1.18 mmol, 2 eq) in toluene (800 μL) were simultaneously added to the heated reaction mixture dropwise over 2 h. The reaction was stirred an additional 1 h at 100° C. It was then cooled to room temperature and directly purified by silica gel chromatography (0-20% EtOAc/hexanes, linear gradient) to provide the TBS-protected Mitsunobu adduct as a yellow-orange residue (S31; ~100 mg, coeluted with Ph$_3$PO). This intermediate was dissolved in THF (4 mL), and TBAF (1 M in THF, 208 μL, 0.208 mmol, 2 eq) was added. After stirring at room temperature for 10 min, the reaction was diluted with saturated NH$_4$Cl and extracted with EtOAc (2×). The combined organic extracts were washed with brine, dried (MgSO$_4$), filtered, and concentrated in vacuo. Purification by flash chromatography (0-40% EtOAc/hexanes, linear gradient) afforded 65 mg (13%, 2 steps) of 10 as a yellow gum (structure shown below).

$^1$H NMR (CDCl$_3$, 400 MHz) δ 7.72 (s, 1H), 6.94-6.90 (m, 1H), 6.86 (s, 1H), 6.47-6.41 (m, 2H), 5.04-4.97 (m, 1H), 4.84 (d, J=6.9 Hz, 2H), 4.80 (q, J=5.4 Hz, 1H), 4.39 (d, J=18.0 Hz, 2H), 4.18 (d, J=18.0 Hz, 2H), 3.90 (AB quartet, $\square_A$=1567.8 Hz, $\square_B$=1552.3 Hz, J$_{AB}$=17.3 Hz, 4H), 3.63 (s, 3H), 2.69 (t, J=6.9 Hz, 1H), 2.14-1.89 (m, 5H), 1.74-1.62 (m, 1H), 1.44 (s, 18H), 1.37 (s, 18H); $^{13}$C NMR (acetone-d$_6$, 101 MHz) δ 170.8 (C), 170.1 (C), 156.8 (C), 152.4 (C), 147.1 (C), 146.2 (C), 138.7 (C), 135.2 (C), 134.7 (C), 123.4 (CH), 116.2 (CH), 111.8 (CH), 107.5 (CH), 106.1 (CH), 81.8 (C), 80.9 (C), 80.4 (CH), 80.2 (CH), 62.0 (CH$_2$), 55.6 (CH$_3$), 55.49 (CH$_2$), 55.45 (CH$_2$), 29.2 (CH$_2$), 29.1 (CH$_2$), 28.32 (CH$_3$), 28.31 (CH$_3$), 19.7 (CH$_2$); HRMS (ESI) calcd for C$_{43}$H$_{64}$N$_3$O$_{14}$ [M-41]$^+$ 846.4388, found 846.4377.

Example 38

Di-tert-butyl 2,2'-((trans-4-(7-((5-(bis(2-(tert-butoxy)-2-oxoethyl)amino)-4-((cis-2-(2-(bis(2-(tert-butoxy)-2-oxoethyl)amino)-5-methoxyphenoxy)cyclopentyl)oxy)-2-nitrobenzyl)oxy)-2-oxo-2H-chromene-3-carboxamido)cyclohexyl)azanediyl) diacetate (S33)

A vial was charged with alcohol 10 (34 mg, 40.2 μmol), 7-hydroxycoumarin-3-carboxamide (25.6 mg, 48.2 μmol, 1.2 eq), and PPh$_3$ (12.6 mg, 48.2 μmol, 1.2 eq). The vial was sealed and evacuated/backfilled with nitrogen (3×). THF (200 μL) was added, and the resulting mixture was sonicated for 5 min to give a yellow slurry. DIAD (9.5 μL, 48.2 μmol, 1.2 eq) was added over 15 min (3 portions of ~3 μL each, 5 min apart) while sonicating. The reaction was sonicated for an additional 30 min. It was then directly purified by silica gel chromatography (10-100% EtOAc/hexanes, linear gradient) to afford S33 as a yellow gum (41 mg, 75%) (structure shown below).

$^1$H NMR (CDCl$_3$, 400 MHz) δ 8.82 (s, 1H), 8.61 (d, J=7.9 Hz, 1H), 7.81 (s, 1H), 7.61 (d, J=8.8 Hz, 1H), 7.07-7.00 (m, 2H), 6.98 (d, J=2.3 Hz, 1H), 6.93 (d, J=8.8 Hz, 1H), 6.48-6.42 (m, 2H), 5.52 (s, 2H), 5.07-4.97 (m, 1H), 4.82 (q, J=5.4 Hz, 1H), 4.36 (d, J=18.0 Hz, 2H), 4.15 (d, J=18.0 Hz, 2H), 3.94-3.83 (m, 1H), 3.92 (AB quartet, $\square_A$=1574.9 Hz, $\square_B$=1561.0 Hz, J$_{AB}$=17.3 Hz, 4H), 3.63 (s, 3H), 3.47 (s, 4H), 2.78-2.67 (m, 1H), 2.16-1.90 (m, 9H), 1.75-1.64 (m, 1H), 1.46 (s, 18H), 1.40 (s, 18H), 1.37 (s, 18H), 1.40-1.20 (m, 4H); $^{13}$C NMR (acetone-d$_6$, 101 MHz) δ 172.0 (C), 170.7 (C), 169.9 (C), 164.3 (C), 162.2 (C), 161.3 (C), 157.5 (C), 156.8 (C), 152.3 (C), 148.5 (CH), 148.1 (C), 146.0 (C), 139.3 (C), 135.1 (C), 132.4 (CH), 127.5 (C), 123.4 (CH), 116.9 (CH), 116.5 (CH), 115.0 (C), 113.9 (C), 112.2 (CH), 107.4 (CH), 106.0 (CH), 102.4 (CH), 81.9 (C), 80.9 (C), 80.6 (C), 80.5 (CH), 80.1 (CH), 69.0 (CH$_2$), 61.1 (CH), 55.7 (CH$_2$), 55.6 (CH$_3$), 55.4 (CH$_2$), 54.2 (CH$_2$), 49.1 (CH), 32.5 (CH$_2$), 29.2 (CH$_2$), 28.3 (CH$_3$), 19.8 (CH$_2$); HRMS (ESI) calcd for C$_{71}$H$_{100}$N$_5$O$_{21}$ [M+H]$^+$ 1358.6911, found 1358.6891.

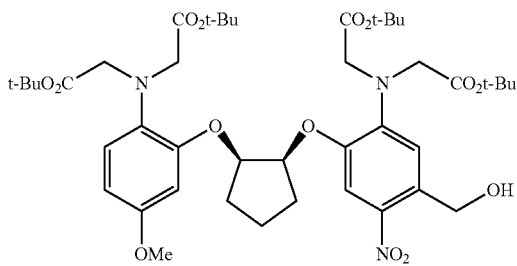

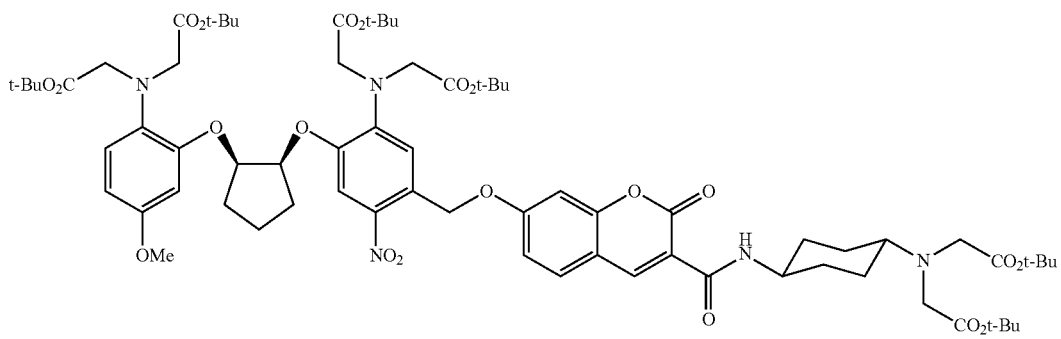

Example 39

2,2'-((trans-4-(7-(((5-(Bis(carboxymethyl)amino)-4-((cis-2-(2-(bis(carboxymethyl)amino)-5-methoxyphenoxy)cyclopentyl)oxy)-2-nitrobenzyl)oxy)-2-oxo-2H-chromene-3-carboxamido)cyclohexyl)azanediyl)diacetic acid To a solution of ester S33 (37 mg, 27.2 μmol in $CH_2Cl_2$ (2.5 mL) was added TFA (0.5 mL). The reaction was stirred at room temperature for 24 h while shielded from light. Toluene (2 mL) was added, and the resulting mixture was concentrated to dryness. The residue was purified by reverse phase HPLC (10-95% MeCN/$H_2O$, linear gradient, with constant 0.1% v/v TFA additive) to afford 2,2'-((trans-4-(7-((5-(Bis(carboxymethyl)amino)-4-((cis-2-(2-(bis(carboxymethyl)amino)-5-methoxyphenoxy)cyclopentypoxy)-2-nitrobenzypoxy)-2-oxo-2H-chromene-3-carboxamido)cyclohexypazanediyl)diacetic acid as a yellow solid (TFA salt, 23.8 mg, 77%) (structure shown below).

$^1$H NMR (MeOD, 400 MHz) δ 8.90 (d, J=7.8 Hz, 1H), 8.80 (s, 1H), 7.84 (s, 1H), 7.76 (d, J=8.8 Hz, 1H), 7.08 (dd, J=8.7, 2.4 Hz, 1H), 7.01 (d, J=8.7 Hz, 1H), 6.99 (d, J=2.3 Hz, 1H), 6.95 (s, 1H), 6.61 (d, J=2.7 Hz, 1H), 6.41 (dd, J=8.7, 2.7 Hz, 1H), 5.56 (s, 2H), 5.12-5.03 (m, 2H), 4.33 (d, J=18.4 Hz, 2H), 4.20 (s, 4H), 4.18 (d, J=18.3 Hz, 2H), 3.93-3.84 (m, 1H), 3.89 (d, J=18.0 Hz, 2H), 3.77 (d, J=18.0 Hz, 2H), 3.70 (s, 3H), 3.56-3.48 (m, 1H), 2.26-1.93 (m, 9H), 1.81-1.66 (m, 3H), 1.56-1.43 (m, 2H); Analytical HPLC: >99% purity (4.6 mm×150 mm 5 μm C18 column; 5 μL injection; 10-95% $CH_3CN/H_2O$, linear gradient, with constant 0.1% v/v TFA additive; 20 min run; 1 mL/min flow; ESI; positive ion mode; UV detection at 254/350 nm); HRMS (ESI) calcd for $C_{47}H_{52}N_5O_{21}$ $[M+H]^+$ 1022.3155, found 1022.3166.

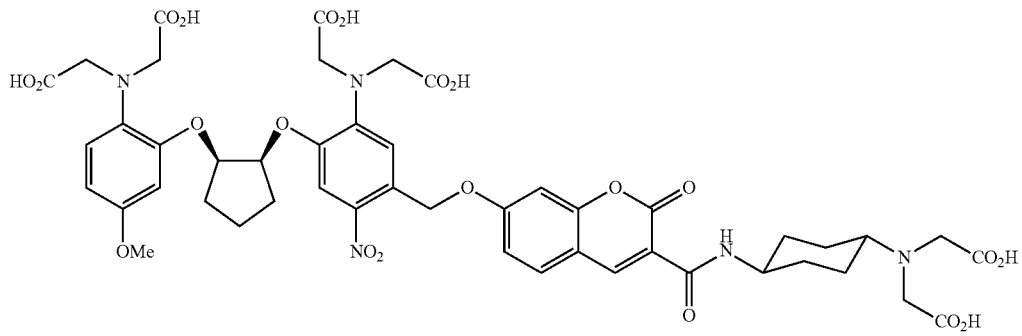 [SMILES: COc1ccc(N(CC(=O)O)CC(=O)O)c(O[C@@H]2CCC[C@@H]2Oc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]

Example 40

CpCDC$_2$-VO (11)

A vial was charged with alcohol 10 (68 mg, 80.4 μmol, 2.4 eq), 5-tert-butoxycarbonyl-2',7'-difluorocarbofluorescein (S34, 16.6 mg, 33.5 μmol), and PPh$_3$ (22.8 mg, 87.1 μmol, 2.6 eq). The vial was sealed and evacuated/backfilled with nitrogen (3×). THF (400 μL) was added, then DIAD (17.1 μL, 87.1 μmol, 2.6 eq) was added dropwise over 10 min. The reaction was stirred for an additional 90 min at room temperature. It was then directly purified by silica gel chromatography (0-20% EtOAc/toluene, linear gradient) to afford CpCDC$_2$-VO(t-Bu)$_9$ as a yellow gum (60 mg, 83%).

To a solution of the nonaester intermediate (60 mg, 27.9 μmol) in $CH_2Cl_2$ (4 mL) was added TFA (0.8 mL). The reaction was stirred at room temperature for 24 h while shielded from light. Toluene (4 mL) was added, and the resulting mixture was concentrated to dryness. The residue was purified by reverse phase HPLC (30-95% MeCN/$H_2O$, linear gradient, with constant 0.1% v/v TFA additive) to afford 11 as a yellow solid (bis-TFA salt, 36.1 mg, 69%) (structure shown below).

$^1$H NMR (CD$_3$OD, 400 MHz, mixture of diastereomers) δ 8.64-8.61 (m, 1H), 8.37-8.32 (m, 1H), 7.91-7.79 (m, 2H), 7.34-7.26 (m, 2H), 7.20-7.12 (m, 1H), 7.12-7.04 (m, 4H), 6.65-6.60 (m, 2H), 6.50-6.43 (m, 2H), 6.43-6.37 (m, 2H), 5.54 (s, 4H), 5.17-5.09 (m, 2H), 5.09-5.02 (m, 2H), 4.36-4.12 (m, 8H), 4.09-3.97 (m, 4H), 3.97-3.85 (m, 4H), 3.69 (s, 6H), 2.29-1.91 (m, 10H), 1.79-1.53 (m, 8H); Analytical HPLC: >99% purity (4.6 mm×150 mm 5 μm C18 column; 5 μL injection; 30-95% $CH_3CN/H_2O$, linear gradient, with constant 0.1% v/v TFA additive; 20 min run; 1 mL/min flow; ESI; positive ion mode; UV detection at 254/350 nm); MS (ESI) calcd for $C_{78}H_{75}F_2N_6O_{32}$ $[M+H]^+$ 1645.4, found 1645.2.

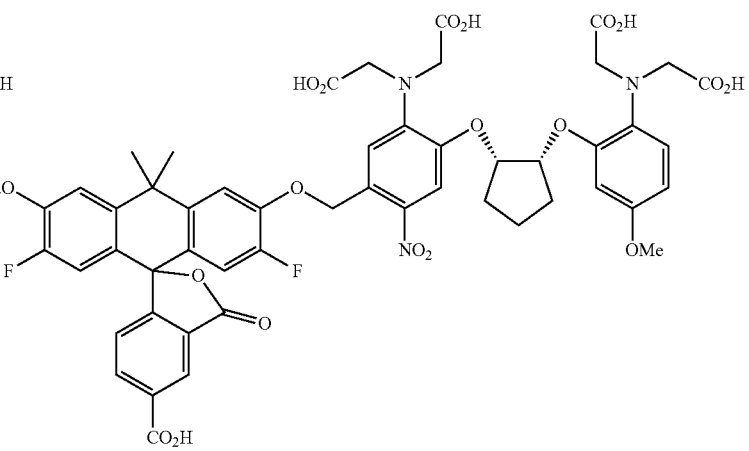

Throughout this document, various references are mentioned. All such references are incorporated herein by reference, including the references set forth in the following list:

REFERENCES (1) Lavis, L. D. & Raines, R. T. Bright ideas for chemical biology. *ACS Chem. Biol.* 3, 142-155 (2008).
(2) Lavis, L. D. & Raines, R. T. Bright building blocks for chemical biology. *ACS Chem. Biol.* 9, 855-866 (2014).
(3) Minta, A. & Tsien, R. Y. Fluorescent indicators for cytosolic sodium. *J. Biol. Chem.* 264, 19449-19457 (1989).
(4) Minta, A., Kao, J. P. & Tsien, R. Y. Fluorescent indicators for cytosolic calcium based on rhodamine and fluorescein chromophores. *J. Biol. Chem.* 264, 8171-8178 (1989).
(5) Martin, V. V., Rothe, A., Diwu, Z. & Gee, K. R. Fluorescent sodium ion indicators based on the 1,7-diaza-15-crown-5 system. *Bioorg. Med. Chem. Lett.* 14, 5313-5316 (2004).
(6) Adams, S. R. in *Imaging in neuroscience and development: a laboratory manual* (eds Rafael Yuste & Arthur Konnerth) Ch. 29,239-244 (CSHL Press, 2005).
(7) Nolan, E. M. & Lippard, S. J. Small-molecule fluorescent sensors for investigating zinc metalloneurochemistry. *Acc. Chem. Res.* 42, 193-203 (2008).
(8) Kamiya, M. & Johnsson, K. Localizable and highly sensitive calcium indicator based on a BODIPY fluorophore. *Anal. Chem.* 82, 6472-6479 (2010).
(9) Fujii, T. et al. Design and Synthesis of a FlAsH-Type Mg2+ Fluorescent Probe for Specific Protein Labeling. *J. Am. Chem. Soc.* 136, 2374-2381 (2014).
(10) Puliti, D., Warther, D., Orange, C., Specht, A. & Goeldner, M. Small photoactivatable molecules for controlled fluorescence activation in living cells. *Bioorg. Med. Chem.* 19, 1023-1029 (2011).
(11) Kantevari, S., Matsuzaki, M., Kanemoto, Y, Kasai, H. & Ellis-Davies, G. C. Two-color, two-photon uncaging of glutamate and GABA. *Nat. Methods* 7, 123-125 (2010).
(12) Fournier, L. et al. A blue-absorbing photolabile protecting group for in vivo chromatically orthogonal photoactivation. *ACS Chem. Biol.* 8, 1528-1536 (2013).
(13) Fosque, B. F. et al. Labeling of active neural circuits in vivo with designed calcium integrators. *Science* 347, 755-760 (2015).
(14) Venkatachalam, V. et al. Flash memory: Photochemical imprinting of neuronal action potentials onto a microbial rhodopsin. *J. Am. Chem. Soc.* 136, 2529-2537 (2014).
(15) Tsien, R. Y. New calcium indicators and buffers with high selectivity against magnesium and protons: Design, synthesis, and properties of prototype structures. *Biochemistry* 19, 2396-2404 (1980).
(16) Pethig, R. et al. On the dissociation constants of BAPTA-type calcium buffers. *Cell calcium* 10, 491-498 (1989).
(17) Schuddeboom, W., Warman, J. M., Biemans, H. & Meijer, E. Dipolar triplet states of p-nitroaniline and N-alkyl derivatives with one-, two-, and three-fold symmetry. *J. Phys. Chem.* 100, 12369-12373 (1996).
(18) Papageorgiou, G. & Corrie, J. E. Effects of aromatic substituents on the photocleavage of 1-acyl-7-nitroindolines. *Tetrahedron* 56, 8197-8205 (2000).
(19) Riguet, E. & Bochet, C. G. New safety-catch photolabile protecting group. *Org. Lett.* 9, 5453-5456 (2007).
(20) Guo, Y. M. et al. Imaging dynamic cell-cell junctional coupling in vivo using Trojan-LAMP. *Nat. Methods* 5, 835-841 (2008).
(21) Zhao, Y. R. et al. New caged coumarin fluorophores with extraordinary uncaging cross sections suitable for biological imaging applications. *J. Am. Chem. Soc.* 126, 4653-4663 (2004).
(22) Sabatini, B. L., Oertner, T. G. & Svoboda, K. The life cycle of Ca2+ ions in dendritic spines. *Neuron* 33, 439-452 (2002).
(23) Wang, S. S.-H., Denk, W. & Hausser, M. Coincidence detection in single dendritic spines mediated by calcium release. *Nat. Neurosci.* 3, 1266-1273 (2000).
(24) Maravall, M., Mainen, Z., Sabatini, B. & Svoboda, K. Estimating intracellular calcium concentrations and buffering without wavelength ratioing. *Biophys. J.* 78, 2655-2667 (2000).
(25) Grimm, J. B., Gruber, T. D., Ortiz, G., Brown, T. A. & Lavis, L. D. Virginia Orange: A versatile, red-shifted fluorescein scaffold for single-and dual-input fluorogenic probes. *Bioconjugate Chem.* 27, 474-480 (2016).
(26) Chan, J., Dodani, S. C. & Chang, C. J. Reaction-based small-molecule fluorescent probes for chemoselective bioimaging. *Nature Chem.* 4, 973-984 (2012).
(27) Matsuzaki, M. et al. Dendritic spine geometry is critical for AMPA receptor expression in hippocampal CA1 pyramidal neurons. *Nat. Neurosci.* 4, 1086-1092 (2001).
(28) Diwu, Z. et al. Fluorescent molecular probes. I. The synthesis and biological properties of an ELF b-glucuronidase substrate that yields fluorescent precipitates at the enzymic activity sites. *Tetrahedron* 53, 7159-7164 (1997).
(29) Kwan, D. H. et al. Self-immobilizing fluorogenic imaging agents of enzyme activity. *Angew. Chem. Int. Ed.* 123, 314-317 (2011).

(30) Urano, Y. et al. Evolution of fluorescein as a platform for finely tunable fluorescence probes. *J. Am. Chem. Soc.* 127, 4888-4894 (2005).
(31) Hatchard, C. & Parker, C. A new sensitive chemical actinometer. II. Potassium ferrioxalate as a standard chemical actinometer. *Proc. R. Soc. A* 235, 518-536 (1956).
(32) Akerboom, J. et al. Optimization of a GCaMP calcium indicator for neural activity imaging. *J. Neurosci.* 32, 13819-13840 (2012).

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound of the formula:

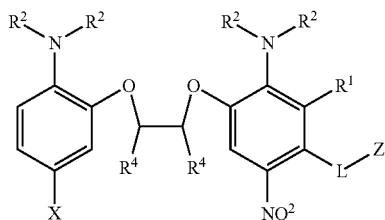

wherein:
Z includes a maskable molecule;
L is selected from a bond, C, C(O), O, alkyl, (O)alkyl, and alkoxy;
$R^1$ is selected from H, halogen, alkyl, and acyl;
each $R^2$ is independently selected from H, alkyl, aryl, and acyl, and is optionally substituted with one or more moieties independently selected from COOH and COO(alkyl) or the $R^2$ groups, taken together with the carbon atom to which they are bound, form a 4-10 membered ring;
each $R^4$ is independently selected from H, alkyl, and alkenyl; and
X is selected from H, alkyl, aryl, halogen, CN, OH, O(alkyl), O(aryl), SH, S(alkyl), S(aryl), amine, CHO, COOH, COO(alkyl), COO(aryl), $PO_3H_2$, pyrrolidine, and $SO_3H$, $R^3$ being optionally substituted with one or more moieties independently selected from N, O, and S, halogen, OH, O(alkyl), O(aryl), SH, S(alkyl), S(aryl), amine, NO, CHO, COO, COOH, COO(alkyl), COO(aryl), $C(O)NR_2$, $PO_3H_2$, and/or $SO_3H$.

2. The compound of claim 1, wherein Z is selected from the group consisting of a fluorophore and an active agent.

3. The compound of claim 2, wherein the active agent is selected from an enzyme, catalyst, ribozyme, organometallic, protein, glycoprotein, peptide, polyamino acid, antibody, nucleic acid, steroidal molecule, antibiotic, antiviral, antimycotic, anticancer agent, analgesic agent, antirejection agent, immunosuppressant, cytokine, carbohydrate, oleophobic, lipid, pharmaceutical, chemotherapeutic, and combinations thereof.

4. The compound of claim 1, wherein $R^2$ is selected from $CH_2COOH$ and $CH_2COO(alkyl)$.

5. The compound of claim 1, wherein X is selected from methoxy and pyrrolidine.

6. The compound of claim 1, according to the formula:

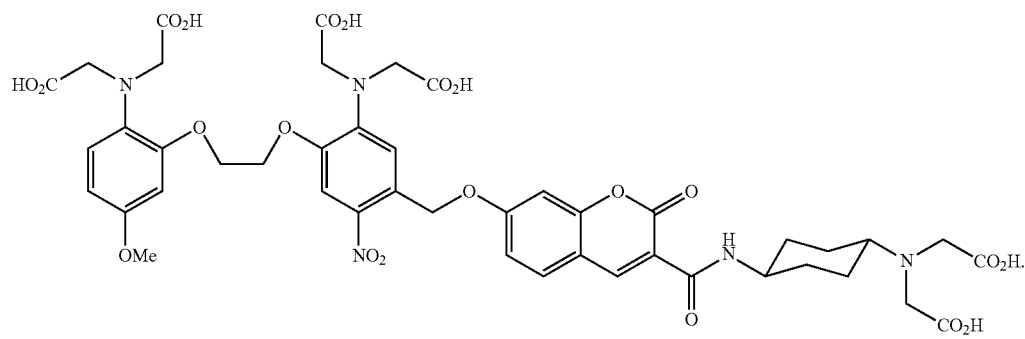 [SMILES: COc1ccc(N(CC(=O)O)CC(=O)O)c(OCCOc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]

7. The compound of claim 1, according to the formula:

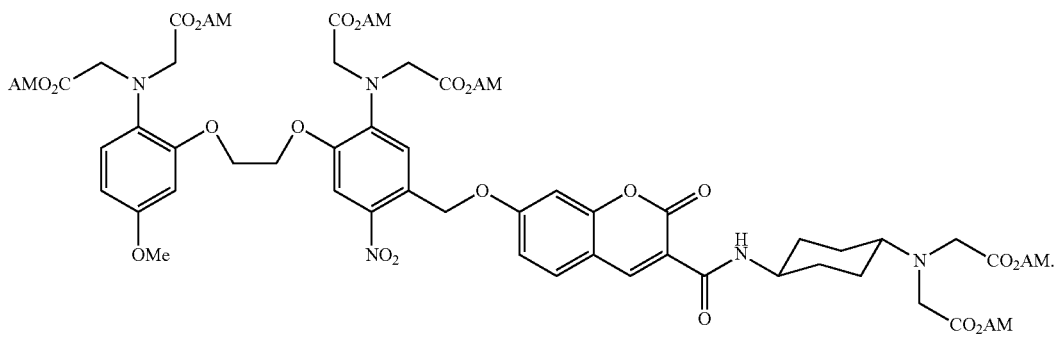

8. The compound of claim 1, according to the formula:
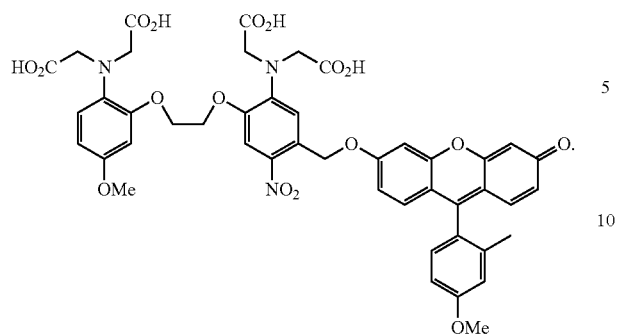
9. The compound of claim 1, according to the formula:
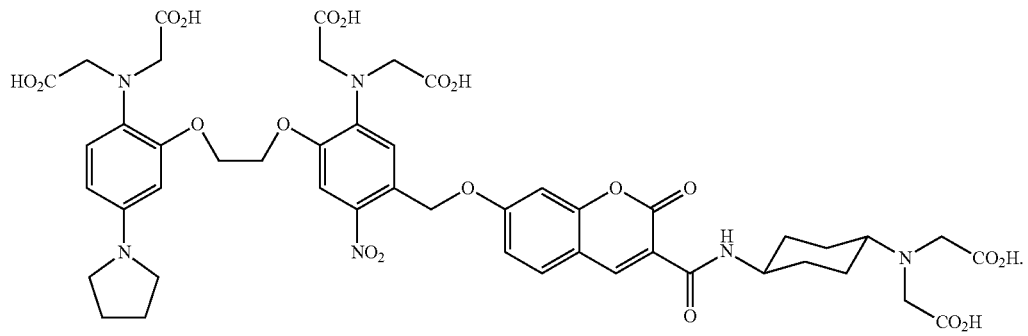 [SMILES: O=C(O)CN(CC(=O)O)c1ccc(N2CCCC2)cc1OCCOc1cc([N+](=O)[O-])c(COc2ccc3cc(C(=O)NC4CCC(N(CC(=O)O)CC(=O)O)CC4)c(=O)oc3c2)cc1N(CC(=O)O)CC(=O)O]
10. The compound of claim 1, wherein the R⁴ groups, taken together with the carbon atoms to which they are bound, form a 5-6 membered ring.
11. The compound of claim 10, according to the formula:
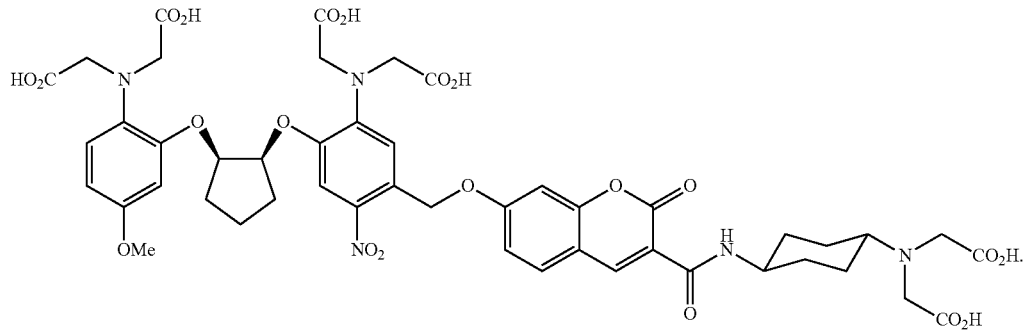 [SMILES: COc1ccc(N(CC(=O)O)CC(=O)O)c(O[C@@H]2CCC[C@@H]2Oc2cc([N+](=O)[O-])c(COc3ccc4cc(C(=O)NC5CCC(N(CC(=O)O)CC(=O)O)CC5)c(=O)oc4c3)cc2N(CC(=O)O)CC(=O)O)c1]
12. The compound of claim 10, according to the formula:
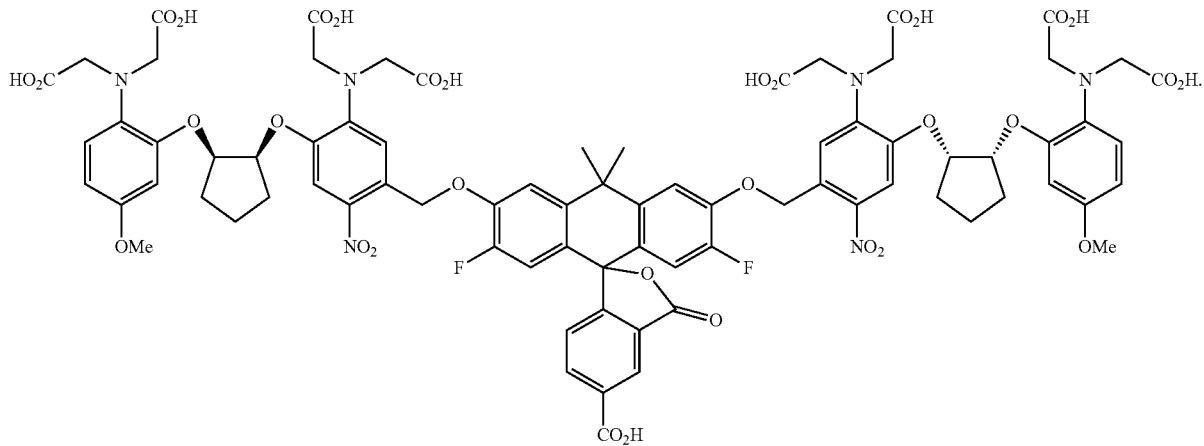 [SMILES: COc1ccc(N(CC(=O)O)CC(=O)O)c(O[C@@H]2CCC[C@@H]2Oc2cc([N+](=O)[O-])c(COc3cc4c(cc3F)C3(OC(=O)c5cc(C(=O)O)ccc53)c3cc(F)c(OCc5cc(N(CC(=O)O)CC(=O)O)c(O[C@H]6CCC[C@H]6Oc6cc(OC)ccc6N(CC(=O)O)CC(=O)O)cc5[N+](=O)[O-])cc3C4(C)C)cc2N(CC(=O)O)CC(=O)O)c1]
* * * * *

UNITED STATES PATENT AND TRADEMARK OFFICE
CERTIFICATE OF CORRECTION

PATENT NO. : 10,407,399 B2  
APPLICATION NO. : 15/756788  
DATED : September 10, 2019  
INVENTOR(S) : Luke D. Lavis et al.

Page 1 of 1

It is certified that error appears in the above-identified patent and that said Letters Patent is hereby corrected as shown below:

In the Claims

Claim 1, Column 59, Lines 26-34, replace:

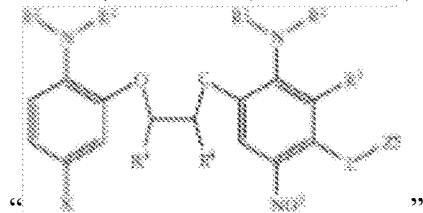

With:

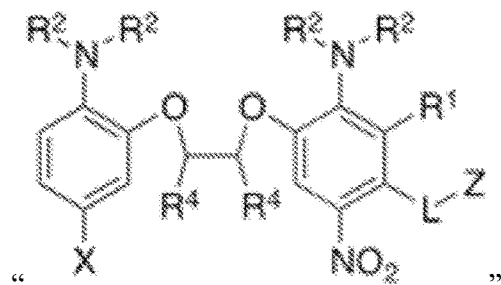

Claim 1, Column 60, Line 18, replace:
"amine, NO, CHO,"

With:
"amine, $NO_2$, CHO"

Signed and Sealed this  
Fifth Day of November, 2019

Andrei Iancu  
*Director of the United States Patent and Trademark Office*